(12) United States Patent
Lifton et al.

(10) Patent No.: US 9,982,026 B2
(45) Date of Patent: May 29, 2018

(54) COMPOSITIONS AND METHODS FOR ASSESSING AND TREATING ADRENAL DISEASES AND DISORDERS

(75) Inventors: Richard P. Lifton, North Haven, CT (US); Bixiao Zhao, Plainsboro, NJ (US); Murim Choi, Seoul (KR); Goran Akerstrom, Uppsala (SE); Gunnar Westin, Uppsala (SE); Peyman Bjorklund, Stockholm (SE); Per Hellman, Uppsala (SE)

(73) Assignee: YALE UNIVERSITY, New Haven, CT (US)

( * ) Notice: Subject to any disclaimer, the term of this patent is extended or adjusted under 35 U.S.C. 154(b) by 0 days. days.

(21) Appl. No.: 13/978,098

(22) PCT Filed: Jan. 4, 2012

(86) PCT No.: PCT/US2012/020188
§ 371 (c)(1),
(2), (4) Date: Jan. 21, 2014

(87) PCT Pub. No.: WO2012/094394
PCT Pub. Date: Jul. 12, 2012

(65) Prior Publication Data
US 2014/0127126 A1 May 8, 2014

Related U.S. Application Data

(60) Provisional application No. 61/429,498, filed on Jan. 4, 2011.

(51) Int. Cl.
| | | |
|---|---|---|
| *C12Q 1/68* | (2018.01) | |
| *C12P 19/34* | (2006.01) | |
| *C07H 21/02* | (2006.01) | |
| *C07H 21/04* | (2006.01) | |
| *C07K 14/435* | (2006.01) | |
| *C07K 14/705* | (2006.01) | |
| *A61K 49/06* | (2006.01) | |
| *A61K 51/00* | (2006.01) | |
| *G01N 33/68* | (2006.01) | |

(52) U.S. Cl.
CPC ............ *C07K 14/435* (2013.01); *A61K 49/06* (2013.01); *A61K 51/00* (2013.01); *C07K 14/705* (2013.01); *C12Q 1/686* (2013.01); *C12Q 1/6883* (2013.01); *C12Q 1/6886* (2013.01); *G01N 33/6893* (2013.01); *C12Q 2600/156* (2013.01)

(58) Field of Classification Search
CPC ....... G01N 2333/726; G01N 2800/321; C12Q 1/6883; C12Q 1/6837; C12Q 2600/118; C12Q 2600/156
See application file for complete search history.

(56) References Cited

U.S. PATENT DOCUMENTS

2009/0148861 A1* 6/2009 Pegan et al. .................. 435/7.1

OTHER PUBLICATIONS

Yin Y. et al. European Heart Journal (2006) 27, 1841-1846.*
Zhang C. et al. Heart, Lung and Circulation 2009;18:257-261.*
GenBank Locus: NM_000890 *Homo sapiens* potassium inwardly-rectifying channel, subfamily J, member 5 (KCNJ5), mRNA, from www.ncbi.nlm.nih.gov, pp. 1-4.*
Lucentini, J. The Scientist (Dec. 20, 2004), p. 20.*
Pennisi E. Science; Sep 18, 1998; vol. 281, No. 5384, p. 1787-1789.*
Hegele R.A. (Arterioscler Thromb Vasc Biol. 2002;22:1058-1061.*
Choi et al.,"K+ channel mutations in adrenal aldosterone-producing adenomas and hereditary hypertension," Science 331:768. (2011).
Calloe et al., 2007, "Characterizations of a loss-of-function mutation in the Kir3.4 channel subunit," Biochem Biophys Res Comm 364:889.
Lancaster et al., 2000, "Residues and mechanisms for slow activation and Ba2+ block of the cardiac muscarinic K+ channel, Kir3.1/Kir3.4," J Biol Chem 275:35831.
Calvo-Romero and Ramos-Salado, 2000, "Recurrence of adrenal aldosterone-producing adenoma," Postgrad. Med. J. 76:160.
Young, 2007, "Primary aldosteronism: renaissance of a syndrome," Clin Endocrinol (Oxf) 66:607-618.
Rossi et al., 2006, "A prospective study of the prevalence of primary aldosteronism in 1,125 hypertensive patients," J Am Coll Cardiol. 48:2293-2300.
Rossi et al., 2008, " Primary aldosteronism: an update on screening, diagnosis and treatement," J Hypertens 26:613-621.
Mathur et al., 2010, Consequences of adrenal venous sampling in primary hyperaldosteronism and predictors of unilateral adrenal disease, J Am Coll Surg. 211:384-390.
Heginbotham et al., 1994, "Mutations in the K+ channel signature sequence," Biophys. J. 66:1061.
Dibb et al., 2003, "Molecular basis of ion selectivity, block, and rectification of the inward rectifier Kir3.1/Kir3.4 K+ channel," J. Biol. Chem. 278:49537.
Geller et al., 2008, "A novel form of human Mendelian hypertension featuring nonglucocorticoid remediable aldosteronism," J. Clin. Endocrinol. Metab. 93:3117.
Spat and Hunyady, 2004, "Control of aldosterone secretion: A model for convergence in cellular signaling pathways," Physiol. Rev. 84:489.
Navarro et al., 1996, "Nonselective and G-beta-gamma-insensitive weaver K+ channels," Science 272:1950.
Tao et al., 2009, "Crystal structure of the eukaryotic strong inward-rectifier K+ channel Kir2.2 at 3.1 angstrom resolution," Science 326:1668-1674.
Krapivinsky et al., 1995, "The G-protein-gated atrial K+ channel I-KACh is a heteromultimer of two inwardly rectifying K+ channel proteins," Nature 374:135.

(Continued)

*Primary Examiner* — Stephen T Kapushoc
(74) *Attorney, Agent, or Firm* — Riverside Law LLP

(57) ABSTRACT

The present invention relates to the discovery that mutations in KCNJ5 are associated with adrenal diseases and disorders. The invention includes compositions and methods for the assessment, characterization and treatment of adrenal diseases and disorders, based upon the presence or absence of a KCNJ5 mutation that is associated with an adrenal disease or disorder.

6 Claims, 35 Drawing Sheets

(56) References Cited

OTHER PUBLICATIONS

Doyle et al., 1998, "The structure of the potassium channel: Molecular basis of K+ conduction and selectivity," Science 280:69.
Roux, 2005, "Ion conduction and selectivity in K+ channels," Annu. Rev. Biophys. Biomol. Struct. 34:153.

* cited by examiner

| Tumor | Chr | Position | Base change | Gene | Effect on protein | No. of reads from tumor | | | No. of reads from blood | | P |
|---|---|---|---|---|---|---|---|---|---|---|---|
| | | | | | | Ref. allele | Non-ref. allele | % of all reads | Ref. allele | Non-ref. allele | |
| APA9 | 14 | 99,813,560 | C>G | YY1 | T372R | 115 | 69 | 37.5% | 184 | 0 | $1.3 \times 10^{-24}$ |
| | 9 | 114,858,771 | C>G | ZFP37 | V7L | 47 | 23 | 32.9% | 77 | 0 | $4.0 \times 10^{-10}$ |
| APA12 | 11 | 86,341,084 | C>A | F2D4 | C121F | 491 | 139 | 22.1% | 871 | 0 | $1.6 \times 10^{-55}$ |
| | 11 | 128,286,829 | G>A | KCNJ5 | G151R | 120 | 59 | 33.0% | 290 | 0 | $1.9 \times 10^{-28}$ |
| | 12 | 56,159,281 | G>A | ABHGAP9 | R66C | 149 | 65 | 30.4% | 282 | 0 | $1.1 \times 10^{-25}$ |
| APA15 | 11 | 128,286,881 | T>G | KCNJ5 | L168R | 159 | 65 | 29.0% | 456 | 0 | $3.5 \times 10^{-25}$ |
| | X | 53,239,430 | C>T | KDM5C | V1341M Exon 13 | 30 | 30 | 50.0% | 54 | 0 | $7.6 \times 10^{-11}$ |
| APA22 | 21 | 43,054,087 | G>A | PDE9A | splice donor GT>AT | 90 | 31 | 25.6% | 123 | 0 | $6.9 \times 10^{-10}$ |
| | 2 | 140,918,376 | T>G | LRP1B | R3429S | 60 | 14 | 18.9% | 80 | 0 | $1.7 \times 10^{-5}$ |

| Patient | Age | Gender | ARR | Tumor Weight (g) | Tumor Diameter (mm) | HTN | Serum K+ (mmol/L) | # of LOH chromosomes | Tumor KCNJ5 genotype |
|---|---|---|---|---|---|---|---|---|---|
| APA10 | 37 | F | 436 | 12 | 25 | + | 3.8 | 0 | G151R+ |
| APA12 | 34 | F | 1,290 | 15.1 | 25 | + | 3.7 | 0 | G151R+ |
| APA8 | 48 | F | 352 | 11 | 8 | + | 3.4 | 0 | L168R+ |
| APA9 | 33 | F | 712 | 9.3 | 28 | + | 3.9 | 0 | L168R+ |
| APA15 | 34 | M | 700 | 14 | 23 | + | 3.1 | 0 | L168R+ |
| APA19 | 56 | F | 230 | NA | 20 | + | 3.4 | 0 | L168R+ |
| APA20 | 31 | F | 457 | NA | 22 | + | 2.5* | 0 | L168R+ |
| APA18 | 37 | F | 480 | 13.8 | 40 | + | 4.3 | 1 | L168R+ |
| APA16 | 34 | F | 359 | NA | 46 | + | 3.4 | 0 | WT |
| APA9 | 28 | F | 256 | 46 | 48 | + | 3.4 | 0 | WT |
| APA11 | 39 | M | 500 | 8.2 | 10 | + | 3.9* | 0 | WT |
| APA22 | 65 | F | 271 | NA | 25 | + | 3.5 | 0 | WT |
| APA1 | 44 | F | 235* | 8.5 | 9 | + | 3.3 | 1 | WT |
| APA4 | 39 | F | 384 | 35 | 41 | + | 3.6 | 4 | WT |
| APA6 | 63 | M | 241 | 22 | 24 | + | 4.1 | 11 | WT |
| APA14 | 60 | M | 246 | NA | 45 | + | 3.8 | 11 | WT |
| APA7 | 53 | F | 483 | 41 | 45 | + | 3.5 | 13 | WT |
| APA2 | 34 | M | 335* | 31 | 25 | + | 3.4 | 15 | WT |
| APA3 | 63 | F | 618 | 14 | 20 | + | 2.5* | 16 | WT |
| APA17 | 39 | M | 243 | NA | 33 | + | 3.8 | 17 | WT |
| APA13 | 53 | F | 317 | 31 | 33 | + | 3.5 | 19 | WT |
| APA21 | 57 | F | 326 | 28 | 32 | + | 3.5 | 19 | WT |
| Mean | 43.3 | NA | 420.8 | 20.7 | 28.3 | NA | 3.5 | 5.8 | NA |
| SD | 12.3 | NA | 239.6 | 12.5 | 12.2 | NA | 0.4 | 7.5 | NA |

ARR: aldosterone renin ratio in (pmol/L)/(mIU/L plasma renin concentration) (> 50 indicative of primary aldosteronism) except two subjects (*) in whom ARR was measured in (pmol/L)/(ng/L/h plasma renin activity) (> 100 indicative of primary aldosteronism); HTN: hypertension; Serum K+: preoperative serum potassium (reference range 3.5-5.0 mmol/L) while on potassium therapy except in three subjects, without potassium supplementation (*); # of LOH chromosomes: number of chromosomes with loss of heterozygosity; NA, not available.

Figure 14

| Sample | AP10 | | AP12 | | AP13 | | AP16 | | AP22 | |
|---|---|---|---|---|---|---|---|---|---|---|
| Source | Blood | Tumor | Blood | Tumor | Blood | Tumor | Blood | Tumor | Blood | Tumor |
| # of total bases | 16.9 Gb | 17.3 Gb | 16.9 Gb | 16.7 Gb | 15.8 Gb | 15.2 Gb | 17.1 Gb | 16.3 Gb |
| % of bases mapping to genome | 97.6% | 98.4% | 96.3% | 95.7% | 98.1% | 99.2% | 98.2% | 98.3% |
| % of bases mapping to exome | 62.7% | 63.2% | 61.9% | 47.2% | 63.8% | 69.2% | 64.4% | 64.9% |
| Mean unique reads per targeted base | 172.8X | 165.3X | 180.4X | 146.6X | 152.9X | 118.6X | 210.0X | 193.0X |
| % of bases read at least 8x | 96.5% | 96.5% | 96.7% | 96.6% | 94.3% | 96.5% | 96.7% | 97.1% |
| Sensitivity of heterozygote detection | 98.6% | 98.6% | 98.8% | 98.8% | 95.9% | 98.4% | 99.0% | 98.8% |
| Specificity of heterozygous calls | 99.9% | 99.9% | 99.9% | 99.9% | 99.8% | 99.8% | 99.9% | 99.9% |

Gb, 10⁹ bases; Sensitivity, % of heterozygous calls by SNP genotyping that were called heterozygous by sequencing; Specificity, % of heterozygous calls by sequence at genotyped SNP positions called heterozygous by SNP genotyping.

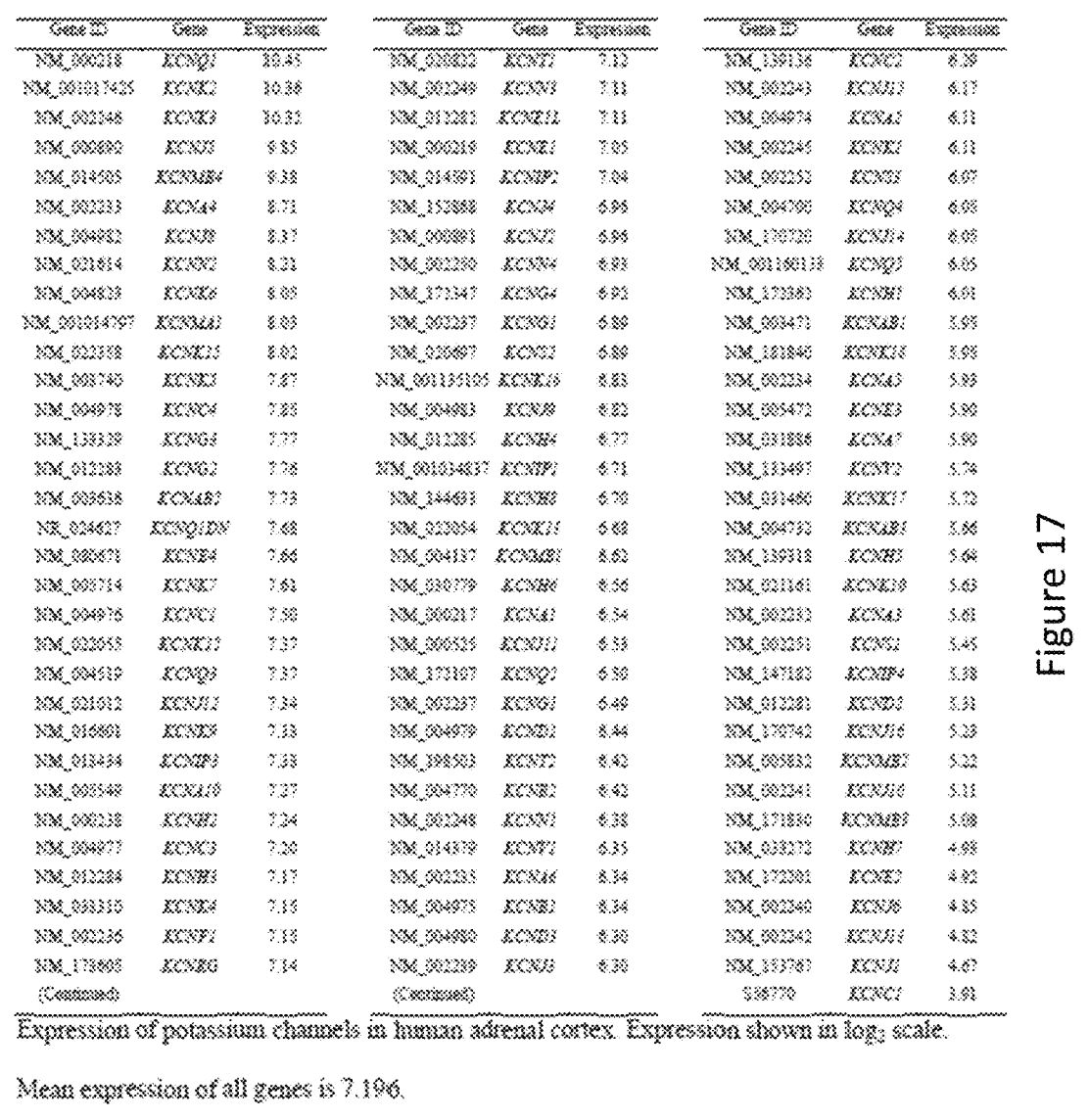

Expression of potassium channels in human adrenal cortex. Expression shown in log₂ scale.

Mean expression of all genes is 7.196.

Figure 17

| Patient | Age at presentation (years) | Gender | Blood Pressure (mmHg) | PRA (ng/ml/h) | Serum Aldosterone (ng/dl) | 24-h urine Aldosterone (μg/24h) | Serum K+ (mmol/l) | KCNJ5 Genotype |
|---|---|---|---|---|---|---|---|---|
| HPAI-1 | 5 | Male | 230/140 | NA | NA | 67 | 2.8 | T158A/+ |
| HPAI-2 | 7 | Female | 188/140 | 0.3 | 137.4 | NA | 1.8 | T158A/+ |
| HPAI-3 | 4 | Female | 148/114 | 0.2 | 185.1 | NA | 1.9 | T158A/+ |

PRA: Plasma renin activity (reference range 0.4-8.8 ng/ml/h); Serum Aldosterone (reference range 3-39.5 ng/dl); 24-h urine aldosterone (reference range 1-8 μg/24h); Serum K+: serum potassium concentration (reference range 3.5-5 mmol/liter); NA: not available.

Figure 18

| Variable | Total cohort | Wild Type | KCNJ5 mutations All mutations | G151R | L168R | E145Q |
|---|---|---|---|---|---|---|
| Adenoma without associated hyperplasia - no. (%) | 287 | 151 (53%) | 136 (47%) | 74 (26%) | 60 (21%) | 2 (0.7%) |
| Males - no. (%) | 109 (38%) | 85 (78%) | 24 (22%)* | 13 (12%) | 11 (10%) | 0 (0%) |
| Females - no. (%) | 178 (62%) | 66 (37%) | 112 (63%)* | 61 (34%) | 49 (28%) | 2 (1.1%) |
| Age at operation - yr (range): | 49 (18-79) | 52 (26-79) | 46 (18-78) | 46 (18-78) | 44 (23-75) | 46 (45-47) |
| Males | 53 (15-79) | 54 (30-75) | 45 (16-67)† | 46 (16-55) | 45 (29-67) | - |
| Females | 47 (23-79) | 49 (26-79) | 46 (23-78) | 47 (25-78) | 44 (23-75) | 46 (45-47) |
| Adenoma size - mm (range): | 17.3 (6-47) | 15.9 (6-47) | 18.8 (6-47) | 18.9 (6-47) | 18.4 (6-40) | 8 (6-10) |
| Males | 19.7 (6-47) | 17.1 (6-47)§ | 27.1 (6-47)§ | 32.5 (6-47)§ | 18.6 (6-38) | - |
| Females | 16.1 (6-45) | 14.9 (6-45) | 18.7 (7-40) | 19.3 (9-38) | 18.3 (7-40) | 8 (6-10) |
| Adenoma with associated hyperplasia - no. (%) | 52 | 31 (60%) | 21 (40%) | 10 (19%) | 11 (21%) | 0 (0%) |
| Males | 36 (69%) | 25 (69%) | 11 (31%)¶ | 4 (11%) | 7 (19%) | 0 (0%) |
| Females | 16 (31%) | 6 (38%) | 10 (63%)¶ | 6 (38%) | 4 (25%) | 0 (0%) |
| Age at operation - yr (range): | 53 (22-73) | 54 (40-68) | 49 (22-73) | 55 (47-73) | 42 (22-69) | - |
| Males | 52 (22-68) | 56 (40-68) | 43 (22-60) | 51 (47-60) | 39 (22-57)† | - |
| Females | 54 (37-73) | 52 (44-65) | 55 (37-73) | 60 (54-73) | 47 (37-69) | - |
| Hyperplasia - no. (%) | 9 | 9 (100%) | 0 (0%) | - | - | - |
| Males | 6 (67%) | 6 (67%) | - | - | - | - |
| Females | 3 (33%) | 3 (33%) | - | - | - | - |
| Age at operation - yr (range): | 51 (38-62) | 51 (38-62) | - | - | - | - |
| Males | 49 (38-55) | 49 (38-55) | - | - | - | - |
| Females | 54 (44-62) | 54 (44-62) | - | - | - | - |

*, †, §, ¶ and ‡ chi-square p-value < 0.005

| Lesion characteristics | Age at operation - yr (range) | Male to female ratio | Tumor size |
|---|---|---|---|
| Cortisol producing adenomas (n=30) | 34 (22-62) | 1:2 | 34 (10-50) |
| Cortisol producing carcinomas (n=20) | 38 (28-42) | 1:1.5 | 58 (35-80) |
| Non functioning adenomas (n=50) | 53 (38-71) | 1:1 | 63 (55-85) |
| Non functioning carcinomas (n=30) | 47 (31-74) | 1:1 | 80 (55-210) |

Figure 23

COMPOSITIONS AND METHODS FOR ASSESSING AND TREATING ADRENAL DISEASES AND DISORDERS

CROSS-REFERENCE TO RELATED APPLICATION

This application is the U.S. national phase application filed under 35 U.S.C. § 371 claiming benefit to International Patent Application No. PCT/US2012/020188, filed on Jan. 4, 2012, which is entitled to priority under 35 U.S.C. § 119(e) to U.S. Provisional Patent Application No. 61/429,498, filed on Jan. 4, 2011, each of which application is hereby incorporated herein by reference in its entirety.

STATEMENT REGARDING FEDERALLY SPONSORED RESEARCH OR DEVELOPMENT

This invention was made with government support under Grant No. DK54983, awarded by the National Institutes of Health. The Government has certain rights in the invention.

BACKGROUND OF THE INVENTION

Aldosterone, a steroid hormone synthesized by the adrenal glomerulosa, is normally produced in two conditions, intravascular volume depletion and hyperkalemia (high plasma K+ level) (Spät and Hunyady, 2004, Physiol. Rev. 84:489). Volume depletion activates the renin-angiotensin system, producing the hormone angiotensin II (AII), which signals via its G protein-coupled receptor (GPCR) in glomerulosa cells. The resting membrane potential is set by K+ channel activity (Spät, 2004, Mol. Cell. Endocrinol. 217: 23); both AII signaling and hyperkalemia cause membrane depolarization and activation of voltage-gated Ca2+ channels. Increased intracellular Ca2+ provides the normal signal for aldosterone production, and sustained increases lead to glomerulosa cell proliferation (Spät and Hunyady, 2004, Physiol. Rev. 84:489; McEwan et al., 1996, Am. J. Physiol. 271, E192; Pawlikowski et al., 2001, Endocr. Regul. 35:139; Tanabe et al., 1998, J. Endocrinol. Invest. 21:668); AII also causes increased inositol 1,4,5-trisphosphate (IP3) and transient Ca2+ release from intracellular stores. Aldosterone signaling in the kidney increases electrogenic Na+ reabsorption, defending intravascular volume, and also increases K+ secretion.

In primary aldosteronism, the adrenal gland constitutively produces aldosterone in the absence of AII or hyperkalemia, resulting in hypertension and variable hypokalemia (low plasma K+ level). Primary aldosteronism is found in ~10% of patients referred for evaluation of hypertension. A third or more of these have aldosterone-producing adenoma (APA, also known as Conn's syndrome) of the adrenal cortex (Rossi et al., 2006, J. Am. Coll. Cardiol. 48:2293); of the remainder, a small fraction have mutations that cause constitutive expression of aldosterone synthase (Lifton et al., 1992, Nature 355:262), and the rest are classified as idiopathic.

APAs are typically solitary, well circumscribed, and diagnosed between ages 30 and 70 (V. Kumar. A. K. Abbas, N. Fausto, J. C. Aster, Eds., in Robbins and Cotran Pathologic Basis of Disease (Saunders, Philadelphia, ed. 8, 2009), chap. 24). They come to medical attention due to new or worsening hypertension, often with hypokalemia. Aldosterone is elevated while renin levels are suppressed (reflected in a high aldosterone:renin ratio), and a characteristic adrenal mass can be seen on computed tomography (CT). Adrenal vein sampling demonstrates predominant aldosterone secretion from the gland harboring the tumor. APAs virtually always remain benign, without local invasion or distant metastasis (Ghose et al., 1999, Ann. Intern. Med. 131:105). Surgical removal ameliorates or cures hypertension in the large majority of patients (Calvo-Romero and Ramos-Salado, 2000, Postgrad. Med. J. 76:160). The mechanisms responsible for neoplasia and cell-autonomous aldosterone production are unknown.

Screening studies of hypertensive patient populations have revealed primary aldosteronism as the most common cause of secondary hypertension, and together with recognition of the association with severe cardiovascular complications, have produced a renewed focus on the syndrome of primary aldosteronism (Young, 2007, Clin Endocrinol (Oxf) 66:607-618; Gordon et al., 1992, Lancet 340:159-161; Rossi et al., 2006, J Am Coll Cardiol. 48:2293-2300; Rossi et al., 2008, J Hypertens 26:613-621; Rossi, 2011, Endocrinol Metab Clin North Am. 40:313-332; Stowasser and Gordon, 2003, Primary aldosteronism. Best Pract Res Clin Endocrinol Metab. 17:591-605). This has led to marked improvement in guidelines for case detection, diagnosis and treatment (Funder et al., 2008, J Clin Endocrinol Metab. 93:3266-3281). Case detection has been recommended in all patients with hypertension, and should be based on PAC/PRA (or PRC) ratio (with laboratory dependent cut-off values), and confirmation of the diagnosis by either of various suppression tests (oral sodium loading, saline infusion, captopril test, and fludrocortisone suppression tests) (Gordon et al., 1992, Lancet 340:159-161; Rossi, 2011, Endocrinol Metab Clin North Am. 40:313-332; Funder et al., 2008, J Clin Endocrinol Metab. 93:3266-3281; Westerdahl et al., 2009, Scand J Clin Lab Invest. 69:234-241). The combination of adrenal CT and adrenal vein sampling is recommended for identification of unilateral lesions, which are potentially curable by surgery, and for appropriate lateralization diagnosis prior to operation (Funder et al., 2008, J Clin Endocrinol Metab. 93:3266-3281). CT identification of a unilateral adrenal lesion in younger patients (<40 years) with primary aldosteronism may represent an appropriate indication for surgery, although demonstration of lateralization of aldosterone secretion is otherwise claimed to be essential to maximize benefits of surgical intervention (Young, 2007, Clin Endocrinol (Oxf) 66:607-618; Funder et al., 2008, J Clin Endocrinol Metab. 93:3266-3281; Mathur et al., 2010, J Am Coll Surg. 211:384-390).

Despite the advances made in the genetic classification and treatment of adrenal diseases and disorders, there is a need in the art for the further discovery of novel mutations that can drive the development of diagnostics and the selection of targeted therapies to treat adrenal diseases and disorders. The present invention fulfills these needs.

SUMMARY OF THE INVENTION

The invention relates to the discovery that mutations in KCNJ5 are associated with adrenal diseases and disorders. The invention relates to compositions and methods useful for the assessment, characterization and treatment of an adrenal disease or disorder, based upon the presence or absence of a KCNJ5 mutation that is associated with an adrenal disease or disorder.

In one embodiment, the invention is an isolated KCNJ5 polypeptide having an amino acid sequence comprising at least one mutation in or near the KCNJ5 selectivity filter. In another embodiment, the at least one mutation is at an amino acid residue position from about 140 to about 180 relative to SEQ ID NO:13. In other embodiments, the at least one mutation is at least one selected from the group consisting of G151X, L168X, T158X and E145X. In a further embodiment, the at least one mutation is at least one selected from the group consisting of G151A, L168R, T158A and E145Q.

In another embodiment, the invention is an isolated KCNJ5 nucleic acid having a nucleotide sequence comprising at least one mutation, wherein the nucleic acid having at least one mutation encodes a polypeptide having an amino acid sequence comprising at least one mutation in or near the KCNJ5 selectivity filter. In one embodiment, the at least one mutation is at an amino acid residue position from about 140 to about 180 relative to SEQ ID NO:13. In other embodiments, the at least one mutation is at least one selected from the group consisting of G151X, L168X, T158X and E145X. In a further embodiment, the at least one mutation is at least one selected from the group consisting of G151A, L168R, T158A and E145Q.

In a further embodiment, the invention is a method of identifying a mutant KCNJ5 sequence in a biological sample obtained from a subject. In various embodiments, the method includes the steps of: obtaining a biological sample from the subject, determining the sequence of at least a portion of the subject's KCNJ5 sequence, comparing the subject's KCNJ5 sequence to a wild-type KCNJ5 sequence, and identifying at least one mutation in the subject's KCNJ5 sequence as compared with the wild-type KCNJ5 sequence. In some embodiments, the KCNJ5 sequence is a nucleic acid sequence that encodes a polypeptide having at least one mutation. In other embodiments, the KCNJ5 sequence is an amino acid sequence having at least one mutation. In some embodiments, the at least one mutation is at least one selected from the group consisting of G151X, L168X, T158X and E145X. In other embodiments, the at least one mutation is at least one selected from the group consisting of G151A, L168R, T158A and E145Q. In a preferred embodiment, the subject is human. In some embodiments, the step of determining the sequence of the subject's KCNJ5 sequence employs PCR. In various embodiments, the biological sample is at least one of blood, plasma, serum, a body fluid, a tissue, a tumor, or a cell.

In another embodiment, the invention is a method of diagnosing a disease or disorder in a subject in need thereof, including the steps of: obtaining a biological sample from the subject, determining the sequence of at least a portion of the subject's KCNJ5 sequence, comparing the subject's KCNJ5 sequence to a wild-type KCNJ5 sequence, and identifying at least one mutation in the subject's KCNJ5 sequence as compared with the wild-type KCNJ5 sequence. In some embodiments, the KCNJ5 sequence is a nucleic acid sequence that encodes a polypeptide having at least one mutation. In other embodiments, the KCNJ5 sequence is an amino acid sequence having at least one mutation. In some embodiments, the at least one mutation is at least one selected from the group consisting of G151X, L168X, T158X and E145X. In other embodiments, the at least one mutation is at least one selected from the group consisting of G151A, L168R, T158A and E145Q. In a preferred embodiment, the subject is human. In some embodiments, the step of determining the sequence of the subject's KCNJ5 sequence employs PCR. In various embodiments, the biological sample is at least one of blood, plasma, serum, a body fluid, a tissue, a tumor, or a cell. In some embodiments, the disease or disorder is an adrenal disease or disorder. In particular embodiments, the adrenal disease or disorder is at least one of: aldosteronism, primary aldosteronism, secondary aldosteronism, hyperaldosteronism, primary hyperaldos-teronism, secondary hyperaldosteronism, adrenal insufficiency, Addison's Disease, adrenoleukodystrophy, pheochromocytoma, Cushing's Syndrome, adrenal hyperplasia, congenital adrenal hyperplasia, cancer, adrenal cancer, hypertension, primary hypertension, secondary hypertension or virilization.

In one embodiment, the invention is a method of treating a disease or disorder in a subject in need thereof, the method including the steps of: administering to the subject, a therapeutically effective amount of a modulator of mutant KCNJ5, wherein the subject has been diagnosed as having a disease or disorder, and wherein after the modulator of mutant KCNJ5 is administered to the subject, the disease or disorder is treated. In various embodiments, the modulator is at least one of: a chemical compound, a protein, a peptide, a peptidomemetic, an antibody, a ribozyme, a small molecule chemical compound, and an antisense nucleic acid molecule. In some embodiments, the subject has at least one mutation in KCNJ5. In other embodiments, the subject has at least one mutation in KCNJ5 in or near the KCNJ5 selectivity filter. In another embodiment, the at least one mutation is at an amino acid residue position from about 140 to about 180 relative to SEQ ID NO:13. In other embodiments, the at least one mutation is at least one selected from the group consisting of G151X, L168X, T158X and E145X. In a further embodiment, the at least one mutation is at least one selected from the group consisting of G151A, L168R, T158A and E145Q. In a preferred embodiment, the subject is human. In some embodiments, the disease or disorder is an adrenal disease or disorder. In particular embodiments, the adrenal disease or disorder is at least one of: aldosteronism, primary aldosteronism, secondary aldosteronism, hyperaldosteronism, primary hyperaldosteronism, secondary hyperaldosteronism, adrenal insufficiency, Addison's Disease, adrenoleukodystrophy, pheochromocytoma, Cushing's Syndrome, adrenal hyperplasia, congenital adrenal hyperplasia, cancer, adrenal cancer, hypertension, primary hypertension, secondary hypertension or virilization.

In yet another embodiment, the invention is a method of identifying a test compound as a modulator of mutant KCNJ5 selectivity filter, including the steps of: measuring the activity of the mutant KCNJ5 selectivity filter in the absence of the test compound, measuring the activity of the mutant KCNJ5 selectivity filter in the presence of the test compound, comparing the level of activity of the mutant KCNJ5 selectivity filter in the presence of the test compound with the level of the activity of the mutant KCNJ5 selectivity filter in the absence of the test compound, identifying the test compound as a modulator of the activity of the mutant KCNJ5 selectivity filter when the level of the activity of the mutant KCNJ5 selectivity filter in the presence of the test compound is different than level of the activity of the mutant KCNJ5 selectivity filter in the absence of the test compound. In some embodiments, where the level of activity of the mutant KCNJ5 selectivity filter is higher in the presence of the test compound, the test compound is identified as an activator. In other embodiments, where the level of the activity of the mutant KCNJ5 selectivity filter is lower in the presence of the test compound, the test compound is identified as an inhibitor. In various embodiments, the modulator is at least one of: a chemical compound, a protein, a peptide, a peptidomemetic, an antibody, a nucleic acid, an antisense nucleic acid, an shRNA, a ribozyme, or a small molecule chemical compound. In some embodiments, the mutant KCNJ5 has at least one mutation in or near the KCNJ5 selectivity filter. In another embodiment, the at least one mutation is at an amino acid residue position from about 140 to about 180 relative to SEQ ID NO:13. In other embodiments, the at least one mutation is at least one selected from the group consisting of G151X, L168X, T158X and E145X. In a further embodiment, the at least one mutation is at least one selected from the group consisting of G151A, L168R, T158A and E145Q. In one embodiment, the invention is the modulator identified using the method of identifying a modulator described herein.

In a further embodiment, the invention is a method of diagnosing a disease or disorder in a subject in need thereof, including the steps of: administering to the subject, a detectably labeled molecule that specifically binds to mutant KCNJ5, permitting the detectably labeled molecule to bind to sites in the subject where mutant KCNJ5 is present, determining the location in the subject where the detectably labeled molecule binds, and measuring the amount of detectably labeled molecule that specifically binds to mutant KCNJ5 in the subject. In some embodiments, the mutant KCNJ5 has at least one mutation selected from: G151X, L168X, T158X and E145X. In other embodiments, the mutant KCNJ5 has at least one mutation selected from: G151A, L168R, T158A and E145Q. In a preferred embodiment, the subject is human. In one embodiment, the detectably labeled molecule is an antibody. In various embodiments, the detectably labeled molecule is labeled with at least one of: biotin, avidin, 68GA, 18F, 64Cu, 86Y, 76Br, 89Zr, 111In, 124I, luciferase, and green fluorescent protein. In some embodiments, the steps of determining the location in the subject where the detectably labeled molecule binds and measuring the amount of detectably labeled molecule that specifically binds to mutant KCNJ5 in the subject uses at least one of: radiolocalization, radioimaging, magnetic resonance imaging (MRI), positron emission tomography (PET) scan, immuno-PET scan, and fluorescence imaging. In some embodiments, the disease or disorder is an adrenal disease or disorder. In particular embodiments, the adrenal disease or disorder is at least one of: aldosteronism, primary aldosteronism, secondary aldosteronism, hyperaldosteronism, primary hyperaldosteronism, secondary hyperaldosteronism, adrenal insufficiency, Addison's Disease, adrenoleukodystrophy, pheochromocytoma, Cushing's Syndrome, adrenal hyperplasia, congenital adrenal hyperplasia, cancer, adrenal cancer, hypertension, primary hypertension, secondary hypertension or virilization.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 1, comprising FIG. 1A shows sequences of blood and tumor genomic DNA and tumor cDNA of KCNJ5 codons 150 to 152 in APA12. FIG. 1B shows sequences of KCNJ5 codons 167 to 169 in APA15. FIG. 1C shows KCNJ5 mutation in kindred HPA1. At top, kindred structure is shown; affected members are shown as filled symbols; gray symbol represents a subject who died at age 36 with severe hypertension, suspected to be affected. KCNJ5 sequences of codons 157 to 159 are shown. Reverse strand traces for (A) to (C) are shown in FIG. 9. FIG. 1D depicts the conservation of G151, T158, and L168 in orthologs and paralogs. These positions are conserved among chordate orthologs that last shared a common ancestor 750 million years ago. H.s., *Homo sapiens*; M.m., *Mus musculus*; G.g., *Gallus gallus*; X.t., *Xenopus tropicalis*; D.r., *Danio rerio*; C.i., *Ciona intestinalis*. Shown below are the sequences of selected human inward rectifier K+ channels, demonstrating high conservation among diverse members of this family.

FIG. 2, comprising FIG. 2A depicts the location of mutations. The extracellular and transmembrane domains of two subunits from the channel tetramer are shown with K+ ions traversing the selectivity filter; human KCNJ5 and chicken KCNJ12 are 89% identical in the pore helix and selectivity filter. G151 lies in the selectivity filter at a position conserved among virtually all K+ channels. Its main chain carbonyl group faces the channel pore. T158 lies just above the selectivity filter, and L168 is in the second transmembrane domain (inner helix) with its side chain projecting toward the selectivity filter. FIG. 2B depicts a view of the side chains of L168 and the highly conserved Y152 of the selectivity filter, showing their close proximity. FIG. 2C depicts a view of T158, which makes hydrogen bonds with conserved positions P128 and C129.

FIG. 3, comprising FIG. 3A depicts the results of representative whole-cell recordings of 293T cells transfected with empty vector or KCNJ3 plus WT or mutant KCNJ5. The pipette holding potential was 0 mV before clamping, and the cell was clamped from −100 mV to +60 mV, with 20 mV increments. Top row: extracellular solution contained 140 mM NaCl, 5 mM KCl, 1.8 mM $MgCl_2$, 1.8 mM $CaCl_2$, 10 mM HEPES, pH 7.4; intracellular solution contained 140 mM KCl, 4 mM $MgCl_2$, 1 mM $CaCl_2$, 1 mM EGTA, 5 mM HEPES, pH 7.4. Middle row: 1 mM $BaCl_2$ was added. Bottom row: 140 mM choline chloride was substituted for extracellular NaCl. FIG. 3B depicts the current-voltage relationships from cells expressing indicated constructs (n=3 to 7 for each construct). Reversal potentials in control conditions are indicated. WT channel shows a highly negative reversal potential and is inhibited by Ba2+ but not substitution of choline for Na+ (see also FIG. 12). Mutant channels show less negative reversal potentials; currents are inhibited by elimination of Na+ but show variable inhibition by Ba2+. FIG. 3C depicts that the K+:Na+ permeability ratios calculated from the reversal potentials show loss of ion selectivity of the mutant channels. Data in FIGS. 3B and 3C are shown as mean±SEM. Reversal potentials and K+:Na+ permeability ratios are significantly different between wild-type and mutant channels (P<0.01 by Student's t test).

FIG. 4, comprising

FIG. 5 depicts protein-changing somatic mutations in aldosterone-producing adenomas. Chr, chromosome; Position, position in Human genome build 18; Ref., reference; P, significance of difference in frequency of nonreference allele between tumor and blood sequence; YY1, transcription factor yin yang 1; ZNF37, zinc finger protein 37 homolog; FZD4, frizzled 4 homolog; KCNJ5, potassium inwardly rectifying channel, subfamily J, member 5; ARHGAP9, Rho guanosine triphosphatase activating protein 9; KDM5C, lysine (K)-specific demethylase 5C; PDE9A, phosphodiesterase 9A; LRP1B, low-density lipoprotein receptor-related protein 1B. Mutations in KCNJ5 in two different tumors are shown in bold font.

FIG. 6, comprising FIG. 6A is a plot of tumor APA12 without any LOH. FIGS. 6B and 6C are plots of tumors with LOH (APA21 and APA5, respectively).

FIG. 8, comprising FIGS. 8A and 8B, depicts mutations in KCNJ5 in aldosterone-producing adenomas in Illumina sequence reads. Selected independent reads that cover the mutated positions are shown. At the top of each panel, reference amino acid and DNA sequences are shown with independent Illumina reads shown below with forward (capital) and reverse (lower cases) orientations. Base calls showing somatic mutations are highlighted. FIG. 8A shows a G151R mutation from APA12. FIG. 8B shows an L168R mutation from APA15. Complete set of independent reads at these positions are indicated in FIG. 5.

FIG. 9, comprising FIG. 9I depicts Sanger traces of a T158A mutation from kindred HPA1. Kindred ID's as in FIG. 1C.

FIGS. 10A-10D, depicts the results of experiments assessing KCNJ5 expression in adrenal glomerulosa. Human adrenal cortex was stained with anti-KCNJ5 (FIGS. 10A, 10C) or anti-Dab2 (an adrenal glomerulosa marker; (FIGS. 10B, 10D) using horseradish peroxidase-conjugated anti-rabbit secondary antibody, and sections were counterstained with hematoxylin-eosin. Low-power (FIGS. 10A, 10B) and high power views (FIGS. 10C, 10D) demonstrate staining of the glomerulosa cells in the outermost cell layers of the adrenal cortex with both anti-KCNJ5 and anti-Dab2 antibodies. 'c' denotes adrenal capsule; 'g', glomerulosa; 'f', *fasciculata*; 'r', *reticularis*. Scale bars: 100 μm.

FIG. 12, comprising (FIG. 12A) Increased KCNJ3/KCNJ5 channel activity stimulated by dopamine. KCNJ3/KCNJ5 heterotetramers are known to show increased activity in response to dopamine. Representative whole-cell recordings of 293T cells cotransfected with KCNJ3/KCNJ5WT and the dopamine D2 receptor are shown. The pipette holding potential was 0 mV before clamping, and the cell was clamped from −100 to 60 mV with 20 mV increments before (left) and after (right) addition of 1 μM dopamine. The extracellular solution contained 140 mM NaCl, 5 mM KCl, 1.8 mM MgCl2, 1.8 mM CaCl2, and 10 mM HEPES, pH 7.4, while the intracellular solution contained 140 mM KCl, 4 mM MgCl2, 1 mM CaCl2, 1 mM EGTA, and 5 mM HEPES, pH 7.4. Dopamine is seen to increase current. (FIG. 12B) Mean±SEM of current amplitudes measured at −100 mV before (control) and after addition of dopamine as in FIG. 12A (n=4). Dopamine increases current by ~50%, consistent with prior observations on KCNJ3/KCNJ5 heterotetramers. (FIG. 12C) Elimination of extracellular Na+ inhibits KCNJ3/KCNJ5G151R, but not KCNJ3/KCNJ5WT. In FIG. 3, Na+ was eliminated from the extracellular fluid by substitution for choline in the presence of Ba2+. Because Ba2+ inhibits the WT channel, it could not be assessed in this experiment whether elimination of Na+ alone had effects on the WT channel. It was also of interest to assess whether KCNJ3/KCNJ5G151R channels were inhibited by elimination of Na+ in the absence of Ba2+. Representative whole-cell recordings of 293T cells transfected with KCNJ3/KCNJ5WT or KCNJ3/KCNJ5G151R are shown. Left column: The extracellular solution contained 140 mM NaCl, 5 mM KCl, 1.8 mM MgCl2, 1.8 mM CaCl2, and 10 mM HEPES, while the intracellular solution contained 140 mM KCl, 4 mM MgCl2, 1 mM CaCl2, 1 mM EGTA, and 5 mM HEPES. Middle column: 140 mM choline chloride is substituted for extracellular NaCl. Right column: 1 mM BaCl2 was added. (FIG. 12D) Mean±SEM of current amplitudes at −100 mV from 3 cells in each condition described in (FIG. 12C). Elimination of extracellular Na+ has no effect on KCNJ3/KCNJ5WT but markedly inhibits currents in cells expressing KCNJ3/KCNJ5G151R (p<0.001, Student's t test).

FIG. 13, comprising (FIG. 13A) Representative whole-cell recordings showing K+ and Na+ currents in 293T cells transfected with KCNJ5, KCNJ5G151R, KCNJ5L168R, and KCNJ5T158A. The extracellular solution for Na+ current measurements contained 140 mM NaCl, 5 mM KCl, 1.8 mM MgCl2, 1.8 mM CaCl2, and 10 mM HEPES, pH=7.4 and the intracellular solution (pipette) was identical to the extracellular solution except for the addition of 2 mM EGTA; for K+ current measurements, the extracellular solution contained 140 mM KCl, 0.5 mM MgCl2, 1.5 mM CaCl2, and 10 mM HEPES, pH 7.4 and the intracellular solution 140 mM KCl, 4 mM MgCl2, 1 mM CaCl2, 1 mM EGTA, and 5 mM HEPES, pH 7.4. The pipette holding potential was 0 mV before clamping, and the cell was clamped from −100 to 60 mV with 20 mV increments. (FIGS. 13B, 13C) Current-voltage relationships from cells expressing the indicated constructs with symmetric high K+ or high Na+ solutions as in FIG. 13A. Addition of 1 mM BaCl2 to the extracellular fluid in FIG. 13B inhibited WT channel activity. (FIG. 13D) K+ (black) and Na+ (gray) mean current amplitudes determined at −100 mV from cells expressing WT and mutant KCNJ5 as in FIGS. 13A, 13B, demonstrating increased Na+, and decreased K+ conductance in the mutant channels (n≥3 for each condition). Relative permeabilities of K+:Na+ were determined in physiologic solutions as described in FIG. 13E. (FIG. 13E) Reversal potential of 293T cells transfected with WT or mutant KCNJ5 using physiological solutions. The extracellular solution contained 140 mM NaCl, 5 mM KCl, 1.8 mM MgCl2, 1.8 mM CaCl2, and 10 mM HEPES (pH 7.4), while the intracellular solution contained 140 mM KCl, 4 mM MgCl2, 1 mM CaCl2, 1 mM EGTA, and 5 mM HEPES (pH 7.4). The reversal potential for the homotetramers was determined by a ramp protocol ranging from −100 to +100 mV after forming a high resistance seal. The test was repeated at least twice in the same cell, and 3 cells were studied for each construct. (FIG. 13F) The K+:Na+ permeability ratio for homotetrameric WT and mutant channels was estimated from the Goldman equation: WT=23.3±1.9:1; G151R=1.0±0.1:1; L168R=1.2±0.1:1; T158A=2.7±0.1:1. These values are very similar to values from KCNJ3/KCNJ5 heterotetramers. Data in FIGS. 13B-13F are shown as mean±SEM. Reversal potentials and K+:Na+ permeability ratios are significantly different between wild-type and mutant channels (all p<0.001 by Student's t-test).

FIG. 14 is a table detailing the clinical features of 22 patients with aldosterone-producing adenomas.

FIG. 15 is a table summarizing the sequence statistics of tumor-blood pairs.

FIG. 16 is a table detailing potential somatic mutations in APAs.

FIG. 17 is a table listing the expression of K+ channels in human adrenal cortex.

FIG. 18 is a table detailing the clinical presentation of affected individuals in kindred HPA1 (adapted from (Geller et al., 2008, J Clin Endocrinol Metab 93:3117-3123).

FIG. 19 is a table detailing lesion characteristics and KCNJ5 mutation spectrum and prevalence.

FIG. 20, comprising

FIG. 21 depicts a comparison of different KCNJ5 orthologs showing high conservation of amino acid residues with mutation.

FIG. 22, comprising

FIG. 23 is a table detailing the characteristics of non-aldosterone producing lesions characteristics. No KCNJ5 mutations were found.

DETAILED DESCRIPTION OF THE INVENTION

Figure 1A:
FIGS. 1A-1D, depicts mutations in KCNJ5 in aldosterone-producing adenoma (APA) and inherited aldosteronism.
Figure 1B:
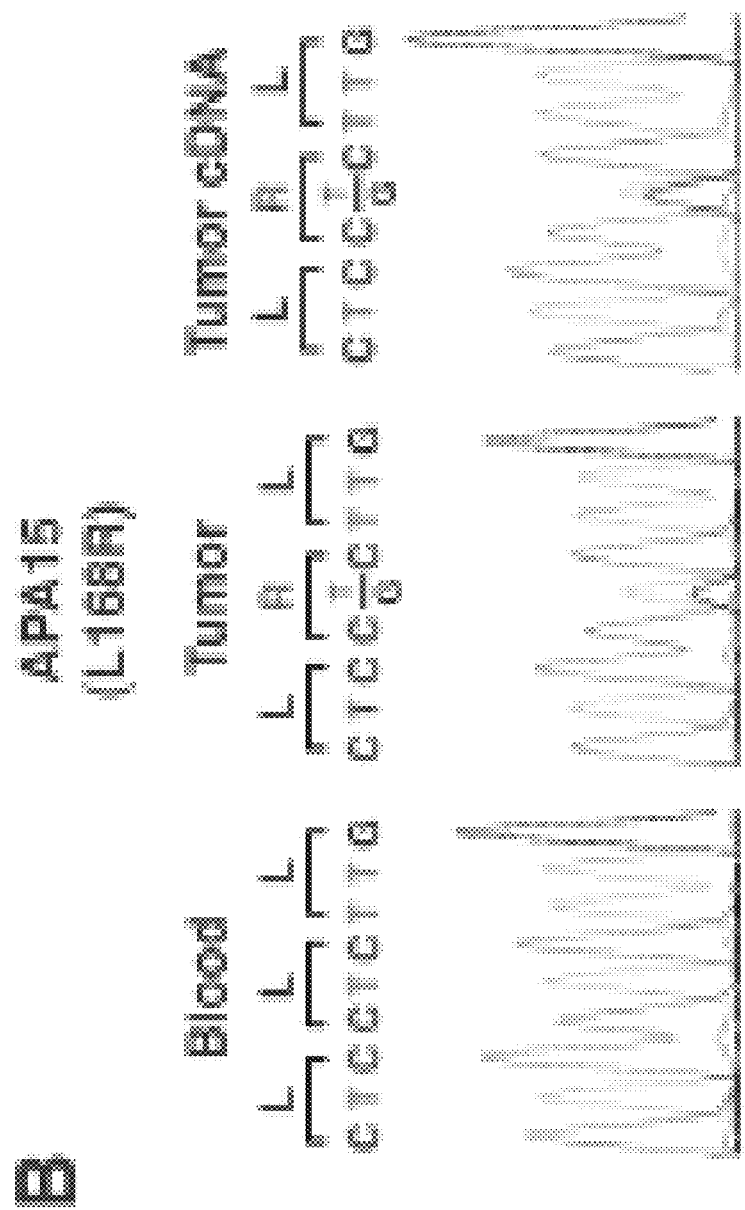

The present invention relates to the discovery that mutations in KCNJ5 are associated with adrenal diseases and disorders. The invention relates to compositions and methods useful for the assessment, characterization and treatment of an adrenal disease or disorder, based upon the presence or absence of a KCNJ5 mutation that is associated with an adrenal disease or disorder. In some embodiments, the mutation is a somatic mutation. In other embodiments, the mutation is an inherited mutation. In particular embodiments, the mutation is located in or near the selectivity filter of KCNJ5. The compositions of the invention relate to the KCNJ5 mutations associated with an adrenal disease or disorder, KCNJ5 nucleic acids having at least one mutation associated with an adrenal disease or disorder, KCNJ5 polypeptides having at least one mutation associated with an adrenal disease or disorder, and modulators of an adrenal disease or disorder. The methods of the invention relate to methods of diagnosing an adrenal disease or disorder, methods of identifying modulators of an adrenal disease or disorder, and methods of treating an adrenal disease or disorder. Examples of adrenal diseases and disorders amenable to the compositions and methods of the invention include, but are not limited to, aldosteronism, primary aldosteronism, secondary aldosteronism, hyperaldosteronism, primary hyperaldosteronism, secondary hyperaldosteronism, adrenal insufficiency, Addison's Disease, adrenoleukodystrophy, pheochromocytoma, Cushing's Syndrome, adrenal hyperplasia, congenital adrenal hyperplasia, cancer, adrenal cancer, hypertension, primary hypertension, secondary hypertension and virilization. Examples of pathologies associated with an adrenal disease or disorder amendable to the compositions and methods of the invention include, but are not limited to, hypernatremia, hypokalemia, hypocalcemia, hypomagnesemia, neoplasia, polyuria, polydipsia, heart disease, renal disease and stroke.

Definitions

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type.

An "allele" refers to one specific form of a genetic sequence (such as a gene) within a cell, an individual or within a population, the specific form differing from other forms of the same gene in the sequence of at least one, and frequently more than one, variant sites within the sequence of the gene. The sequences at these variant sites that differ between different alleles are termed "variants," "polymorphisms," or "mutations."

As used herein, to "alleviate" a disease or disorder means reducing the frequency or severity of at least one sign or symptom of a disease or disorder, such as an adrenal disease or disorder. Examples of adrenal diseases and disorders include, but are not limited to, aldosteronism, primary aldosteronism, secondary aldosteronism, hyperaldosteronism, primary hyperaldosteronism, secondary hyperaldosteronism, adrenal insufficiency, Addison's Disease, adrenoleukodystrophy, pheochromocytoma, Cushing's Syndrome, adrenal hyperplasia, congenital adrenal hyperplasia, cancer, adrenal cancer, hypertension and virilization.

As used herein the terms "alteration," "defect," "variation," or "mutation," refers to a mutation in a gene in a cell that affects the function, activity, expression (transcription or translation) or conformation of the polypeptide that it encodes. Mutations encompassed by the present invention can be any mutation of a gene in a cell that results in the enhancement or disruption of the function, activity, expression or conformation of the encoded polypeptide, including the complete absence of expression of the encoded protein and can include, for example, missense and nonsense mutations, insertions, deletions, frameshifts and premature terminations. Without being so limited, mutations encompassed by the present invention may alter splicing the mRNA (splice site mutation) or cause a shift in the reading frame (frameshift).

The term "amplification" refers to the operation by which the number of copies of a target nucleotide sequence present in a sample is multiplied.

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. The antibodies in the present invention may exist in a variety of forms including, for example, polyclonal antibodies, monoclonal antibodies, intracellular antibodies ("intrabodies"), Fv, Fab and F(ab)2, as well as single chain antibodies (scFv), heavy chain antibodies, such as camelid antibodies, and humanized antibodies (Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

As used herein, an "immunoassay" refers to any binding assay that uses an antibody capable of binding specifically to a target molecule to detect and quantify the target molecule.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

By the term "applicator," as the term is used herein, is meant any device including, but not limited to, a hypodermic syringe, a pipette, an iontophoresis device, a patch, and the like, for administering the compositions of the invention to a subject.

The term "coding sequence," as used herein, means a sequence of a nucleic acid or its complement, or a part thereof, that can be transcribed and/or translated to produce the mRNA and/or the polypeptide or a fragment thereof. Coding sequences include exons in a genomic DNA or immature primary RNA transcripts, which are joined together by the cell's biochemical machinery to provide a mature mRNA. The anti-sense strand is the complement of such a nucleic acid, and the coding sequence can be deduced therefrom. In contrast, the term "non-coding sequence," as used herein, means a sequence of a nucleic acid or its complement, or a part thereof, that is not translated into amino acid in vivo, or where tRNA does not interact to place or attempt to place an amino acid. Non-coding sequences include both intron sequences in genomic DNA or immature primary RNA transcripts, and gene-associated sequences such as promoters, enhancers, silencers, and the like.

As used herein, the term "control nucleic acid" is meant to refer to a nucleic acid (e.g., RNA, DNA) that does not come from a subject known to have, or suspected to have, a mutation in the gene of interest (e.g., for a control subject). For example, the control can be a wild type nucleic acid sequence which does not contain a variation in its nucleic acid sequence. Also, as used herein, a control nucleic acid can be a fragment or portion of gene that does not include the defect/variation that is the mutation of interest (that is, the mutation to be detected in an assay).

As used herein, the terms "complementary" or "complementarity" are used in reference to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

As used herein, the term "diagnosis" refers to the determination of the nature of a case of disease or disorder. In some embodiments of the present invention, methods for making a diagnosis are provided which permit determination of a particular mutation associated with an adrenal disease or disorder. Examples of adrenal diseases and disorders include, but are not limited to, aldosteronism, primary aldosteronism, secondary aldosteronism, hyperaldosteronism, primary hyperaldosteronism, secondary hyperaldosteronism, adrenal insufficiency, Addison's Disease, adrenoleukodystrophy, pheochromocytoma, Cushing's Syndrome, adrenal hyperplasia, congenital adrenal hyperplasia, cancer, adrenal cancer, hypertension, primary hypertension, secondary hypertension and virilization.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

An "effective amount" as used herein, means an amount which provides a therapeutic or prophylactic benefit.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein, the term "fragment," as applied to a nucleic acid, refers to a subsequence of a larger nucleic acid. A "fragment" of a nucleic acid can be at least about 15 nucleotides in length; for example, at least about 50 nucleotides to about 100 nucleotides; at least about 100 to about 500 nucleotides, at least about 500 to about 1000 nucleotides; at least about 1000 nucleotides to about 1500 nucleotides; about 1500 nucleotides to about 2500 nucleotides; or about 2500 nucleotides (and any integer value in between). As used herein, the term "fragment," as applied to a protein or peptide, refers to a subsequence of a larger protein or peptide. A "fragment" of a protein or peptide can be at least about 20 amino acids in length; for example, at least about 50 amino acids in length; at least about 100 amino acids in length; at least about 200 amino acids in length; at least about 300 amino acids in length; or at least about 400 amino acids in length (and any integer value in between).

The term "gene" refers to a nucleic acid (e.g., DNA) sequence that includes coding sequences necessary for the production of a polypeptide, precursor, or RNA (e.g., mRNA). The polypeptide may be encoded by a full length coding sequence or by any portion of the coding sequence so long as the desired activity or functional property (e.g., enzymatic activity, ligand binding, signal transduction, immunogenicity, etc.) of the full-length or fragment is retained. The term also encompasses the coding region of a structural gene and the sequences located adjacent to the coding region on both the 5' and 3' ends for a distance of about 2 kb or more on either end such that the gene corresponds to the length of the full-length mRNA and 5' regulatory sequences which influence the transcriptional properties of the gene. Sequences located 5' of the coding region and present on the mRNA are referred to as 5'-untranslated sequences. The 5'-untranslated sequences usually contain the regulatory sequences. Sequences located 3' or downstream of the coding region and present on the mRNA are referred to as 3'-untranslated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

A "genome" is all the genetic material of an organism. In some instances, the term genome may refer to the chromosomal DNA. Genome may be multichromosomal such that the DNA is cellularly distributed among a plurality of individual chromosomes. For example, in human there are 22 pairs of chromosomes plus a gender associated XX or XY pair. DNA derived from the genetic material in the chromosomes of a particular organism is genomic DNA. The term genome may also refer to genetic materials from organisms that do not have chromosomal structure. In addition, the term genome may refer to mitochondria DNA. A genomic library is a collection of DNA fragments representing the whole or a portion of a genome. Frequently, a genomic library is a collection of clones made from a set of randomly generated, sometimes overlapping DNA fragments representing the entire genome or a portion of the genome of an organism.

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared X 100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

The term "housekeeping gene" as used herein refers to genes that are generally always expressed and thought to be involved in routine cellular metabolism. Housekeeping genes are well known and include such genes as glyceraldehyde-3-phosphate dehydrogenase (G3PDH or GAPDH), albumin, actins, tubulins, cyclophilin, hypoxanthine phsophoribosyltransferase (HRPT), 28S, and 18S rRNAs and the like.

As used herein, the term "hybridization" is used in reference to the pairing of complementary nucleic acids. Hybridization and the strength of hybridization (i.e., the strength of the association between the nucleic acids) is impacted by such factors as the degree of complementarity between the nucleic acids, stringency of the conditions involved, the $T_m$ of the formed hybrid, and the G:C ratio within the nucleic acids. A single molecule that contains pairing of complementary nucleic acids within its structure is said to be "self-hybridized." A single DNA molecule with internal complementarity could assume a variety of secondary structures including loops, kinks or, for long stretches of base pairs, coils.

"Instructional material," as that term is used herein, includes a publication, a recording, a diagram, or any other medium of expression which can be used to communicate the usefulness of the nucleic acid, peptide, and/or compound of the invention in the kit for identifying, diagnosing or alleviating or treating the various diseases or disorders recited herein. Optionally, or alternately, the instructional material may describe one or more methods of identifying, diagnosing or alleviating the diseases or disorders in a cell or a tissue of a subject. The instructional material of the kit may, for example, be affixed to a container that contains the nucleic acid, peptide, and/or compound of the invention or be shipped together with a container that contains the nucleic acid, peptide, and/or compound. Alternatively, the instructional material may be shipped separately from the container with the intention that the recipient uses the instructional material and the compound cooperatively.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

The term "label" when used herein refers to a detectable compound or composition that is conjugated directly or indirectly to a probe to generate a "labeled" probe. The label may be detectable by itself (e.g. radioisotope labels or fluorescent labels) or, in the case of an enzymatic label, may catalyze chemical alteration of a substrate compound or composition that is detectable (e.g., avidin-biotin). In some instances, primers can be labeled to detect a PCR product.

The terms "microarray" and "array" refers broadly to both "DNA microarrays" and "DNA chip(s)," and encompasses all art-recognized solid supports, and all art-recognized methods for affixing nucleic acid molecules thereto or for synthesis of nucleic acids thereon. Preferred arrays typically comprise a plurality of different nucleic acid probes that are coupled to a surface of a substrate in different, known locations. These arrays, also described as "microarrays" or colloquially "chips" have been generally described in the art, for example, U.S. Pat. Nos. 5,143,854, 5,445,934, 5,744,305, 5,677,195, 5,800,992, 6,040,193, 5,424,186 and Fodor et al., 1991, Science, 251:767-777, each of which is incorporated by reference in its entirety for all purposes. Arrays may generally be produced using a variety of techniques, such as mechanical synthesis methods or light directed synthesis methods that incorporate a combination of photolithographic methods and solid phase synthesis methods. Techniques for the synthesis of these arrays using mechanical synthesis methods are described in, e.g., U.S. Pat. Nos. 5,384,261, and 6,040,193, which are incorporated herein by reference in their entirety for all purposes. Although a planar array surface is preferred, the array may be fabricated on a surface of virtually any shape or even a multiplicity of surfaces. Arrays may be nucleic acids on beads, gels, polymeric surfaces, fibers such as fiber optics, glass or any other appropriate substrate. (See U.S. Pat. Nos. 5,770,358, 5,789,162, 5,708,153, 6,040,193 and 5,800,992, which are hereby incorporated by reference in their entirety for all purposes.) Arrays may be packaged in such a manner as to allow for diagnostic use or can be an all-inclusive device; e.g., U.S. Pat. Nos. 5,856,174 and 5,922,591 incorporated in their entirety by reference for all purposes. Arrays are commercially available from, for example, Affymetrix (Santa Clara, Calif.) and Applied Biosystems (Foster City, Calif.), and are directed to a variety of purposes, including genotyping, diagnostics, mutation analysis, marker expression, and gene expression monitoring for a variety of eukaryotic and prokaryotic organisms. The number of probes on a solid support may be varied by changing the size of the individual features. In one embodiment the feature size is 20 by 25 microns square, in other embodiments features may be, for example, 8 by 8, 5 by 5 or 3 by 3 microns square, resulting in about 2,600,000, 6,600,000 or 18,000,000 individual probe features.

Assays for amplification of the known sequence are also disclosed. For example primers for PCR may be designed to amplify regions of the sequence. For RNA, a first reverse transcriptase step may be used to generate double stranded DNA from the single stranded RNA. The array may be designed to detect sequences from an entire genome; or one or more regions of a genome, for example, selected regions of a genome such as those coding for a protein or RNA of interest; or a conserved region from multiple genomes; or multiple genomes, Arrays and methods of genetic analysis using arrays is described in Cutler, et al., 2001, Genome Res. 11(11): 1913-1925 and Warrington, et al., 2002, Hum Mutat 19:402-409 and in U.S. Patent Pub No 20030124539, each of which is incorporated herein by reference in its entirety.

By the term "modulating," as used herein, is meant mediating a detectable increase or decrease in the level or activity of a molecule, or in the response in a subject, compared with the level or activity of a molecule, or in the response in the subject, in the absence of a treatment or compound, and/or compared with the level or activity of an otherwise identical but untreated molecule or of a response in an otherwise identical but untreated subject. The term encompasses perturbing and/or affecting a native signal or response thereby mediating a beneficial therapeutic response in a subject, preferably, a human.

A "mutation," as used herein, refers to a change in nucleic acid or polypeptide sequence relative to a reference sequence (which is preferably a naturally-occurring normal or "wild-type" sequence), and includes translocations, deletions, insertions, and substitutions/point mutations. A "mutant" as used herein, refers to either a nucleic acid or polypeptide comprising a mutation.

"Neoplasia" as used herein, refers to the abnormal proliferation of benign or malignant cells. The growth of neoplastic cells exceeds and/or is not coordinated with that of the normal tissues around it.

A "nucleic acid" refers to a polynucleotide and includes poly-ribonucleotides and poly-deoxyribonucleotides. Nucleic acids according to the present invention may include any polymer or oligomer of pyrimidine and purine bases, preferably cytosine, thymine, and uracil, and adenine and guanine, respectively. (See Albert L. Lehninger, Principles of Biochemistry, at 793-800 (Worth Pub. 1982) which is herein incorporated in its entirety for all purposes). Indeed, the present invention contemplates any deoxyribonucleotide, ribonucleotide or peptide nucleic acid component, and any chemical variants thereof, such as methylated, hydroxymethylated or glucosylated forms of these bases, and the like. The polymers or oligomers may be heterogeneous or homogeneous in composition, and may be isolated from naturally occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

An "oligonucleotide" or "polynucleotide" is a nucleic acid ranging from at least 2, preferably at least 8, 15 or 25 nucleotides in length, but may be up to 50, 100, 1000, or 5000 nucleotides long or a compound that specifically hybridizes to a polynucleotide. Polynucleotides include sequences of deoxyribonucleic acid (DNA) or ribonucleic acid (RNA) or mimetics thereof which may be isolated from natural sources, recombinantly produced or artificially synthesized. A further example of a polynucleotide of the present invention may be a peptide nucleic acid (PNA). (See U.S. Pat. No. 6,156,501 which is hereby incorporated by reference in its entirety.) The invention also encompasses situations in which there is a nontraditional base pairing such as Hoogsteen base pairing which has been identified in certain tRNA molecules and postulated to exist in a triple helix. "Polynucleotide" and "oligonucleotide" are used interchangeably in this disclosure. It will be understood that when a nucleotide sequence is represented herein by a DNA sequence (e.g., A, T, G, and C), this also includes the corresponding RNA sequence (e.g., A, U, G, C) in which "U" replaces "T".

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

As used herein, the term "polymerase chain reaction" ("PCR") refers to the method of K. B. Mullis (U.S. Pat. Nos. 4,683,195 4,683,202, and 4,965,188, hereby incorporated by reference), which describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified". As used herein, the terms "PCR product," "PCR fragment," "amplification product" or "amplicon" refer to the resultant mixture of compounds after two or more cycles of the PCR steps of denaturation, annealing and extension are complete. These terms encompass the case where there has been amplification of one or more segments of one or more target sequences.

As used herein, the term "probe" refers to an oligonucleotide (i.e., a sequence of nucleotides), whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification and isolation of particular gene sequences.

The term "perfect match," "match," "perfect match probe" or "perfect match control" refers to a nucleic acid that has a sequence that is perfectly complementary to a particular target sequence. The nucleic acid is typically perfectly complementary to a portion (subsequence) of the target sequence. A perfect match (PM) probe can be a "test probe", a "normalization control" probe, an expression level control probe and the like. A perfect match control or perfect match is, however, distinguished from a "mismatch" or "mismatch probe." The term "mismatch," "mismatch control" or "mismatch probe" refers to a nucleic acid whose sequence is not perfectly complementary to a particular target sequence. As a non-limiting example, for each mismatch (MM) control in a high-density probe array there typically exists a corresponding perfect match (PM) probe that is perfectly complementary to the same particular target sequence. The mismatch may comprise one or more bases. While the mismatch(es) may be located anywhere in the mismatch probe, terminal mismatches are less desirable because a terminal mismatch is less likely to prevent hybridization of the target sequence. In a particularly preferred embodiment, the mismatch is located at or near the center of the probe such that the mismatch is most likely to destabilize the duplex with the target sequence under the test hybridization conditions.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

As used herein, "polynucleotide" includes cDNA, RNA, DNA/RNA hybrid, antisense RNA, ribozyme, genomic DNA, synthetic forms, and mixed polymers, both sense and antisense strands, and may be chemically or biochemically modified to contain non-natural or derivatized, synthetic, or semi-synthetic nucleotide bases. Also, contemplated are alterations of a wild type or synthetic gene, including but not limited to deletion, insertion, substitution of one or more nucleotides, or fusion to other polynucleotide sequences.

The term "primer" refers to an oligonucleotide capable of acting as a point of initiation of synthesis along a complementary strand when conditions are suitable for synthesis of a primer extension product. The synthesizing conditions include the presence of four different deoxyribonucleotide triphosphates and at least one polymerization-inducing agent such as reverse transcriptase or DNA polymerase. These are present in a suitable buffer, which may include constituents which are co-factors or which affect conditions such as pH and the like at various suitable temperatures. A primer is preferably a single strand sequence, such that amplification efficiency is optimized, but double stranded sequences can be utilized.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

The term "reaction mixture" or "PCR reaction mixture" or "master mix" or "master mixture" refers to an aqueous solution of constituents in a PCR reaction that can be constant across different reactions. An exemplary PCR reaction mixture includes buffer, a mixture of deoxyribonucleoside triphosphates, primers, probes, and DNA polymerase. Generally, template RNA or DNA is the variable in a PCR.

"Sample" or "biological sample" as used herein means a biological material isolated from a subject. The biological sample may contain any biological material suitable for detecting mutant KCNJ5, and may comprise fluid, cellular and/or non-cellular material obtained from the individual.

A "somatic mutation," as used herein, is a genetic alteration acquired by a somatic cell that can be passed on to progeny cells of the mutated somatic cell in the course of cell division. Somatic mutations differ from germ line mutations, which are inherited genetic alterations that occur in germ cells.

As used herein the term "stringency" is used in reference to the conditions of temperature, ionic strength, and the presence of other compounds such as organic solvents, under which nucleic acid hybridizations are conducted.

Under "low stringency conditions" a nucleic acid sequence of interest will hybridize to its exact complement, sequences with single base mismatches, closely related sequences (e.g., sequences with 90% or greater homology), and sequences having only partial homology (e.g., sequences with 50-90% homology). Under "medium stringency conditions," a nucleic acid sequence of interest will hybridize only to its exact complement, sequences with single base mismatches, and closely related sequences (e.g., 90% or greater homology). Under "high stringency conditions," a nucleic acid sequence of interest will hybridize only to its exact complement, and (depending on conditions such a temperature) sequences with single base mismatches. In other words, under conditions of high stringency the temperature can be raised so as to exclude hybridization to sequences with single base mismatches.

As used herein, "substantially purified" refers to being essentially free of other components. For example, a substantially purified cell is a cell which has been separated from other cell types with which it is normally associated in its naturally occurring state. In some instances, a population of substantially purified cells refers to a homogenous population of cells. In other instances, this term refers simply to a cell that have been separated from the cells with which they are naturally associated in their natural state.

The term "target" as used herein refers to a molecule that has an affinity for a given probe. Targets may be naturally-occurring or man-made molecules. Also, they can be employed in their unaltered state or as aggregates with other species. Targets may be attached, covalently or noncovalently, to a binding member, either directly or via a specific binding substance. Targets are sometimes referred to in the art as anti-probes. As the term target is used herein, no difference in meaning is intended.

As used herein, the terms "therapy" or "therapeutic regimen" refer to those medical steps taken to alleviate or alter a disorder or disease state, e.g., a course of treatment intended to reduce or eliminate the affects or symptoms of a disease using pharmacological, surgical, dietary and/or other techniques. A therapeutic regimen may include a prescribed dosage of one or more drugs or surgery. Therapies will most often be beneficial and reduce the disorder or disease state but in many instances the effect of a therapy will have non-desirable or side-effects. The effect of therapy will also be impacted by the physiological state of the host, e.g., age, gender, genetics, weight, other disease conditions, etc.

The term "therapeutically effective amount" refers to the amount of the subject compound that will elicit the biological or medical response of a tissue, system, or subject that is being sought by the researcher, veterinarian, medical doctor or other clinician. The term "therapeutically effective amount" includes that amount of a compound that, when administered, is sufficient to prevent development of, or alleviate to some extent, one or more of the signs or symptoms of the disorder or disease being treated. The therapeutically effective amount will vary depending on the compound, the disease and its severity and the age, weight, etc., of the subject to be treated.

To "treat" a disease as the term is used herein, means to reduce the frequency or severity of at least one sign or symptom of a disease or disorder experienced by a subject.

As used herein, the term "wild-type" refers to a gene or gene product isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product that displays modifications in sequence and/or functional properties (i.e., altered characteristics) when compared to the wild-type gene or gene product. It is noted that naturally occurring mutants can be isolated; these are identified by the fact that they have altered characteristics (including altered nucleic acid sequences) when compared to the wild-type gene or gene product.

Description

The present invention relates to the discovery that mutations in KCNJ5 are associated with adrenal diseases and disorders. The invention relates to compositions and methods useful for the assessment, characterization and treatment of an adrenal disease and disorder, based upon the presence or absence of KCNJ5 mutations that are associated with an adrenal disease and disorder. In some embodiments, the mutations are somatic mutations. In other embodiments, the mutations are inherited mutations. In particular embodiments, the mutation is located in or near the selectivity filter region of KCNJ5. In some embodiments, the adrenal disease or disorder is at least one selected from the group consisting of aldosteronism, primary aldosteronism, secondary aldosteronism, hyperaldosteronism, primary hyperaldosteronism, secondary hyperaldosteronism, adrenal insufficiency, Addison's Disease, adrenoleukodystrophy, pheochromocytoma, Cushing's Syndrome, adrenal hyperplasia, congenital adrenal hyperplasia, cancer, adrenal cancer, hypertension, primary hypertension, secondary hypertension and virilization. In one embodiment, the primary aldosteronism is associated with APA. In another embodiment, the primary aldosteronism is idiopathic.

In various embodiments, the compositions of the invention relate to KCNJ5 mutations associated with an adrenal disease or disorder, KCNJ5 nucleic acids having at least one mutation associated with an adrenal disease or disorder, KCNJ5 polypeptides having at least one mutation associated with an adrenal disease or disorder, and modulators of an adrenal disease or disorder. In other various embodiments, the methods of the invention relate to methods of diagnosing an adrenal disease or disorder, methods of characterizing an adrenal disease or disorder, methods of identifying modulators of an adrenal disease or disorder, methods of treating an adrenal disease or disorder, and methods of treating pathologies associated with an adrenal disease or disorder. In various embodiments, the adrenal disease or disorder is at least one selected from the group consisting of aldosteronism, primary aldosteronism, secondary aldosteronism, hyperaldosteronism, primary hyperaldosteronism, secondary hyperaldosteronism, adrenal insufficiency, Addison's Disease, adrenoleukodystrophy, pheochromocytoma, Cushing's Syndrome, adrenal hyperplasia, congenital adrenal hyperplasia, cancer, adrenal cancer, hypertension, primary hypertension, secondary hypertension and virilization.

In a particular embodiment of the compositions and methods of the invention described herein, the mutant polypeptide associated with an adrenal disease or disorder is mutant KCNJ5 G151X, which is a KCNJ5 polypeptide comprising at least one mutation at amino acid residue position 151, where is G is replaced by another amino acid residue. In another embodiment of the compositions and methods of the invention described herein, the mutant polypeptide associated with an adrenal disease or disorder is mutant KCNJ5 L168X, which is a KCNJ5 polypeptide comprising at least one mutation at amino acid residue position 168, where is L is replaced by another amino acid residue. In yet another embodiment of the compositions and methods of the invention described herein, the mutant polypeptide associated with an adrenal disease or disorder is mutant KCNJ5 T158X, which is a KCNJ5 polypeptide comprising at least one mutation at amino acid residue position 158, where is T is replaced by another amino acid residue. In a further embodiment of the compositions and methods of the invention described herein, the mutant polypeptide associated with an adrenal disease or disorder is mutant KCNJ5 E145X, which is a KCNJ5 polypeptide comprising at least one mutation at amino acid residue position 145, where is E is replaced by another amino acid residue.

Assays

The present invention relates to the discovery that mutations are associated with the development and progression of adrenal diseases and disorders. In various embodiments, the invention relates to a genetic screening assay of a subject to determine whether the subject has a KCNJ5 mutation associated with an adrenal disease or disorder. The present invention provides methods of assessing for the presence or absence of a KCNJ5 mutation associated with an adrenal disease or disorder, as well as methods of diagnosing a subject having a mutation associated with an adrenal disease or disorder. In some embodiments, the diagnostic assays described herein are in vitro assays. In other embodiments, the diagnostic assays described herein are in vivo assays. In some embodiments of the invention, the adrenal disease or disorder is associated with APA. In other embodiments of the invention, the adrenal disease or disorder is idiopathic. The mutations associated with an adrenal disease or disorder described herein include alterations (e.g., substitution, deletion, insertion, or transition) in the nucleic acid sequence of KCNJ5, as elsewhere described herein throughout. The positions of the mutations in the gene sequences described herein are numbered in relation to the nucleic acid sequence or amino acid sequence. That is, the numbered position of an altered nucleotide, or amino acid, is the position number of that nucleotide, or amino acid, in the nucleic acid or amino acid sequence.

In one embodiment, the method of the invention is a diagnostic assay for diagnosing an adrenal disease or disorder in a subject in need thereof, by determining whether a mutation is present KCNJ5 in a biological sample obtained from the subject. The results of the diagnostic assay can be used alone, or in combination with other information from the subject, or from the biological sample obtained from the subject. In some embodiments, the diagnostic assay of the invention is an in vitro assay. In other embodiments, the diagnostic assay of the invention is an in vivo assay. The mutation identified by the assay can be any mutation in KCNJ5 that is associated with an adrenal disease or disorder. In some embodiments, the KCNJ5 mutation is at least one of G151X, L168X, T158X, or E145X. In other embodiments, the KCNJ5 mutation is at least one of G151A, L168R, T158A, or E145Q.

In the assay methods of the invention, a test biological sample from a subject is assessed for the presence of at least one mutation in at least one gene associated with an adrenal disease or disorder. The test biological sample can be an in vitro sample or an in vivo sample. In various embodiments, the subject is a human subject, and may be of any race, sex and age. Representative subjects include those who are suspected of having an adrenal disease or disorder, those who have been diagnosed with an adrenal disease or disorder, those whose have an adrenal disease or disorder, those who have had an adrenal disease or disorder, those who at risk of a recurrence of an adrenal disease or disorder, and those who are at risk of developing an adrenal disease or disorder.

In some embodiments, a KCNJ5-binding molecule is used in vivo for the diagnosis of an adrenal disease or disorder. In other embodiments, a mutant KCNJ5-binding molecule is used in vivo for the diagnosis of an adrenal disease or disorder. In a further embodiment, a combination of a KCNJ5-binding molecule and a mutant KCNJ5-binding molecule is used in vivo for the diagnosis of an adrenal disease of disorder. In some embodiments, the KCNJ5-binding molecule is an antibody that specifically binds to KCNJ5. In other embodiments, the mutant KCNJ5-binding molecule is an antibody that specifically binds to mutant KCNJ5. In various embodiments, the KCNJ5-binding molecule, or the mutant KCNJ5-binding molecule, or both the KNCJ5-binding and mutant KCNJ5-binding molecule are detectably labeled. In some embodiments, a specifically binding KCNJ5-binding molecule is administered to a subject for a sufficient amount of time to allow the KCNJ5-binding molecule to localize to the sites (e.g., tissues, cells, fluids, etc.) in the subject where KCNJ5 is present. In other embodiments, a specifically binding mutant KCNJ5-binding molecule is administered to a subject for a sufficient amount of time to allow the mutant KCNJ5-binding molecule to localize to the sites (e.g., tissues, cells, fluids, etc.) in the subject where mutant KCNJ5 is present. The binding of the specifically-binding molecule, or specifically binding molecules, is then detected by various imaging methods, for example, by radiolocalization, radioimaging, magnetic resonance imaging (MRI), positron emission tomography (PET) scan, immuno-PET scan, and fluorescence imaging, by using, for example, a detectibly labeled KCNJ5-binding molecule, or a detectibly labeled mutant KCNJ5-binding molecule, or a combination thereof. When a combination of more than one specifically binding molecule is used, the ratio of the binding of the more than one specifically binding molecule can be determined and the ratio can be used as information for diagnosis. These imaging methods include MRI (for example, but not limited to, using a biotinylated antibody and avidin-iron oxide), PET (for example, but not limited to, using an antibody labeled with $^{68}$GA, $^{18}$F, $^{64}$Cu, $^{86}$Y, $^{76}$Br, $^{89}$Zr, $^{111}$In, or $^{124}$I), and optical imaging (for example, but not limited to, using luciferase or green fluorescent protein labeled antibodies). Examples of labeling and imaging assays useful with the compositions and methods of the invention include those described in Wu (2009, J. Nuclear Medicine 50:2-5), Valk et al. (2006, Positron Emission Tomography: Clinical Practice, Springer), Reilly (2010, Monoclonal Antibody and Peptide-Targeted Radiotherapy of Cancer, John Wiley and Sons), Schiepers and Allen-Auerbach (2006, Diagnostic Nuclear Medicine, Birkhauser), Kontermann (2010, Antibody Engineering, Springer), and Vallabhajosula (2009, Molecular Imaging: Radiopharmaceuticals for PET and SPECT, Springer).

In other embodiments, a KCNJ5-binding molecule is used in vivo for the detection of a mutation in KCNJ5. In other embodiments, a mutant KCNJ5-binding molecule is used in vivo for the detection of a mutation in KCNJ5. In a further embodiment, a combination of a KCNJ5-binding molecule and a mutant KCNJ5-binding molecule is used in vivo for the detection of a mutation in KCNJ5. In some embodiments, the KCNJ5-binding molecule is an antibody that specifically binds to KCNJ5. In other embodiments, the mutant KCNJ5-binding molecule is an antibody that specifically binds to mutant KCNJ5. In various embodiments, the KCNJ5-binding molecule, or the mutant KCNJ5-binding molecule, or both the KNCJ5-binding and mutant KCNJ5-binding molecule are detectably labeled. In some embodiments, a specifically binding KCNJ5-binding molecule is administered to a subject for a sufficient amount of time to allow the KCNJ5-binding molecule to localize to the sites (e.g., tissues, cells, fluids, etc.) in the subject where KCNJ5 is present. In other embodiments, a specifically binding mutant KCNJ5-binding molecule is administered to a subject for a sufficient amount of time to allow the mutant KCNJ5-binding molecule to localize to the sites (e.g., tissues, cells, fluids, etc.) in the subject where mutant KCNJ5 is present. The binding of the specifically-binding molecule, or specifically binding molecules, is then detected by various imaging methods, for example, by radiolocalization, radioimaging, magnetic resonance imaging (MRI), positron emission tomography (PET) scan, immuno-PET scan, and fluorescence imaging, by using, for example, a detectibly labeled KCNJ5-binding molecule, or a detectibly labeled mutant KCNJ5-binding molecule, or a combination thereof. When a combination of more than one specifically binding molecule is used, the ratio of the binding of the more than one specifically binding molecule can be determined and the ratio can be used as information for the detection of a mutation in KCNJ5. These imaging methods include MRI (for example, but not limited to, using a biotinylated antibody and avidin-iron oxide), PET (for example, but not limited to, using an antibody labeled with $^{68}$GA, $^{18}$F, $^{64}$Cu, $^{86}$Y, $^{76}$Br, $^{89}$Zr, $^{111}$In, or $^{124}$I), and optical imaging (for example, but not limited to, using luciferase or green fluorescent protein labeled antibodies).

In one embodiment, the test sample is a sample containing at least a fragment of a KCNJ5 nucleic acid or KCNJ5 polypeptide. The term, "fragment," as used herein, indicates that the portion of the polypeptide or nucleic acid (e.g., DNA, mRNA or cDNA) that is sufficient to identify it as a fragment of KCNJ5, or mutant KCNJ5. In one representative embodiment, a fragment comprises one or more exons of KCNJ5, or mutant KCNJ5. In another representative embodiment, a fragment comprises part of an exon of KCNJ5, or mutant KCNJ5. In some embodiments, the fragment can also include an intron/exon junction of KCNJ5, or KCNJ5.

In some embodiments, the test sample is prepared from a biological sample obtained from the subject. The biological sample can be a sample from any source which contains KCNJ5 polypeptide or KCNJ5 nucleic acid (e.g., DNA, chromosomal nucleic acid, or RNA), such as a body fluid (e.g., blood, plasma, serum, etc.), or a tissue, or a tumor, or a cell, or a combination thereof. A biological sample can be obtained by appropriate methods, such as, by way of examples, biopsy or fluid draw. In certain embodiments, a biological sample containing genomic DNA is used. The biological sample can be used as the test sample; alternatively, the biological sample can be processed to enhance access to polypeptides, nucleic acids, or copies of nucleic acids (e.g., copies of nucleic acids comprising a mutation associated with an adrenal disease or disorder), and the processed biological sample can then be used as the test sample. For example, in various embodiments, nucleic acid (e.g., genomic DNA or cDNA prepared from mRNA) is prepared from a biological sample, for use in the methods. Alternatively or in addition, if desired, an amplification method can be used to amplify nucleic acids comprising all or a fragment of an mRNA or genomic DNA in a biological sample, for use as the test sample in the assessment for the presence or absence of a KCNJ5 mutation associated with an adrenal disease or disorder.

The test sample is assessed to determine whether one or more KCNJ5 mutations are present in the polypeptide or nucleic acid of the subject. In general, detecting a mutation may be carried out by determining the presence or absence of a polypeptide or nucleic acid containing a mutation of interest in the test sample. In one embodiment, the mutant KCNJ5 polypeptide has an amino acid sequence comprising at least one mutation in or near the KCNJ5 selectivity filter. In another embodiment, the mutant KCNJ5 polypeptide has an amino acid comprising at least one mutation at amino acid residue position from about 140 to about 180 relative to SEQ ID NO:13. In some particular embodiments, the KCNJ5 mutation is at least one of G151X, L168X, T158X, or E145X. In other particular embodiments, the KCNJ5 mutation is at least one of G151A, L168R, T158A, or E145Q. In further embodiments, the compositions of the invention comprise a nucleic acid encoding a mutant KCNJ5 polypeptide.

In various embodiments of the invention, methods of detecting mutant KCNJ5 polypeptide include, but are not limited to, an immunochromatography assay, an immunodot assay, a Luminex assay, an ELISA assay, an ELISPOT assay, a protein microarray assay, a ligand-receptor binding assay, displacement of a ligand from a receptor assay, an immunostaining assay, a Western blot assay, a mass spectrophotometry assay, a radioimmunoassay (RIA), a radioimmunodiffusion assay, a liquid chromatography-tandem mass spectrometry assay, an ouchterlony immunodiffusion assay, reverse phase protein microarray, a rocket immunoelectrophoresis assay, an immunohistostaining assay, an immunoprecipitation assay, a complement fixation assay, a FACS assay, an enzyme-substrate binding assay, an enzymatic assay, an enzymatic assay employing a detectable molecule, such as a chromophore, fluorophore, or radioactive substrate, and a protein chip assay (see also, 2007, Van Emon, Immunoassay and Other Bioanalytical Techniques, CRC Press; 2005, Wild, Immunoassay Handbook, Gulf Professional Publishing; 1996, Diamandis and Christopoulos, Immunoassay, Academic Press; 2005, Joos, Microarrays in Clinical Diagnosis, Humana Press; 2005, Hamdan and Righetti, Proteomics Today, John Wiley and Sons; 2007).

In some embodiments, hybridization methods, such as Southern analysis, Northern analysis, or in situ hybridizations, can be used (see Current Protocols in Molecular Biology, Ausubel, F. et al., eds., John Wiley & Sons, including all supplements). For example, the presence of a KCNJ5 mutation can be indicated by hybridization of nucleic acid in the genomic DNA, RNA, or cDNA to a nucleic acid probe. A "nucleic acid probe", as used herein, can be a DNA probe or an RNA probe; the nucleic acid probe can contain at least one polymorphism of interest, as described herein. The probe can be, for example, the gene, a gene fragment (e.g., one or more exons), a vector comprising the gene, a probe or primer, etc. For representative examples of use of nucleic acid probes, see, for example, U.S. Pat. Nos. 5,288,611 and 4,851,330.

To detect one or more KCNJ5 mutations of interest, a hybridization sample is formed by contacting the test sample with at least one nucleic acid probe. A preferred probe for detecting mRNA or genomic DNA is a labeled nucleic acid probe capable of hybridizing to mRNA, cDNA or genomic DNA of KCNJ5. The nucleic acid probe can be, for example, a full-length nucleic acid molecule, or a portion thereof, such as an oligonucleotide of at least 15, 30, 50, 100, 250 or 500 nucleotides in length and sufficient to specifically hybridize under stringent conditions to appropriate target mRNA, cDNA or genomic DNA. The hybridization sample is maintained under conditions which are sufficient to allow specific hybridization of the nucleic acid probe to mRNA, cDNA or genomic DNA of KCNJ5. Specific hybridization can be performed under high stringency conditions or moderate stringency conditions, as appropriate. In a preferred embodiment, the hybridization conditions for specific hybridization are high stringency. Specific hybridization, if present, is then detected using standard methods. If specific hybridization occurs between the nucleic acid probe having a mutant sequence and a gene, mRNA or cDNA in the test sample, the mutation that is present in the nucleic acid probe is also present in the nucleic acid sequence of the subject. More than one nucleic acid probe can also be used concurrently in this method. Specific hybridization of any one of the nucleic acid probes is indicative of the presence of the mutation of interest, as described herein.

In Northern analysis (see Current Protocols in Molecular Biology, Ausubel, F. et al., eds., John Wiley & Sons, supra), the hybridization methods described above are used to identify the presence of a KCNJ5 mutation of interest in an RNA, such as a mRNA. For Northern analysis, a test sample comprising RNA is prepared from a biological sample from the subject by appropriate means. Specific hybridization of a nucleic acid probe, as described above, to RNA from the subject is indicative of the presence of a KCNJ5 mutation of interest, as described herein.

Alternatively, a peptide nucleic acid (PNA) probe can be used instead of a nucleic acid probe in the hybridization methods described herein. PNA is a DNA mimic having a peptide-like, inorganic backbone, such as N-(2-aminoethyl) glycine units, with an organic base (A, G, C, T or U) attached to the glycine nitrogen via a methylene carbonyl linker (see, for example, 1994, Nielsen et al., Bioconjugate Chemistry 5:1). The PNA probe can be designed to specifically hybridize to a nucleic acid sequence comprising one or more mutations of interest. Hybridization of the PNA probe to a nucleic acid sequence is indicative of the presence of the KCNJ5 mutation of interest.

In another embodiment of the methods of the invention, mutation analysis by restriction digestion can be used to detect a KCNJ5 nucleic acid, or KCNJ5 nucleic acid, if the mutation results in the creation or elimination of a restriction site. A sample containing nucleic acid from the subject is used. Polymerase chain reaction (PCR) can be used to amplify all or a fragment of a nucleic acid (and, if necessary, the flanking sequences) in the sample. RFLP analysis is conducted as described (see Current Protocols in Molecular Biology, supra). The digestion pattern of the relevant fragments indicates the presence or absence of a mutation in KCNJ5.

Direct sequence analysis can also be used to detect specific mutations in KCNJ5. A sample comprising KCNJ5 DNA or RNA can be used, and PCR or other appropriate methods can be used to amplify all or a fragment of the nucleic acid, and/or its flanking sequences, if desired. The sequence, or a fragment thereof (e.g., one or more exons), or cDNA, or fragment of the cDNA, or mRNA, or fragment of the mRNA, is determined, using standard methods. The sequence of the gene, gene fragment, cDNA, cDNA fragment, mRNA, or mRNA fragment is compared with the known nucleic acid sequence of KCNJ5, as appropriate. The presence or absence of a mutation can then be identified.

Allele-specific oligonucleotides can also be used to detect the presence of a mutation in KCNJ5, through, for example, the use of dot-blot hybridization of amplified oligonucleotides with allele-specific oligonucleotide (ASO) probes (see, for example, 1986, Saiki et al., Nature 324:163-166).

An "allele-specific oligonucleotide" (also referred to herein as an "allele-specific oligonucleotide probe") is an oligonucleotide of approximately 10-50 base pairs, preferably approximately 15-30 base pairs, that specifically hybridizes to the mutant sequence, and that contains a mutation. An allele-specific oligonucleotide probe that is specific for a particular mutation can be prepared, using standard methods (see Current Protocols in Molecular Biology, supra). To identify a KCNJ5 mutation, a sample comprising nucleic acid is used. PCR can be used to amplify all or a fragment of the test nucleic acid sequence. The nucleic acid containing the amplified sequence (or fragment thereof) is dot-blotted, using standard methods (see Current Protocols in Molecular Biology, supra), and the blot is contacted with the oligonucleotide probe. The presence of specific hybridization of the probe to the amplified nucleic acid is then detected. Specific hybridization of an allele-specific oligonucleotide probe containing the mutation of interest, to test nucleic acid from the subject is indicative of the presence of the KCNJ5 mutation of interest.

In another embodiment of the invention, fluorescence resonance energy transfer (FRET) can be used to detect the presence of a mutation. FRET is the process of a distance-dependent excited state interaction in which the emission of one fluorescent molecule is coupled to the excitation of another. A typical acceptor and donor pair for resonance energy transfer consists of 4-[[4-(dimethylamino)phenyl] azo]benzoic acid (DABCYL) and 5-[(2-aminoethylamino] naphthalene sulfonic acid (EDANS). EDANS is excited by illumination with 336 nm light, and emits a photon with wavelength 490 nxn. If a DABCYL moiety is located within 20 angstroms of the EDANS, this photon will be efficiently absorbed. DABCYL and MANS will be attached to two different oligonucleotide probes designed to hybridize head-to-tail to nucleic acid adjacent to and/or overlapping the site of one of the mutations of interest. Melting curve analysis is then applied: cycles of denaturation, cooling, and re-heating are applied to a test sample mixed with the oligonucleotide probes, and the fluorescence is continuously monitored to detect a decrease in DABCYL fluorescence or an increase in EDANS fluorescence (loss of quenching). While the two probes remain hybridized adjacent to one another, FRET will be very efficient. Physical separation of the oligonucleotide probes results in inefficient FRET, as the two dyes are no longer in close proximity. The presence or absence of a KCNJ5 mutation of interest can be assessed by comparing the fluorescence intensity profile obtained from the test sample, to fluorescence intensity profiles of control samples comprising known KCNJ5 mutations of interest.

In another embodiment, arrays of oligonucleotide probes that are complementary to target nucleic acid sequence segments from a subject can be used to identify mutations in KCNJ5. For example, in one embodiment, an oligonucleotide array can be used. Oligonucleotide arrays typically comprise a plurality of different oligonucleotide probes that are coupled to a surface of a substrate in different known locations. These oligonucleotide arrays, also known as "Genechips," have been generally described in the art, for example, U.S. Pat. No. 5,143,854 and PCT patent publication Nos. WO 90/15070 and 92/10092. These arrays can generally be produced using mechanical synthesis methods or light directed synthesis methods which incorporate a combination of photolithographic methods and solid phase oligonucleotide synthesis methods. See Fodor et al., Science, 251:767-777 (1991), Pirrung et al., U.S. Pat. No. 5,143,854 (see also PCT Application No. WO 90/15070) and Fodor et al., PCT Publication No. WO 92/10092 and U.S. Pat. No. 5,424,186. Techniques for the synthesis of these arrays using mechanical synthesis methods are described in, e.g., U.S. Pat. No. 5,384,261.

After an oligonucleotide array is prepared, a nucleic acid of interest is hybridized with the array and scanned for KCNJ5 mutations. Hybridization and scanning are generally carried out by methods described herein and also in, e.g., Published PCT Application Nos. WO 92/10092 and WO 95/11995, and U.S. Pat. No. 5,424,186, the entire teachings of which are incorporated by reference herein. In brief, a target nucleic acid sequence which includes one or more previously identified mutations or markers is amplified by well-known amplification techniques, e.g., PCR. Typically, this involves the use of primer sequences that are complementary to the two strands of the target sequence both upstream and downstream of the mutation. Asymmetric PCR techniques may also be used. Amplified target, generally incorporating a label, is then hybridized with the array under appropriate conditions. Upon completion of hybridization and washing of the array, the array is scanned to determine the position on the array to which the target sequence hybridizes. The hybridization data obtained from the scan is typically in the form of fluorescence intensities as a function of location on the array.

Although often described in terms of a single detection block (e.g., for detection of a single mutation), arrays can include multiple detection blocks, and thus be capable of analyzing multiple, specific mutations. In alternate arrangements, it will generally be understood that detection blocks may be grouped within a single array or in multiple, separate arrays so that varying, optimal conditions may be used during the hybridization of the target to the array. This allows for the separate optimization of hybridization conditions for each situation. Additional description of use of oligonucleotide arrays for detection of polymorphisms can be found, for example, in U.S. Pat. Nos. 5,858,659 and 5,837,832, the entire teachings of which are incorporated by reference herein.

Other methods of nucleic acid analysis can be used to detect mutations of interest in KCNJ5. Representative methods include direct manual sequencing (1988, Church and Gilbert, Proc. Natl. Acad. Sci. USA 81:1991-1995; 1977, Sanger et al., Proc. Natl. Acad. Sci. 74:5463-5467; Beavis et al. U.S. Pat. No. 5,288,644); automated fluorescent sequencing; single-stranded conformation polymorphism assays (SSCP); clamped denaturing gel electrophoresis (CDGE); denaturing gradient gel electrophoresis (DGGE) (1981, Sheffield et al., Proc. Natl. Acad. Sci. USA 86:232-236), mobility shift analysis (1989, Orita et al., Proc. Natl. Acad. Sci. USA 86:2766-2770; 1987, Rosenbaum and Reissner, Biophys. Chem. 265:1275; 1991, Keen et al., Trends Genet. 7:5); restriction enzyme analysis (1978, Flavell et al., Cell 15:25; 1981, Geever, et al., Proc. Natl. Acad. Sci. USA 78:5081); heteroduplex analysis; chemical mismatch cleavage (CMC) (1985, Cotton et al., Proc. Natl. Acad. Sci. USA 85:4397-4401); RNase protection assays (1985, Myers, et al., Science 230:1242); use of polypeptides which recognize nucleotide mismatches, such as E. coli mutS protein (see, for example, U.S. Pat. No. 5,459,039); Luminex xMAP™ technology; high-throughput sequencing (HTS) (2011, Gundry and Vijg, Mutat Res, doi:10.1016/j.mrfmmm.2011.10.001); next-generation sequencing (NGS) (2009, Voelkerding et al., Clinical Chemistry 55:641-658; 2011, Su et al., Expert Rev Mol Diagn. 11:333-343; 2011, Ji and Myllykangas, Biotechnol Genet Eng Rev 27:135-158); ion semiconductor sequencing (2011, Rusk, Nature Methods doi:10.1038/nmeth.f.330; 2011, Rothberg et al., Nature 475:348-352)

and/or allele-specific PCR, for example. These and other methods can be used to identify the presence of one or more mutations of interest in KCNJ5, in a biological sample obtained from a subject. In one embodiment of the invention, the methods of assessing a biological sample for the presence or absence of a KCNJ5 mutation, as described herein, are used to diagnose an adrenal disease or disorder in a subject having a mutation in KCNJ5. Furthermore, more than one mutation may be found in KCNJ5.

The probes and primers according to the invention can be labeled directly or indirectly with a radioactive or nonradioactive compound, by methods well known to those skilled in the art, in order to obtain a detectable and/or quantifiable signal; the labeling of the primers or of the probes according to the invention is carried out with radioactive elements or with nonradioactive molecules. Among the radioactive isotopes used, mention may be made of $^{32}$P, $^{33}$P, $^{35}$S or $^{3}$H. The nonradioactive entities are selected from ligands such as biotin, avidin, streptavidin or digoxigenin, haptenes, dyes, and luminescent agents such as radioluminescent, chemoluminescent, bioluminescent, fluorescent or phosphorescent agents.

Nucleic acids can be obtained from the cells using known techniques. Nucleic acid herein refers to RNA, including mRNA, and DNA, including genomic DNA. The nucleic acid can be double-stranded or single-stranded (i.e., a sense or an antisense single strand) and can be complementary to a nucleic acid encoding a polypeptide. The nucleic acid content may also be an RNA or DNA extraction performed on a fresh or fixed tissue sample.

Routine methods also can be used to extract genomic DNA from a tissue sample, including, for example, phenol extraction. Alternatively, genomic DNA can be extracted with kits such as the QIAamp™. Tissue Kit (Qiagen, Chatsworth, Calif.), the Wizard™ Genomic DNA purification kit (Promega, Madison, Wis.), the Puregene DNA Isolation System (Gentra Systems, Inc., Minneapolis, Minn.), and the A.S.A.P.™ Genomic DNA isolation kit (Boehringer Mannheim, Indianapolis, Ind.).

There are many methods known in the art for the detection of specific nucleic acid sequences and new methods are continually reported. A great majority of the known specific nucleic acid detection methods utilize nucleic acid probes in specific hybridization reactions. Preferably, the detection of hybridization to the duplex form is a Southern blot technique. In the Southern blot technique, a nucleic acid sample is separated in an agarose gel based on size (molecular weight) and affixed to a membrane, denatured, and exposed to (admixed with) the labeled nucleic acid probe under hybridizing conditions. If the labeled nucleic acid probe forms a hybrid with the nucleic acid on the blot, the label is bound to the membrane.

In the Southern blot, the nucleic acid probe is preferably labeled with a tag. That tag can be a radioactive isotope, a fluorescent dye or the other well-known materials. Another type of process for the specific detection of nucleic acids of exogenous organisms in a body sample known in the art are the hybridization methods as exemplified by U.S. Pat. No. 6,159,693 and No. 6,270,974, and related patents. To briefly summarize one of those methods, a nucleic acid probe of at least 10 nucleotides, preferably at least 15 nucleotides, more preferably at least 25 nucleotides, having a sequence complementary to a desired region of the gene, or mutant gene, of interest is hybridized in a sample, subjected to depolymerizing conditions, and the sample is treated with an ATP/luciferase system, which will luminesce if the nucleic sequence is present. In quantitative Southern blotting, levels of the mutant KCNJ5 gene can be compared to wild-type levels of the KCNJ5 gene.

A further process for the detection of hybridized nucleic acid takes advantage of the polymerase chain reaction (PCR). The PCR process is well known in the art (U.S. Pat. No. 4,683,195, No. 4,683,202, and No. 4,800,159). To briefly summarize PCR, nucleic acid primers, complementary to opposite strands of a nucleic acid amplification target sequence, are permitted to anneal to the denatured sample. A DNA polymerase (typically heat stable) extends the DNA duplex from the hybridized primer. The process is repeated to amplify the nucleic acid target. If the nucleic acid primers do not hybridize to the sample, then there is no corresponding amplified PCR product. In this case, the PCR primer acts as a hybridization probe.

In PCR, the nucleic acid probe can be labeled with a tag as discussed before. Most preferably the detection of the duplex is done using at least one primer directed to KCNJ5. In yet another embodiment of PCR, the detection of the hybridized duplex comprises electrophoretic gel separation followed by dye-based visualization.

DNA amplification procedures by PCR are well known and are described in U.S. Pat. No. 4,683,202. Briefly, the primers anneal to the target nucleic acid at sites distinct from one another and in an opposite orientation. A primer annealed to the target sequence is extended by the enzymatic action of a heat stable DNA polymerase. The extension product is then denatured from the target sequence by heating, and the process is repeated. Successive cycling of this procedure on both DNA strands provides exponential amplification of the region flanked by the primers.

Amplification is then performed using a PCR-type technique, that is to say the PCR technique or any other related technique. Two primers, complementary to the KCNJ5 nucleic acid sequence, or KCNJ5 nucleic acid sequence, are then added to the nucleic acid content along with a polymerase, and the polymerase amplifies the DNA region between the primers.

The expression specifically hybridizing in stringent conditions refers to a hybridizing step in the process of the invention where the oligonucleotide sequences selected as probes or primers are of adequate length and sufficiently unambiguous so as to minimize the amount of non-specific binding that may occur during the amplification. The oligonucleotide probes or primers herein described may be prepared by any suitable methods such as chemical synthesis methods.

Hybridization is typically accomplished by annealing the oligonucleotide probe or primer to the DNA under conditions of stringency that prevent non-specific binding but permit binding of this DNA which has a significant level of homology with the probe or primer.

Among the conditions of stringency is the melting temperature (Tm) for the amplification step using the set of primers, which is in the range of about 55° C. to about 70° C. Preferably, the Tm for the amplification step is in the range of about 59° C. to about 72° C. Most preferably, the Tm for the amplification step is about 60° C.

Typical hybridization and washing stringency conditions depend in part on the size (i.e., number of nucleotides in length) of the DNA or the oligonucleotide probe, the base composition and monovalent and divalent cation concentrations (Ausubel et al., 1994, eds Current Protocols in Molecular Biology).

In a preferred embodiment, the process for determining the quantitative and qualitative profile according to the present invention is characterized in that the amplifications are real-time amplifications performed using a labeled probe, preferably a labeled hydrolysis-probe, capable of specifically hybridizing in stringent conditions with a segment of a KCNJ5 nucleic acid sequence, or mutant KCNJ5 nucleic acid sequence. The labeled probe is capable of emitting a detectable signal every time each amplification cycle occurs.

The real-time amplification, such as real-time PCR, is well known in the art, and the various known techniques will be employed in the best way for the implementation of the present process. These techniques are performed using various categories of probes, such as hydrolysis probes, hybridization adjacent probes, or molecular beacons. The techniques employing hydrolysis probes or molecular beacons are based on the use of a fluorescence quencher/reporter system, and the hybridization adjacent probes are based on the use of fluorescence acceptor/donor molecules.

Hydrolysis probes with a fluorescence quencher/reporter system are available in the market, and are for example commercialized by the Applied Biosystems group (USA). Many fluorescent dyes may be employed, such as FAM dyes (6-carboxy-fluorescein), or any other dye phosphoramidite reagents.

Among the stringent conditions applied for any one of the hydrolysis-probes of the present invention is the Tm, which is in the range of about 65° C. to 75° C. Preferably, the Tm for any one of the hydrolysis-probes of the present invention is in the range of about 67° C. to about 70° C. Most preferably, the Tm applied for any one of the hydrolysis-probes of the present invention is about 67° C.

In another preferred embodiment, the process for determining the quantitative and qualitative profile according to the present invention is characterized in that the amplification products can be elongated, wherein the elongation products are separated relative to their length. The signal obtained for the elongation products is measured, and the quantitative and qualitative profile of the labeling intensity relative to the elongation product length is established.

The elongation step, also called a run-off reaction, allows one to determine the length of the amplification product. The length can be determined using conventional techniques, for example, using gels such as polyacrylamide gels for the separation, DNA sequencers, and adapted software. Because some mutations display length heterogeneity, some mutations can be determined by a change in length of elongation products.

In one aspect, the invention includes a primer that is complementary to a nucleic acid sequence flanking the mutation of interest, and more particularly the primer includes 12 or more contiguous nucleotides substantially complementary to the sequence flanking the mutation of interest. Preferably, a primer featured in the invention includes a nucleotide sequence sufficiently complementary to hybridize to a nucleic acid sequence of about 12 to 25 nucleotides. More preferably, the primer differs by no more than 1, 2, or 3 nucleotides from the target flanking nucleotide sequence In another aspect, the length of the primer can vary in length, preferably about 15 to 28 nucleotides in length (e.g., 16, 17, 18, 19, 20, 21, 22, 23, 24, 25, 26, or 27 nucleotides in length).

The present invention also pertains to kits useful in the methods of the invention. Such kits comprise components useful in any of the methods described herein, including for example, hybridization probes or primers (e.g., labeled probes or primers), reagents for detection of labeled molecules, restriction enzymes (e.g., for RFLP analysis), antibodies, allele-specific oligonucleotides, means for amplification of subject's nucleic acids, means for analyzing the nucleic acid sequence of KCNJ5, means for analyzing the polypeptide sequence of KCNJ5, and instructional materials. For example, in one embodiment, the kit comprises components useful for analysis of KCNJ5 mutations associated with an adrenal disease or disorder. In a preferred embodiment of the invention, the kit comprises components for detecting one or more of the mutations of KCNJ5 associated with an adrenal disease or disorder elsewhere described herein.

Methods of Identifying a Modulator of an Adrenal Disease or Disorder

The current invention also relates to methods of identifying compounds that modulate an adrenal disease or disorder. In some embodiments, the method of identifying of the invention identifies a modulator compound that decreases level or activity of a mutant KNCJ5. In other embodiments, the method of identifying of the invention identifies modulator compound that increases the activity of a mutant KCNJ5. The invention further comprises compositions comprising the modulator of an adrenal disease or disorder, identified by the methods described herein. In various embodiments, the adrenal disease or disorder is at least one selected from the group consisting of aldosteronism, primary aldosteronism, secondary aldosteronism, hyperaldosteronism, primary hyperaldosteronism, secondary hyperaldosteronism, adrenal insufficiency, Addison's Disease, adrenoleukodystrophy, pheochromocytoma, Cushing's Syndrome, adrenal hyperplasia, congenital adrenal hyperplasia, cancer, adrenal cancer, hypertension, primary hypertension, secondary hypertension and virilization.

In one embodiment, the invention comprises a method of identifying a test compound as a modulator of an adrenal disease or disorder. Generally, the method of identifying a test compound as a modulator of an adrenal disease or disorder includes comparing a parameter of an adrenal disease or disorder in the presence of a test compound with a parameter of the adrenal disease or disorder in the absence of the test compound. Thus, in some embodiments, the method includes the steps of: measuring at least one parameter of an adrenal disease or disorder in the absence of the test compound; measuring the at least one parameter of the adrenal disease or disorder in the presence of the test compound; and comparing the level of the at least one parameter of the adrenal disease or disorder in the presence of the test compound with the level of the at least one parameter of the adrenal disease or disorder in the absence of the test compound; and identifying the test compound as a modulator of the adrenal disease or disorder when the level of the at least one parameter of the adrenal disease or disorder in the presence of the test compound is different than level of the at least one parameter of the adrenal disease or disorder in the absence of the test compound. In one embodiment, when the level of the parameter of the adrenal disease or disorder is higher in the presence of the test compound, the test compound is identified as an activator. In another embodiment, when the level of the parameter of the adrenal disease or disorder is lower in the presence of the test compound, the test compound is identified as an inhibitor.

In another embodiment, the invention comprises a method of identifying a test compound as a modulator of the mutant KCNJ5 selectivity filter. Generally, the method of identifying a test compound as a modulator of the mutant KCNJ5 selectivity filter includes comparing the activity of the mutant KCNJ5 selectivity filter in the presence of a test compound with the activity of the mutant KCNJ5 selectivity filter in the absence of the test compound. Thus, in some embodiments, the method includes the steps of: measuring the activity of the mutant KCNJ5 selectivity filter in the absence of the test compound; measuring the activity of the mutant KCNJ5 selectivity filter in the presence of the test compound; and comparing the level of activity of the mutant KCNJ5 selectivity filter in the presence of the test compound with the level of the activity of the mutant KCNJ5 selectivity filter in the absence of the test compound; and identifying the test compound as a modulator of the activity of the mutant KCNJ5 selectivity filter when the level of the activity of the mutant KCNJ5 selectivity filter in the presence of the test compound is different than level of the activity of the mutant KCNJ5 selectivity filter in the absence of the test compound. In one embodiment, when the level of the activity of the mutant KCNJ5 selectivity filter is higher in the presence of the test compound, the test compound is identified as an activator. In another embodiment, when the level of the activity of the mutant KCNJ5 selectivity filter is lower in the presence of the test compound, the test compound is identified as an inhibitor.

Suitable test compounds include, but are not limited to, a chemical compound, a protein, a peptide, a peptidomemetic, an antibody, a nucleic acid, an antisense nucleic acid, an shRNA, a ribozyme, and a small molecule chemical compound.

Other methods, as well as variations of the methods disclosed herein, will be apparent from the description of this invention. In various embodiments, the test compound concentration in the screening assay can be fixed or varied. A single test compound, or a plurality of test compounds, can be tested at one time. Suitable test compounds that may be used include, but are not limited to, proteins, nucleic acids, antisense nucleic acids, small molecules, antibodies and peptides.

The test compounds can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam et al., 1997, Anticancer Drug Des. 12:45).

Examples of methods for the synthesis of molecular libraries can be found in the art, for example, in: DeWitt et al., 1993, Proc. Natl. Acad. USA 90:6909; Erb et al., 1994, Proc. Natl. Acad. Sci. USA 91:11422; Zuckermann et al., 1994, J. Med. Chem. 37:2678; Cho et al., 1993, Science 261:1303; Carrell et al., 1994, Angew. Chem. Int. Ed. Engl. 33:2059; Carell et al., 1994, Angew. Chem. Int. Ed. Engl. 33:2061; and Gallop et al., 1994, J. Med. Chem. 37:1233.

Libraries of compounds may be presented in solution (e.g., Houghten, 1992, Biotechniques 13:412-421), or on beads (Lam, 1991, Nature 354:82-84), chips (Fodor, 1993, Nature 364:555-556), bacteria (Ladner U.S. Pat. No. 5,223,409), spores (Ladner U.S. Pat. No. '409), plasmids (Cull et al., 1992, Proc. Natl. Acad. Sci. USA 89:1865-1869) or on phage (Scott and Smith, 1990, Science 249:386-390; Devlin, 1990, Science 249:404-406; Cwirla et al., 1990, Proc. Natl. Acad. Sci. USA 87:6378-6382; Felici, 1991, J. Mol. Biol. 222:301-310; and Ladner supra).

In situations where "high-throughput" modalities are preferred, it is typical that new chemical entities with useful properties are generated by identifying a chemical compound (called a "lead compound") with some desirable property or activity, creating variants of the lead compound, and evaluating the property and activity of those variant compounds.

In one embodiment, high throughput screening methods involve providing a library containing a large number of test compounds potentially having the desired activity. Such "combinatorial chemical libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

Therapeutic Modulator Compositions and Methods of Use

In various embodiments, the present invention includes modulator compositions and methods of treating an adrenal disease or disorder, as well as methods of treating pathologies associated with an adrenal disease or disorder. In various embodiments, the adrenal disease or disorder is at least one selected from the group consisting of aldosteronism, primary aldosteronism, secondary aldosteronism, hyperaldosteronism, primary hyperaldosteronism, secondary hyperaldosteronism, adrenal insufficiency, Addison's Disease, adrenoleukodystrophy, pheochromocytoma, Cushing's Syndrome, adrenal hyperplasia, congenital adrenal hyperplasia, cancer, adrenal cancer, hypertension, primary hypertension, secondary hypertension and virilization. In other various embodiments, the pathology associated with an adrenal disease or disorder is at least one selected from the group consisting of hypernatremia, hypokalemia, hypocalcemia, hypomagnesemia, neoplasia, polyuria, polydipsia, heart disease, renal disease and stroke. In various embodiments, the modulator compositions and methods of treatment of the invention modulate the amount of mutant KCNJ5 polypeptide, the amount of mutant KCNJ5 mRNA, the amount of mutant KCNJ5 activity, or a combination thereof.

It will be understood by one skilled in the art, based upon the disclosure provided herein, that modulating the level of mutant KCNJ5 encompasses modulating the level of mutant KCNJ5 expression, including transcription, translation, or both. The skilled artisan will also appreciate, once armed with the teachings of the present invention, that modulating the level of mutant KCNJ5 includes modulating mutant KCNJ5 activity (e.g., selectivity filter activity, etc.). Thus, modulating the level or activity of mutant KCNJ5 includes, but is not limited to, modulating transcription, translation, or both, of a nucleic acid encoding mutant KCNJ5; and it also includes modulating any activity of a mutant KCNJ5 polypeptide as well.

In various embodiments, the modulator compositions and methods of the invention selectively modulate mutant KCNJ5, or can inhibit both wild-type and mutant KCNJ5. In one embodiment, the modulator compositions and methods of the invention selectively inhibit mutant KCNJ5, but do not substantially inhibit wild-type KCNJ5. In another embodiment, the modulator compositions and methods of the invention preferentially inhibit mutant KCNJ5, more than they inhibit wild-type KCNJ5. In a particular embodiment, the modulator compositions and methods of the invention diminish neoplasia associated with an adrenal disease or disorder.

In one embodiment, the modulator compositions and methods of the invention selectively inhibit an activity of the mutant KCNJ5 polypeptide, but do not substantially inhibit the activity of the wild-type KCNJ5 polypeptide. In another embodiment, the modulator compositions and methods of the invention preferentially inhibit an activity of the mutant KCNJ5 polypeptide, more than they inhibit the activity of the wild-type KCNJ5 polypeptide.

In another embodiment, the modulator compositions and methods of the invention selectively inhibit the mutant KCNJ5 selectivity filter, but do not substantially inhibit the wild-type KCNJ5 selectivity filter. In a further embodiment, the modulator compositions and methods of the invention preferentially inhibit the mutant KCNJ5 selectivity filter, more than they inhibit wild-type KCNJ5 selectivity filter. In yet another embodiment, the mutant KCNJ5 modulator of the invention restores potassium channel selectivity to a level comparable to that of wild-type KCNJ5.

Modulation of mutant KCNJ5 can be assessed using a wide variety of methods, including those disclosed herein, as well as methods known in the art or to be developed in the future. That is, the routineer would appreciate, based upon the disclosure provided herein, that modulating the level or activity of mutant KCNJ5 can be readily assessed using methods that assess the level of a nucleic acid encoding mutant KCNJ5 (e.g., mRNA), the level of a mutant KCNJ5 polypeptide present in a biological sample, the level of mutant KCNJ5 activity (e.g., selectivity filter activity, etc.), or combinations thereof.

One skilled in the art, based upon the disclosure provided herein, would understand that the invention is useful in treating an adrenal disease or disorder, or a pathology associated with an adrenal disease or disorder, in a subject in need thereof, whether or not the subject also being treated with other medication or therapy. Further, the skilled artisan would further appreciate, based upon the teachings provided herein, that the pathologies associated with an adrenal disease or disorder treatable by the compositions and methods described herein encompass any pathology associated with an adrenal disease or disorder where mutant KCNJ5 plays a role. In various embodiments, the pathology associated with an adrenal disease or disorder is at least one selected from the group consisting of hypernatremia, hypokalemia, hypocalcemia, hypomagnesemia, neoplasia, polyuria, polydipsia, heart disease, renal disease and stroke.

The mutant KCNJ5 modulator compositions and methods of the invention that modulate the level or activity of mutant KCNJ5 include, but should not be construed as being limited to, a chemical compound, a protein, a peptide, a peptidomemetic, an antibody, a ribozyme, a small molecule chemical compound, an antisense nucleic acid molecule (e.g., siRNA, miRNA, etc.), or combinations thereof. One of skill in the art would readily appreciate, based on the disclosure provided herein, that a mutant KCNJ5 modulator composition encompasses a chemical compound that modulates the level or activity of mutant KCNJ5. Additionally, a mutant KCNJ5 modulator composition encompasses a chemically modified compound, and derivatives, as is well known to one of skill in the chemical arts.

The mutant KCNJ5 modulator compositions and methods of the invention that modulate the level or activity of mutant KCNJ5 include antibodies. The antibodies of the invention include a variety of forms of antibodies including, for example, polyclonal antibodies, monoclonal antibodies, intracellular antibodies ("intrabodies"), Fv, Fab and F(ab)2, single chain antibodies (scFv), heavy chain antibodies (such as camelid antibodies), synthetic antibodies, chimeric antibodies, and humanized antibodies. In one embodiment, the antibody of the invention is an antibody that specifically binds to mutant KCNJ5, and does not substantially bind to KCNJ5. In another embodiment, the antibody of the invention is an antibody that specifically binds to mutant KCNJ5, and also specifically binds to KCNJ5.

Further, one of skill in the art would, when equipped with this disclosure and the methods exemplified herein, appreciate that a mutant KCNJ5 modulator composition includes such modulators as discovered in the future, as can be identified by well-known criteria in the art of pharmacology, such as the physiological results of modulation of mutant KCNJ5 as described in detail herein and/or as known in the art. Therefore, the present invention is not limited in any way to any particular mutant KCNJ5 modulator composition as exemplified or disclosed herein; rather, the invention encompasses those modulator compositions that would be understood by the routineer to be useful as are known in the art and as are discovered in the future.

Further methods of identifying and producing mutant KCNJ5 modulator compositions are well known to those of ordinary skill in the art, including, but not limited, obtaining a modulator from a naturally occurring source (i.e., *Streptomyces* sp., *Pseudomonas* sp., *Stylotella aurantium*). Alternatively, a modulator of mutant KCNJ5 can be synthesized chemically. Further, the routineer would appreciate, based upon the teachings provided herein, that a mutant KCNJ5 modulator composition can be obtained from a recombinant organism. Compositions and methods for chemically synthesizing mutant KCNJ5 modulators and for obtaining them from natural sources are well known in the art and are described in the art.

One of skill in the art will appreciate that a modulator can be administered as a small molecule chemical, a protein, an antibody, a nucleic acid construct encoding a protein, an antisense nucleic acid, a nucleic acid construct encoding an antisense nucleic acid, or combinations thereof. Numerous vectors and other compositions and methods are well known for administering a protein or a nucleic acid construct encoding a protein to cells or tissues. Therefore, the invention includes a method of administering a protein or a nucleic acid encoding a protein that is modulator of mutant KCNJ5. (Sambrook et al., 2001, Molecular Cloning: A Laboratory Manual, Cold Spring Harbor Laboratory, New York; Ausubel et al., 1997, Current Protocols in Molecular Biology, John Wiley & Sons, New York).

Antisense oligonucleotides are DNA or RNA molecules that are complementary to some portion of an RNA molecule. When present in a cell, antisense oligonucleotides hybridize to an existing RNA molecule and inhibit translation into a gene product. Inhibiting the expression of a gene using an antisense oligonucleotide is well known in the art (Marcus-Sekura, 1988, Anal. Biochem. 172:289), as are methods of expressing an antisense oligonucleotide in a cell (Inoue, U.S. Pat. No. 5,190,931). The methods of the invention include the use of an antisense oligonucleotide to modulate the amount of mutant KCNJ5, thereby modulating the amount or activity of mutant KCNJ5.

Contemplated in the present invention are antisense oligonucleotides that are synthesized and provided to the cell by way of methods well known to those of ordinary skill in the art. As an example, an antisense oligonucleotide can be synthesized to be between about 10 and about 100, more preferably between about 15 and about 50 nucleotides long. The synthesis of nucleic acid molecules is well known in the art, as is the synthesis of modified antisense oligonucleotides to improve biological activity in comparison to unmodified antisense oligonucleotides (Tullis, 1991, U.S. Pat. No. 5,023,243).

Similarly, the expression of a gene may be inhibited by the hybridization of an antisense molecule to a promoter or other regulatory element of a gene, thereby affecting the transcription of the gene. Methods for the identification of a promoter or other regulatory element that interacts with a gene of interest are well known in the art, and include such methods as the yeast two hybrid system (Bartel and Fields, eds., In: The Yeast Two Hybrid System, Oxford University Press, Cary, N.C.).

Alternatively, inhibition of a gene expressing of mutant KCNJ5 can be accomplished through the use of a ribozyme. Using ribozymes for inhibiting gene expression is well known to those of skill in the art (see, e.g., Cech et al., 1992, J. Biol. Chem. 267:17479; Hampel et al., 1989, Biochemistry 28: 4929; Altman et al., U.S. Pat. No. 5,168,053). Ribozymes are catalytic RNA molecules with the ability to cleave other single-stranded RNA molecules. Ribozymes are known to be sequence specific, and can therefore be modified to recognize a specific nucleotide sequence (Cech, 1988, J. Amer. Med. Assn. 260:3030), allowing the selective cleavage of specific mRNA molecules. Given the nucleotide sequence of the molecule, one of ordinary skill in the art could synthesize an antisense oligonucleotide or ribozyme without undue experimentation, provided with the disclosure and references incorporated herein.

One of skill in the art will appreciate that modulators of mutant KCNJ5 can be administered singly or in any combination. Further, modulators of mutant KCNJ5 can be administered singly or in any combination in a temporal sense, in that they may be administered concurrently, or before, and/or after each other. One of ordinary skill in the art will appreciate, based on the disclosure provided herein, that mutant KCNJ5 modulator compositions can be used to treat an adrenal disease or disorder, and that a modulator composition can be used alone or in any combination with another modulator to effect a therapeutic result.

In various embodiments, any of the modulators of the invention described herein can be administered alone or in combination with other modulators of other molecules associated with an adrenal disease or disorder. In some embodiments, the mutant KCNJ5 modulators of the invention selectively inhibit mutant KCNJ5 and do not also inhibit wild-type KCNJ5. In other embodiments, the mutant KCNJ5 modulators of the invention modulate mutant KCNJ5 and also modulate mutant KCNJ5.

It will be appreciated by one of skill in the art, when armed with the present disclosure including the methods detailed herein, that the invention is not limited to treatment of an adrenal disease or disorder, or a pathology associated with an adrenal disease or disorder, that is already established. Particularly, the disease, disorder or pathology need not have manifested to the point of detriment to the subject; indeed, the disease, disorder or pathology need not be detected in a subject before treatment is administered. That is, significant disease or disorder does not have to occur before the present invention may provide benefit. Therefore, the present invention includes a method for preventing an adrenal disease or disorder, in that a mutant KCNJ5 modulator composition, as discussed previously elsewhere herein, can be administered to a subject prior to the onset of the disease or disorder, thereby preventing the disease or disorder. The preventive methods described herein also include the treatment of a subject that is in remission for the prevention of a recurrence of an adrenal disease or disorder, or a pathology associated with an adrenal disease or disorder.

One of skill in the art, when armed with the disclosure herein, would appreciate that the prevention of an adrenal disease or disorder, or a pathology associated with an adrenal disease or disorder, encompasses administering to a subject a mutant KCNJ5 modulator composition as a preventative measure against an adrenal disease or disorder, or a pathology associated with an adrenal disease or disorder. As more fully discussed elsewhere herein, methods of modulating the level or activity of mutant KCNJ5 encompass a wide plethora of techniques for modulating not only mutant KCNJ5 activity, but also for modulating expression of a nucleic acid encoding mutant KCNJ5, including either transcription, translation, or both.

One skilled in the art would understand, once armed with the teaching provided herein, that the present invention encompasses methods of treating or preventing a wide variety of diseases, disorders and pathologies where modulating the expression and/or activity of KCNJ5, and/or mutant KCNJ5, mediates, treats or prevents the disease, disorder or pathology. Non-limiting examples of such diseases, disorders and pathologies include, but are not limited to, long QT syndrome (e.g., long QT syndrome 1, long QT syndrome 13, etc.) and migraines, such as migraines with aura.

Additionally, as disclosed elsewhere herein, one skilled in the art would understand, once armed with the teaching provided herein, that the present invention encompasses a method of preventing a wide variety of diseases, disorders and pathologies where modulating the expression and/or activity of KCNJ5, and/or mutant KCNJ5, mediates, treats or prevents the disease, disorder or pathology. Methods for assessing whether a disease relates to mutant KCNJ5 are known in the art. Further, the invention encompasses treatment or prevention of such diseases discovered in the future.

The invention encompasses administration of modulator of mutant KCNJ5 to practice the methods of the invention; the skilled artisan would understand, based on the disclosure provided herein, how to formulate and administer the appropriate mutant KCNJ5 modulator composition to a subject. Indeed, the successful administration of the mutant KCNJ5 modulator has been reduced to practice as exemplified herein. However, the present invention is not limited to any particular method of administration or treatment regimen.

Pharmaceutical Compositions

Compositions identified as potentially useful modulator compounds for treatment and/or prevention of an adrenal disease or disorder, can be formulated and administered to a subject for treatment of an adrenal disease or disorder, as now described.

The invention encompasses the preparation and use of pharmaceutical compositions comprising a composition useful for treatment of an adrenal disease or disorder, disclosed herein as modulator of mutant KCNJ5. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

As used herein, the term "pharmaceutically-acceptable carrier" means a chemical composition with which an appropriate inhibitor thereof, may be combined and which, following the combination, can be used to administer the appropriate inhibitor thereof, to a subject.

The pharmaceutical compositions useful for practicing the invention may be administered to deliver a dose of between about 0.1 ng/kg/day and 100 mg/kg/day.

In various embodiments, the pharmaceutical compositions useful in the methods of the invention may be administered, by way of example, systemically, parenterally, or topically, such as, in oral formulations, inhaled formulations, including solid or aerosol, and by topical or other similar formulations. In addition to the appropriate therapeutic composition, such pharmaceutical compositions may contain pharmaceutically acceptable carriers and other ingredients known to enhance and facilitate drug administration. Other possible formulations, such as nanoparticles, liposomes, resealed erythrocytes, and immunologically based systems may also be used to administer an appropriate inhibitor thereof, according to the methods of the invention.

As used herein, the term "physiologically acceptable" ester or salt means an ester or salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation.

Pharmaceutical compositions that are useful in the methods of the invention may be prepared, packaged, or sold in formulations suitable for oral, rectal, vaginal, parenteral, topical, pulmonary, intranasal, buccal, intravenous, ophthalmic, intrathecal and other known routes of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents.

Controlled- or sustained-release formulations of a pharmaceutical composition of the invention may be made using conventional technology.

A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically-controlled release tablets. Tablets may further comprise a sweetening agent, a flavoring agent, a coloring agent, a preservative, or some combination of these in order to provide pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

Liquid formulations of a pharmaceutical composition of the invention which are suitable for oral administration may be prepared, packaged, and sold either in liquid form or in the form of a dry product intended for reconstitution with water or another suitable vehicle prior to use.

Liquid suspensions may be prepared using conventional methods to achieve suspension of the active ingredient in an aqueous or oily vehicle. Aqueous vehicles include, for example, water and isotonic saline. Oily vehicles include, for example, almond oil, oily esters, ethyl alcohol, vegetable oils such as *arachis*, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent.

Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, and hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g. polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as *arachis*, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or *arachis* oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e. such as with a physiologically degradable material), and methods of absorbing an aqueous or oily solution or suspension into an absorbent material, with or without subsequent drying.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, cutaneous, subcutaneous, intraperitoneal, intravenous, intramuscular, intracisternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g., sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Formulations suitable for topical administration include, but are not limited to, liquid or semi-liquid preparations such as liniments, lotions, oil-in-water or water-in-oil emulsions such as creams, ointments or pastes, and solutions or suspensions. Topically-administrable formulations may, for example, comprise from about 1% to about 10% (w/w) active ingredient, although the concentration of the active ingredient may be as high as the solubility limit of the active ingredient in the solvent Formulations for topical administration may further comprise one or more of the additional ingredients described herein.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

The formulations described herein as being useful for pulmonary delivery are also useful for intranasal delivery of a pharmaceutical composition of the invention.

Another formulation suitable for intranasal administration is a coarse powder comprising the active ingredient and having an average particle from about 0.2 to 500 micrometers. Such a formulation is administered in the manner in which snuff is taken i.e. by rapid inhalation through the nasal passage from a container of the powder held close to the nares. Formulations suitable for nasal administration may, for example, comprise from about as little as 0.1% (w/w) and as much as 100% (w/w) of the active ingredient, and may further comprise one or more of the additional ingredients described herein.

A pharmaceutical composition of the invention may be prepared, packaged, or sold in a formulation suitable for buccal administration. Such formulations may, for example, be in the form of tablets or lozenges made using conventional methods, and may, for example, contain 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

A pharmaceutical composition of the invention may be prepared, packaged, or sold in a formulation suitable for ophthalmic administration. Such formulations may, for example, be in the form of eye drops including, for example, a 0.1-1.0% (w/w) solution or suspension of the active ingredient in an aqueous or oily liquid carrier. Such drops may further comprise buffering agents, salts, or one or more other of the additional ingredients described herein. Other opthalmically-administrable formulations which are useful include those which comprise the active ingredient in microcrystalline form or in a liposomal preparation.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, Remington's Pharmaceutical Sciences, Mack Publishing Co., Easton, Pa., which is incorporated herein by reference.

Typically dosages of the compound of the invention which may be administered to an animal, preferably a human, range in amount from about 0.01 mg to 20 about 100 g per kilogram of body weight of the animal. While the precise dosage administered will vary depending upon any number of factors, including, but not limited to, the type of animal and type of disease state being treated, the age of the animal and the route of administration. Preferably, the dosage of the compound will vary from about 1 mg to about 100 mg per kilogram of body weight of the animal. More preferably, the dosage will vary from about 1 μg to about 1 g per kilogram of body weight of the animal. The compound can be administered to an animal as frequently as several times daily, or it can be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the animal, etc.

EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Example 1: K+ Channel Mutations in Adrenal Aldosterone-Producing Adenomas and Hereditary Hypertension The materials and methods used in this Experimental Example are now described.

Subjects

Matched APA and venous blood DNAs were obtained from patients undergoing adrenalectomy for hypertension with primary aldosteronism and adrenocortical tumor at the Department of Surgery, University Hospital, Uppsala. Primary aldosteronism was diagnosed by a significantly elevated aldosterone:renin ratio (ARR), followed by confirmatory studies (Funder et al., 2008, J Clin Endocrinol Metab 93:3266-3281). Renin was measured in 2 patients as plasma renin activity (PRA; in mg/L/hr) and in 20 patients as plasma renin concentration (PRC; in mIU/L). An elevated ARR was considered to be aldosterone:PRA or aldosterone:PRC ratio greater than 100 and 50, respectively; all APA patients had ARR>230 (mean 420). Adrenal tumors were identified by CT scans. Adrenal vein sampling was usually performed in subjects over age 40 and documented lateralization of aldosterone production. When APA was considered the most likely diagnosis, unilateral adrenalectomy was performed (Funder et al., 2008, J Clin Endocrinol Metab 93:3266-3281). All APAs were verified by histopathology. When it was determined that procurement of tissue for genetic studies was possible without compromising the histopathological diagnosis, tumor tissue, determined by microscopy to be free of normal adrenal tissue, was snap-frozen in OCT using liquid nitrogen and stored at −80° C. until nucleic acid extraction. All patients displayed postoperative normokalemia and improvement in blood pressure control. Subjects from kindred HPA1 were evaluated as previously described (Geller et al., 2008, J Clin Endocrinol Metab 93:3117-3123). The research protocols of all studies were approved by local IRB's and informed consent was obtained from all participants.

DNA Preparation, Genotyping and Exome Sequencing

Genomic DNA was prepared from subject venous blood and tumor tissue by standard procedures. SNP genotyping of blood and tumor genomic DNAs was performed on the Illumina Human 1M-Duo DNA Analysis BeadChip. The image data was analyzed and SNP genotypes were called using Beadstudio software (Illumina). Genome-wide intensity and B-allele frequency was plotted using a perl script.

Targeted capture of human whole exome sequences using solution-based 2.1M NimbleGen Exome array followed by Illumina Genome Analyzer IIx sequencing was performed as previously described (Choi et al., 2009, Proc Natl Acad Sci USA 106:19096-19101). Three lanes of paired-end sequence reads of 74 or 99 bp length were generated following the manufacturer's protocol. Subsequent image analysis and base calling was done by Illumina pipeline (ver. 1.5) with default settings at Yale University's High Performance Computing Cluster.

Genomic sequences were mapped to the human genome (hg18) using Maq software (Li et al., 2008, Genome Res 18:1851-1858). Reads aligned to the targeted sequences were retrieved and subjected to further analyses using perl scripts. Pairs of reads sharing the same start and end positions were regarded as PCR duplicates and discarded using Samtools software (Li et al., 2009, Bioinformatics 25:2078-2079) dbSNP (build 131) and 1000 genomes database (release 07/20/10) were used to test novelty of variations. For somatic mutation discovery, positions with at least 8 reads in both tumor and blood DNA were evaluated, and those with at least 2 minor allele calls in tumor and less than 5 minor allele calls in blood samples were further evaluated. The significance of differences in read distributions at these positions between tumor and blood were evaluated by two-tailed Fisher's exact test to produce a list of putative somatic mutations in tumors ranked by p-value. Under the assumption that few if any clonal somatic changes should occur in blood DNA, as a control the same test was applied to blood DNA using tumor DNA as reference. Among the 4 tumor-blood pairs, there were 13 putative somatic mutations in tumor with p<10-4 vs. 1 putative somatic mutation in blood (which was not confirmed), consistent with a high fraction of the variants in tumor representing bona fide somatic mutations. In contrast, the number of putative somatic mutations was similar in tumor and blood for p>10-4 FIG. 7. Consistent with expectation from this analysis, 12 of 13 putative somatic mutations in tumor with p<10-4 validated by Sanger sequencing while 0 of 28 with 10-3>p>10-4 validated FIG. 16. To evaluate the somatic mutation rate all bases with at least 40 independent Illumina reads were considered, which comprised 86.2% of the targeted bases in tumors. Also assessed were small LOH segments (down to 1 Mb), and no small somatic LOH segments in any of the 4 tumors subjected to exome sequencing were found.

Direct Sanger sequencing of putative somatic mutations identified by exome sequencing and of KCNJ5 in all tumor-blood pairs was performed by standard methods following PCR amplification using specific primers. Sequences of the three independent sets of primers used for sequencing KCNJ5 mutations are as follows:

```
Set 1 forward primer:
                                      (SEQ ID NO: 1)
KCNJ5-Fn2 (5'-CGACCAAGAGTGGATTCCTT-3')

Set 1 reverse primer:
                                      (SEQ ID NO: 2)
KCNJ5-Rn2 (5'-AGGGTCTCCGCTCTCTTCTT-3')

Set 2 forward primer:
                                      (SEQ ID NO: 3)
KCNJ5-6-F (5'-GCTTCATTTGGTGGCTCATT-3')
```

```
Set 2 reverse primer:
                                        (SEQ ID NO: 4)
KCNJ5-6-R (5'-CCACCATGAAGGCATTGAC-3')

Set 3 forward primer:
                                        (SEQ ID NO: 5)
KCNJ5-7-F (5'-GTGTCCGCTTTCCTGTTCTC-3')

Set 3 reverse primer:
                                        (SEQ ID NO: 6)
KCNJ5-7-R (5'-GAGATGACTGCGTTGTTGGA-3')
```

Structural Modeling

Based on a multiple sequence alignment of all known K+ channel structures, chicken KCNJ12 was used as a model for the KCNJ5 mutations (Tao et al. 2009, Science 326:1668-1674). The homotetramer of KCNJ12 was generated from a subunit of KCNJ12 (PDB ID: 3JYC) by applying crystallographic symmetry (I4) using PyMOL software (DeLano, 2002, The PyMOL molecular graphics system. DeLano Scientific, San Carlos, Calif., USA). The stereochemistry of the mutated side chains in KCNJ5 were determined with COOT software (Emsley and Cowtan, 2004, Acta Crystallogr D Biol Crystallogr 60:2126-2132). Hydrogen bonds were identified using PyMOL consistent with the geometry criteria of DSSP (Kabsch and Sander, 1983, Biopolymers 22:2577-2637).

KCNJ5 Immunohistochemistry

Protein expression was analyzed by IHC as described previously (Bjorklund et al., 2007, J Clin Endocrinol Metab 92:338-344). In brief, sections (6 μm) from formalin fixed paraffin embedded normal adrenal cortex obtained at adrenalectomy for pheochromocytoma were deparaffinized and subjected to antigen retrieval in 10 mM sodium citrate (pH 6.0) for 15 minutes and were incubated with polyclonal anti-KCNJ5 (#HPA017353, Sigma; 1:100 dilution) and anti-Dab2 (#sc-13982, Santa Cruz; 1:100 dilution). Horseradish peroxidase-conjugated anti-rabbit secondary antibody was used for visualization of the signal. Sections were counterstained with hematoxylin-eosin.

Molecular Cloning

Human KCNJ5 was obtained from Origene (#SC119590). The full-length cDNA was sequenced and subcloned into the pIRES2-eGFP vector (Clontech) with EcoRI and BamHI using a PCR-based strategy. Site-directed mutagenesis (Quikchange, Stratagene) was performed to introduce the G151R, T158A, and L168R mutations using the following primers:

```
J5G151R_F:
                                        (SEQ ID NO: 7)
5'-CCGAAACAACCATTAGGTATGGCTTCCGAG-3'

J5G151R_R:
                                        (SEQ ID NO: 8)
5'-CTCGGAAGCCATACCTAATGGTTGTTTCGG-3'

J5T158A_F:
                                        (SEQ ID NO: 9)
5'-CTTCCGAGTCATCGCAGAGAAGTGTCC-3'

J5T158A_R:
                                        (SEQ ID NO: 10)
5'-GGACACTTCTCTGCGATGACTCGGAAG-3'

J5L168R_F:
                                        (SEQ ID NO: 11)
5'-GGATTATACTCCGCTTGGTCCAGGCC-3'

J5L168R_R:
                                        (SEQ ID NO: 12)
5'-GGCCTGGACCAAGCGGAGTATAATCC-3'.
```

All mutations were confirmed by sequencing. cDNA clones encoding human KCNJ3 (Origene #SC118769) and human dopamine receptor D2 (Open Biosystems #MHS1011-74442) were subcloned into the pcDNA3.1(+) vector (Invitrogen) with KpnI and XhoI using PCR-based strategies.

Electrophysiology 293T cells were transfected with plasmid DNA using TransIT®-293 Transfection Reagent (Mirus) according to the manufacturer's instructions. Empty vector was used as a control. Cells were examined one day after transient transfection. Standard perforated whole-cell patch clamp recordings were performed on GFP-positive cells using an Axopatch 200A (Axon Instruments) amplifier. Pipettes were pulled from borosilicate glass and had resistances between 2 MΩ and 4 MΩ with 140 mM KCl in the pipette.

Electrophysiology of KCNJ3/KCNJ5 Heterotetramers

Cells were cotransfected with 0.8 μg wild-type or mutant KCNJ5 and 0.5 μg KCNJ3 cDNA. The extracellular solution contained 140 mM NaCl, 5 mM KCl, 1.8 mM MgCl$_2$, 1.8 mM CaCl$_2$, and 10 mM HEPES (pH 7.4), while the intracellular solution contained 140 mM KCl, 4 mM MgCl2, 1 mM CaCl2, 1 mM EGTA, and 5 mM HEPES (pH 7.4). 1 mM BaCl2 was used to block Kir channels. For ion substitution, 140 mM NaCl was replaced with 140 mM choline chloride with or without the presence of BaCl2. The pipette holding potential was 0 mV before clamping, and the cell was clamped from −100 to 60 mV with 20 mV increments. Endogenous currents of 293T cells transfected with empty vector were measured from −100 to 60 mV. These were considered background currents and subtracted from the whole-cell current for each experiment. Data were analyzed by a combination of Axon Clampfit9.2 (Molecular Devices) and SigmaPlot (Jandel Scientific) programs. Data from 3-7 cells were analyzed for each construct. All data are shown as mean±SEM. Cell capacitances varied between 24.5 and 26 pF, and were used to normalize currents to that of a 25 pF cell.

The relative permeability of K+ to Na+ was estimated from the reversal potential using the Goldman equation with K+ and Na+ as the predominant permeant cations, consistent with experimental data.

$$E_{rev} = \frac{RT}{F} \cdot \ln \frac{p_K[K^+]_o + p_{Na}[Na^+]_o}{p_K[K^+]_i + p_{Na}[Na^+]_i}$$

$E_{rev}$, reversal potential; p, permeability; R, gas constant; T, temperature (24° C.); F, Faraday's constant.

For measurement of KCNJ3/KCNJ5 response to GPCR activation, 0.5 μg type 2 dopamine receptor (D2R) cDNA was added to the transfection, and cells were stimulated by addition of 1 μM dopamine hydrochloride (Sigma) to the extracellular solution prior to current measurements.

Electrophysiology of KCNJ5 Homotetramers

To analyze homomeric wild-type or mutant KCNJ5 currents, 1 μg of cDNA was transfected. Because KCNJ5 homotetramers have a low current, symmetrical high Na+ and high K+ solutions were separately used to increase the current (Owen et al., 1999, Exp Physiol 84:471-488; Andreoli, et al., Eds., Molecular Biology of Membrane Transport Disorders (Plenum Press, New York, ed. 2, 1996), chap. 5). For each construct, currents were measured in two conditions. In one, the extracellular solution contained 140 mM NaCl, 5 mM KCl, 1.8 mM MgCl2, 1.8 mM CaCl2, and 10 mM HEPES, pH 7.4, and the intracellular solution was the same except it also had 2 mM EGTA; in the other, the extracellular solution contained 140 mM KCl, 0.5 mM MgCl2, 1.5 mM CaCl2, and 10 mM HEPES, pH 7.4, and the intracellular solution 140 mM KCl, 4 mM MgCl2, 1 mM CaCl2, 1 mM EGTA, and 5 mM HEPES, pH 7.4. Electrophysiology protocol and analysis was as above for KCNJ5/KCNJ3 heterotetramers. For determination of the reversal potential, the extracellular solution contained 140 mM NaCl, 5 mM KCl, 1.8 mM MgCl2, 1.8 mM CaCl2, and 10 mM HEPES (pH 7.4), while the intracellular solution contained 140 mM KCl, 4 mM MgCl2, 1 mM CaCl2, 1 mM EGTA, and 5 mM HEPES (pH 7.4). 1 mM BaCl2 was added to test sensitivity of currents to barium. The reversal potential was determined using a ramp protocol ranging from −100 to +100 mV after forming a high resistance seal. The test was repeated at least twice in each cell, and 3 cells were studied for each construct.

Western Blotting 293T cells transfected with WT or mutant KCNJ5 plus KCNJ3 as above were harvested and lysed in a buffer containing 50 mM HEPES pH 7.4, 250 mM NaCl, 1.5 mM MgCl2, 1 mM EGTA pH 8.0, 10% glycerol, 1% Triton X-100 and protease inhibitors (Roche). Cleared lysates were quantified by a BCA assay (Pierce); equal amounts were fractionated by SDS-PAGE and transferred to a PVDF membrane (Millipore). The membrane was blocked and incubated with anti-KCNJ5 (Sigma, #HPA017353, 1:500 dilution), followed by a HRPconjugated secondary antibody. Bands were visualized by ECL (GE Healthcare). The blot was incubated in ECL stripping buffer at 65° C. for 45 min, re-blocked, and incubated with an anti-KCNJ3 antibody (Alomone #APC-005, 1:1000 dilution), again followed by a HRP-conjugated secondary antibody.

Orthologs and Paralogs

Full-length orthologous protein sequences were identified by a BLAST search of human KCNJ5 and extracted from GenBank. Orthologs were confirmed based on database identity of annotation or in a BLAST of the protein sequence against the human protein sequence, with the requirement that human KCNJ5 be the top hit. Protein sequences were aligned using the ClustalW algorithm. GenBank accession numbers were: NP_000881.3 (human), NP_034735.3 (mouse), XP_417864.2 (chicken), NP_001016901.1 (frog), XP_700619.4 (zebrafish), and XP_002122831.1 (tunicate). For human inward rectifier paralogs, GenBank accession numbers were: NP_000211.1 (KCNJ1), NP_000882.1 (KCNJ2), NP_066292.2 (KCNJ12), NP_002230.1 (KCNJ3), NP_002232.2 (KCNJ10), NP_733938.1 (KCNJ16), NP_004973.1 (KCNJ8), and NP_002233.2 (KCNJ13).

Example KCNJ5 Amino Acid Sequence

```
KCNJ5; Genbank Accession Number NP_000881.3;
                                                      SEQ ID NO: 13
MAGDSRNAMNQDMEIGVTPWDPKKIPKQARDYVPIATDRTRLLAEGKKPRQ

RYMEKSGKCNVHHGNVQETYRYLSDLFTTLVDLKWRFNLLVFTMVYTVTW

LFFGFIWWLIAYIRGDLDHVGDQEWIPCVENLSGFVSAFLFSIETETTIGYGFR

VITEKCPEGIILLLVQAILGSIVNAFMVGCMFVKISQPKKRAETLMFSNNAVIS

MRDEKLCLMFRVGDLRNSHIVEASIRAKLIKSRQTKEGEFIPLNQTDINVGFDT

GDDRLFLVSPLIISHEINQKSPFWEMSQAQLHQEEFEVVVILEGMVEATGMTC

QARSSYMDTEVLWGHRFTPVLTLEKGFYEVDYNTFHDTYETNTPSCCAKELA

EMKREGRLLQYLPSPPLLGGCAEAGLDAEAEQNEEDEPKGLGGSREARGSV
```

Adrenal Cortical Gene Expression

Normal human adrenal cortical tissue from two patients undergoing adrenalectomy for pheochromocytoma at University Hospital, Uppsala was dissected and determined by histology to be free of tumor or adrenal medulla tissue. Tissue processing and hybridization were performed in duplicate using the Human Gene 1.0 ST Array (Affymetrix). Raw intensity data from the 4 hybridizations was normalized by RMA method implemented in R package affy (Gautier et al., 2004, Bioinformatics 20:307-315).

The results of this Experimental Example are now described.

Twenty-two patients with APA were studied in the studies of this example (FIG. 14). All came to medical attention with hypertension and variable hypokalemia. All had high aldosterone:renin ratios and unilateral adrenal cortical mass on CT. At surgery, adrenocortical tumors of mean diameter 2.8 cm were removed, and pathology in all cases confirmed adrenocortical adenoma.

Figures 6A, 6B, 6C:
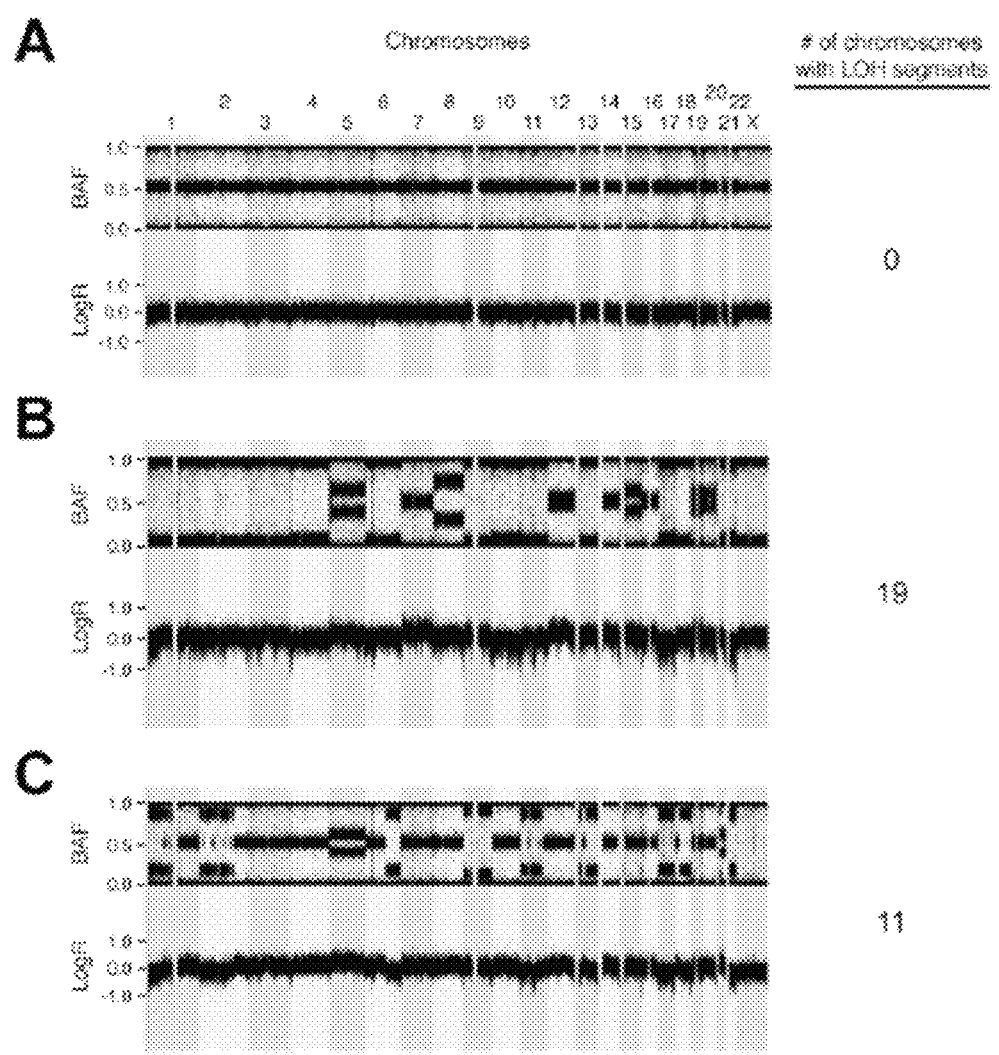
FIGS. 6A-6C, depicts the results of experiments assessing the loss of heterozygosity (LOH) in aldosterone-producing adenomas. Genome-wide distribution of intensity (Log R) and B-allele fraction (BAF) from APA tumors with varying degree of LOH. The number of LOH-affected chromosomes is shown on the right.

Genotyping of tumors on Illumina 1M-Duo chips demonstrated two gross classes of tumors: those with zero or few chromosome arms with loss of heterozygosity (LOH) (11 with none, 3 with 1 to 4 LOH events) and those with many large LOH segments (8 with 11 to 19 LOH segments) (FIGS. 6 and 14). Subjects with low LOH tumors tended to be younger with smaller tumors.

Figure 7:
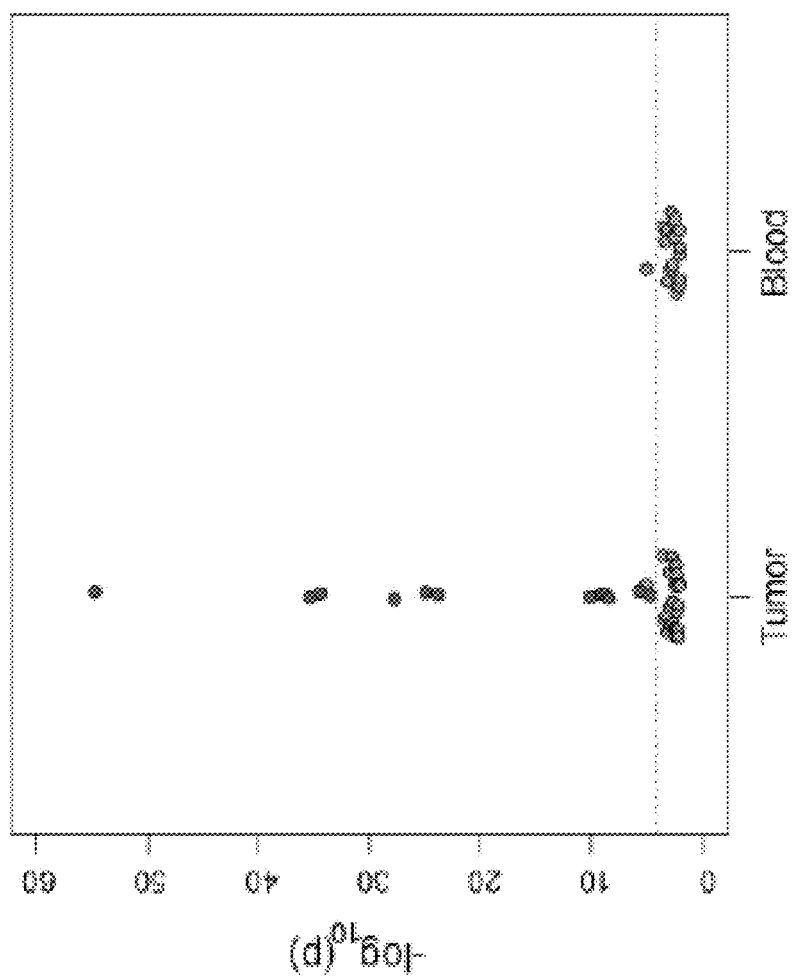
FIG. 7 depicts the p-value distribution of putative somatic mutations in APAs. −log 10 p-values from Fisher's exact test for the significance of read count differences of putative somatic mutations in tumor samples (Tumor) using blood as a reference; as control, the p-value distribution of variants in blood (labeled Blood) seen in excess using tumor reads as a reference. Dotted line denotes $p=10^{-4}$.
Figure 8A:
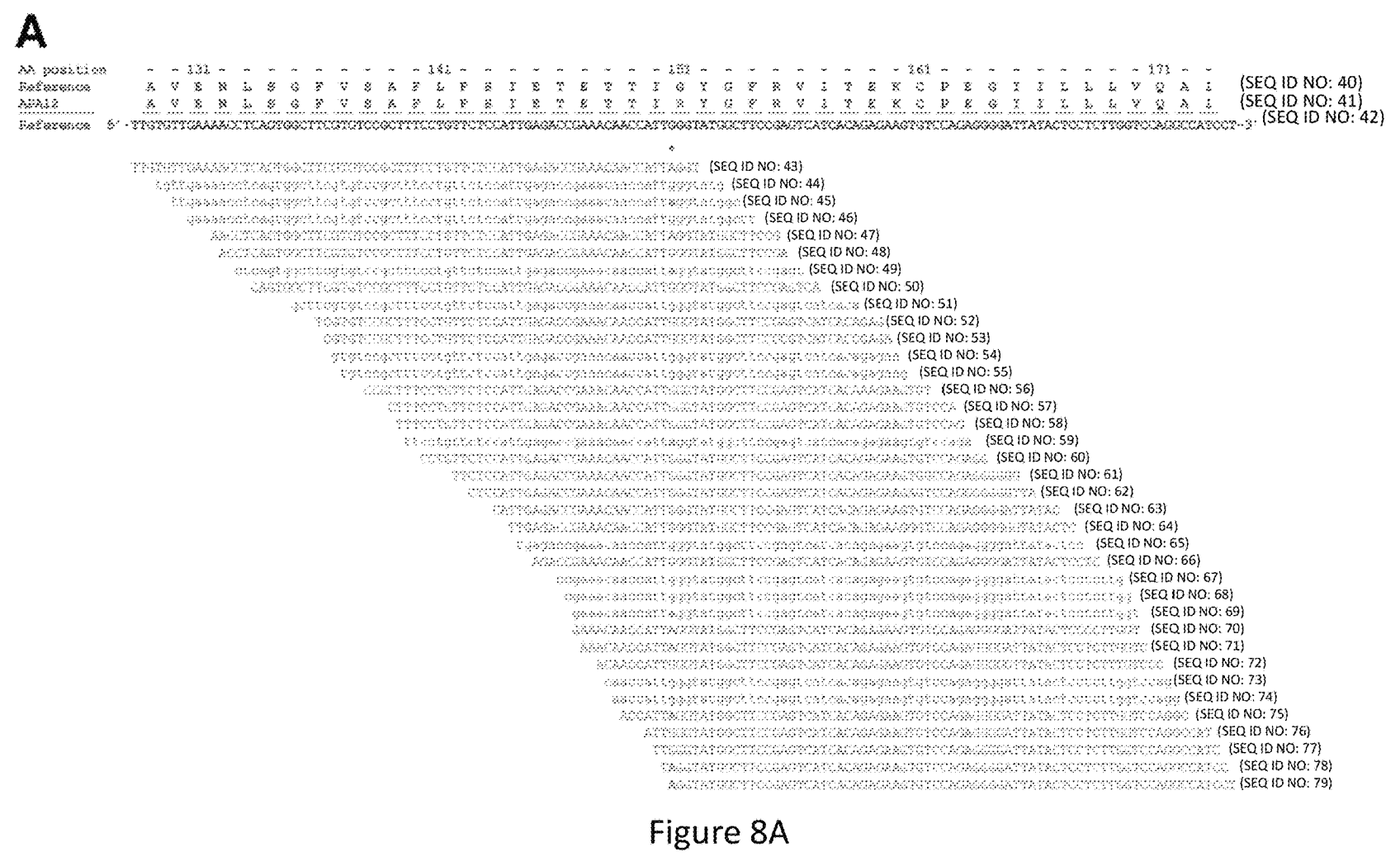
Figure 8B:
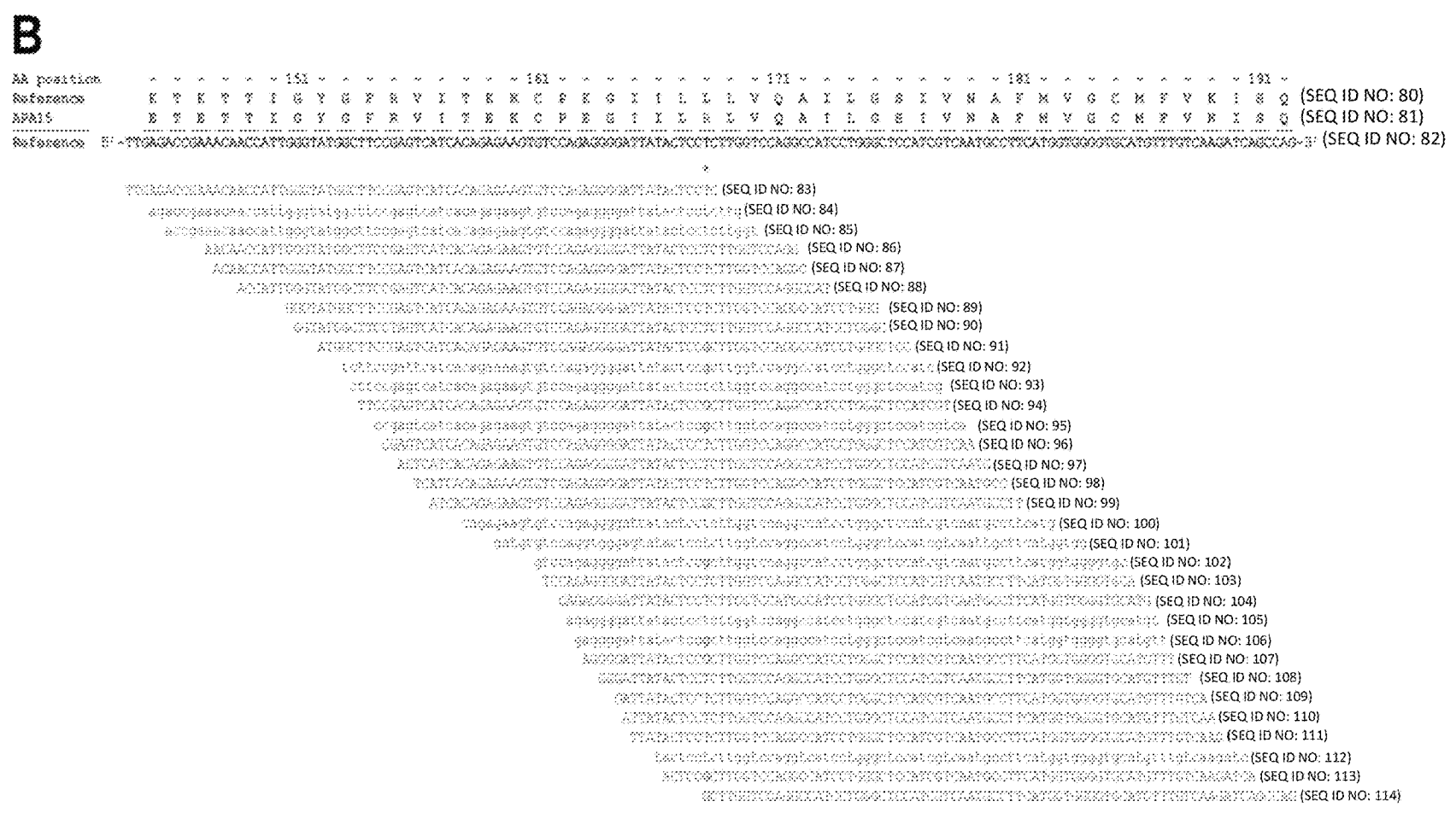
Figures 9A, 9B, 9C:
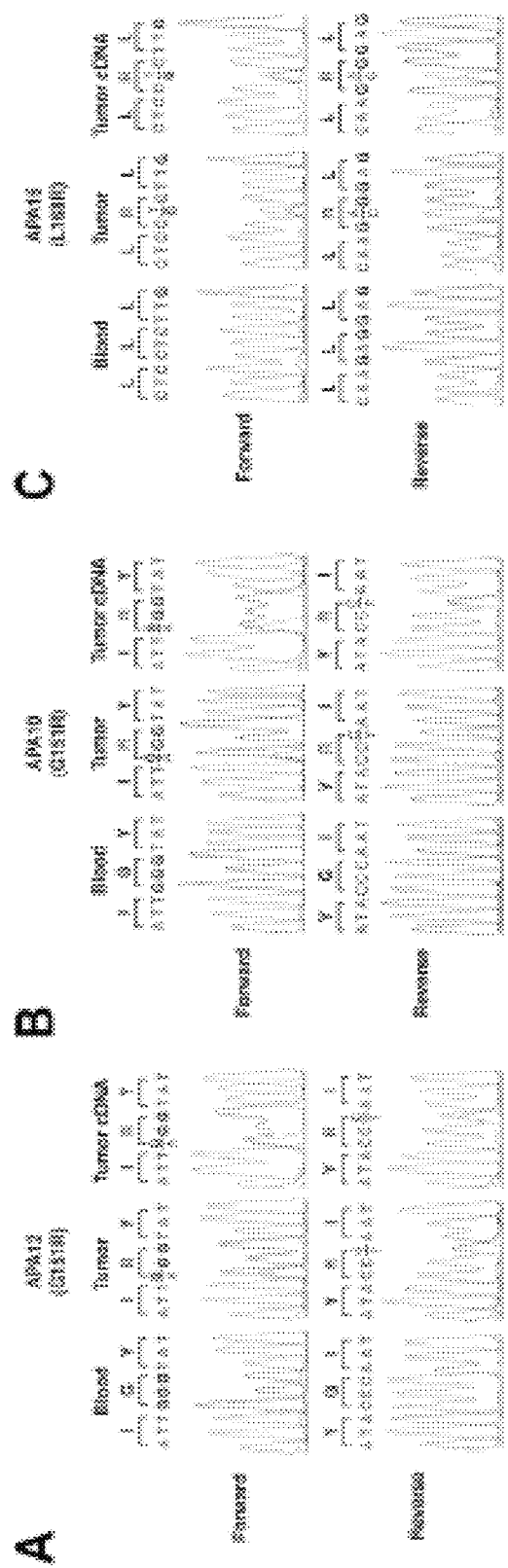
FIGS. 9A-9I, depicts Sangar traces of tumor samples having mutations in KCNJ5 in aldosterone-producing adenoma and inherited primary aldosteronism. Sanger traces from 8 tumor samples with somatic mutations G151R or L168R in KCNJ5 (FIGS. 9A-9H) along with confirmation sequences from tissue cDNA (9A-9F) are shown.
Figures 9D, 9E, 9F:
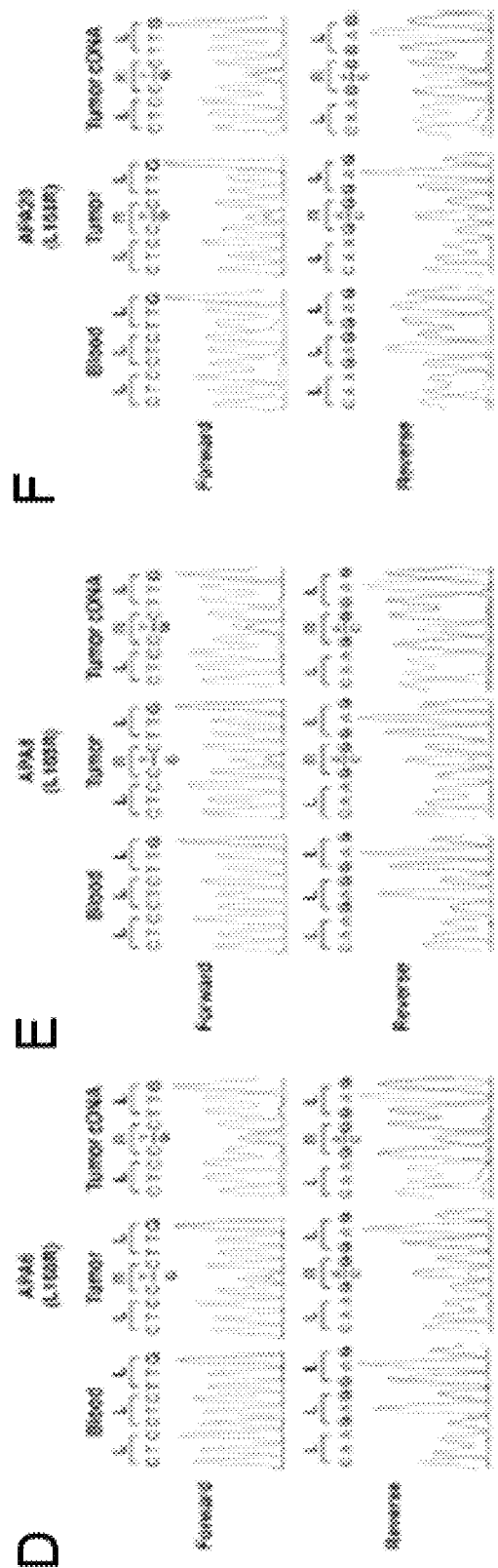
Figure 16:
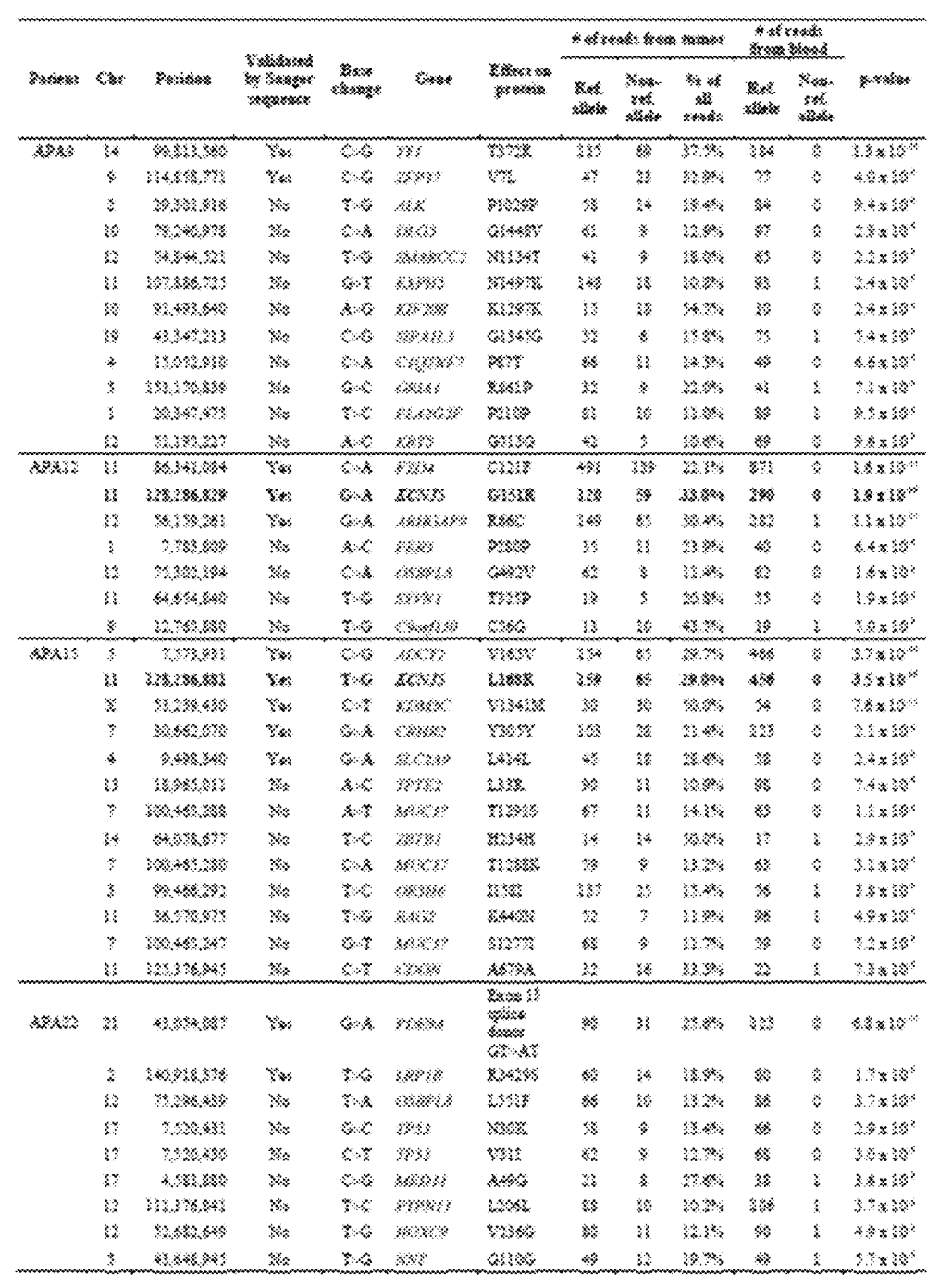

Whole exome capture and Illumina sequencing was performed on four APA-blood pairs from unrelated subjects with no LOH segments. Each tumor sample was assessed by histology to be free of normal adrenal cells; some admixture with blood and stromal cells is inevitable, and thus samples were sequenced to high depth of coverage to enable detection of somatic mutations. The mean coverage of each targeted base was 183-fold for blood DNA and 158-fold for tumor DNA, and 97% of all targeted bases in tumor samples were read at least eight times (FIG. 15). High-probability somatic mutations were identified in each tumor (P=10-4 to 10-56 of chance occurrence) (FIG. 7), and confirmed each by direct Sanger sequencing. Twelve of 13 putative somatic mutations were confirmed by Sanger sequencing versus 0 of 28 with 10-4<P<10-3 (FIGS. 5, 7 and 16). The results identified a small number of somatic mutations in each tumor, with a mean of 2.3 protein-altering and 0.8 silent mutations (FIGS. 5 and 16). Among bases covered≥40-fold (86% of all targeted bases), this represents 0.15 somatic mutations per megabase of exome sequence, a low value compared with a number of malignant tumors (Wood et al., 2007, Science 318:1108; Sjoblom et al., 2006, Science 314:268). Considering the small number of somatic protein-altering mutations, it was remarkable that one gene, KCNJ5 (Kir3.4), was mutated in two tumors (FIGS. 1, 5, 8 and 9). KCNJ5 encodes an inwardly rectifying K+ channel (Krapivinsky et al., 1995, Nature 374:135). One mutation was G151R, which was present in 33% of tumor reads and none in blood. The other was L168R, present in 29% of tumor reads and none in blood. Each was confirmed as a somatic mutation by Sanger sequencing. Both the wild-type (WT) and mutant KCNJ5 transcripts were detected in APA cDNA (FIGS. 1 and 9). The G151R and L168R mutations are absent in the dbSNP, 1000 Genomes, and Catalogue of Somatic Mutations in Cancer (COSMIC) databases. Sequencing 900 KCNJ5 alleles from unrelated subjects revealed neither mutation and only two missense variants, R39H and M210I, both in cytoplasmic domains. Staining of normal human adrenal gland with antibodies to KCNJ5 demonstrated selective staining of zona glomerulosa cells (FIG. 10), consistent with tumors arising from mutation in these cells.

Sequencing of KCNJ5 in the other 18 APA-blood pairs identified six additional somatic mutations. Remarkably, all were either the G151R or L168R mutation. In sum, there were two G151R mutations and six L168R mutations among the 22 tumors (FIGS. 6 and 9). The mutations were expressed in tumor cDNA in the six samples studied (FIG. 9). Mutant allele frequencies in tumor DNA and cDNA are consistent with mutations being heterozygous in tumor cells. All KCNJ5 mutations were in the low LOH group, including 7 of the 11 tumors with no LOH segments.

Even using an inflated estimate of one somatic mutation per million base pairs in these tumors, the probability of seeing either of two somatic mutations recur by chance in 6 of 20 other tumors is $<10^{-30}$, strongly implicating these two mutations in the pathogenesis of APA. The recurrence of the identical mutations strongly implies a genetic gain-of-function mechanism.

Figure 1C:
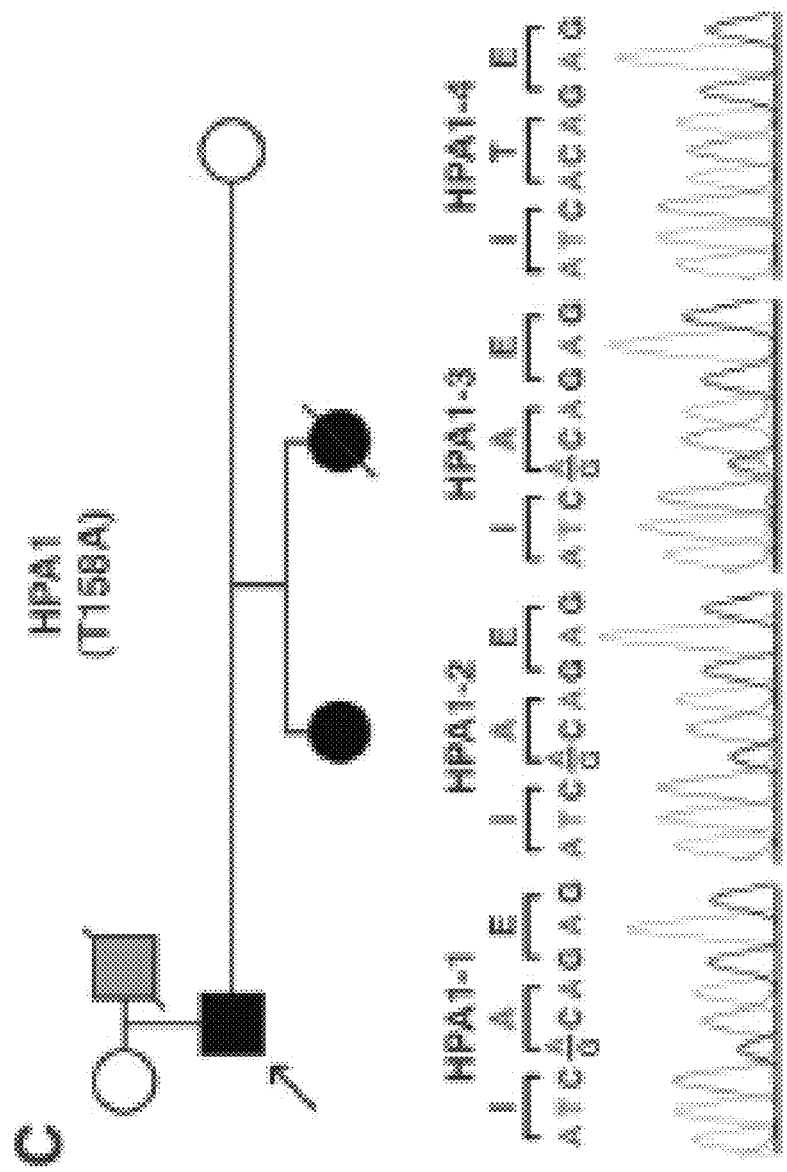
Figure 1D:
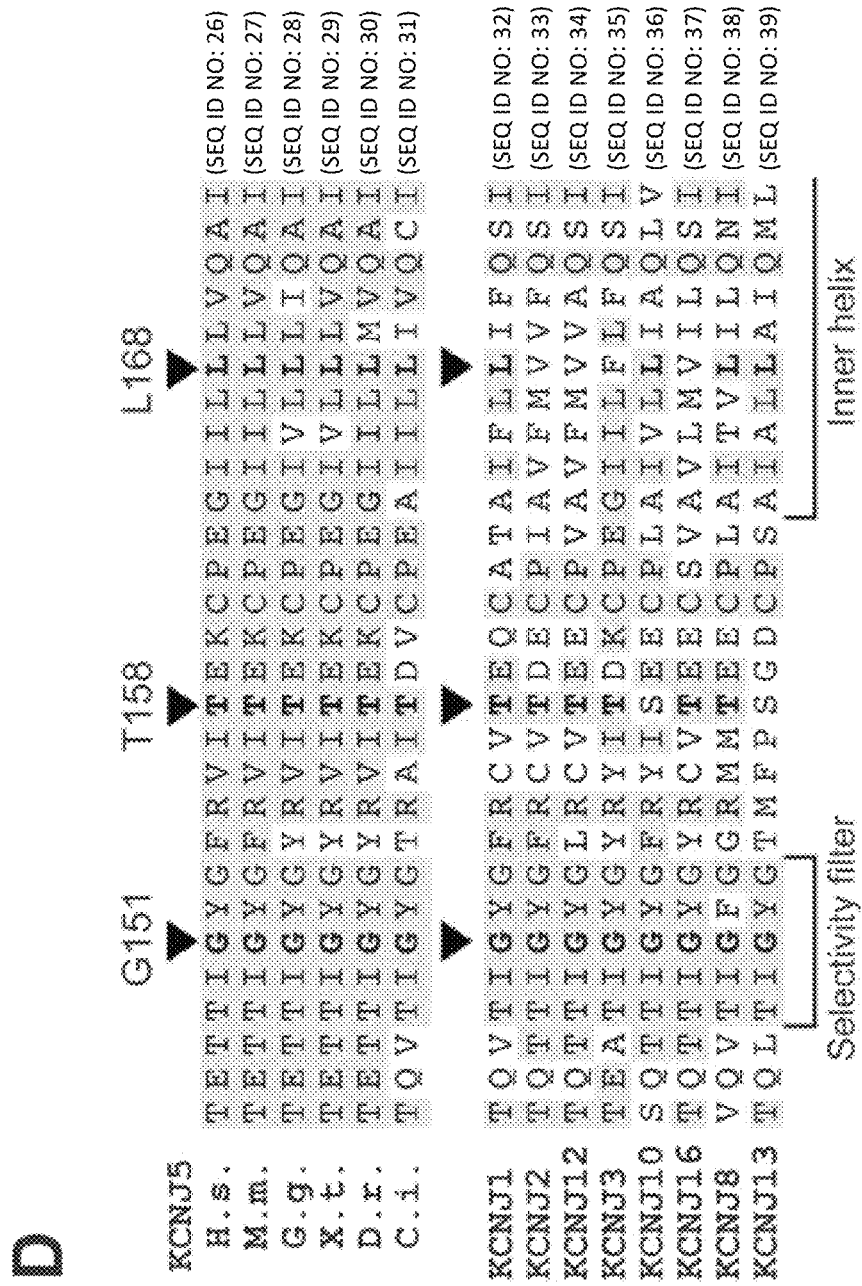
Figure 2A:
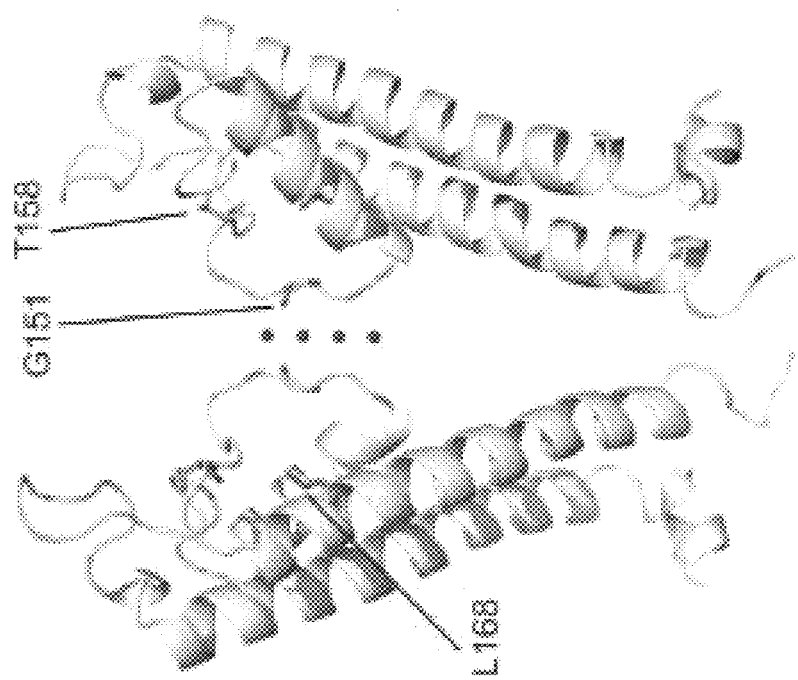
FIGS. 2A-2C, depicts the location of human mutations in KCNJ5 mapped onto the crystal structure of chicken K+ channel KCNJ12 (Tao et al., 2009, Science 326:1668).
Figure 2B:
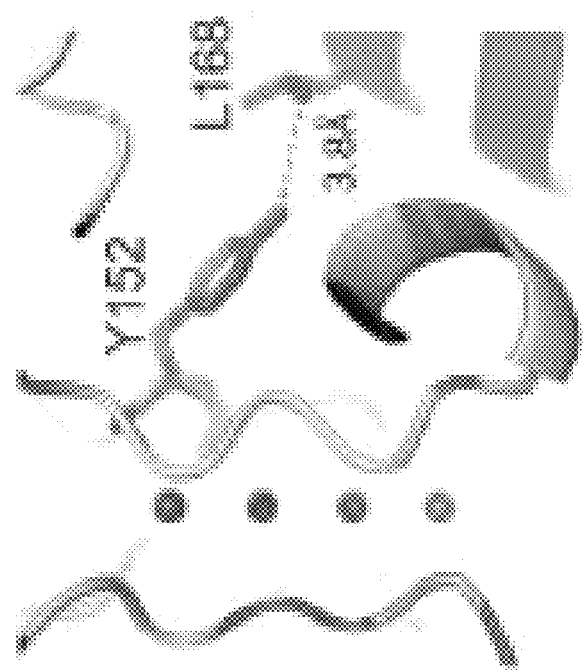

The crystal structures of a number of K+ channels have been determined, and the general features are highly conserved (Doyle et al., 1998, Science 280:69); the closest to KCNJ5 is chicken KCNJ12, another inward rectifier (Tao et al., 2009, Science 326:1668). The wild-type amino acids, G151 and L168, lie at highly conserved positions, which were mapped onto the KCNJ12 structure. G151 is the first glycine of the GYG motif of the K+ channel selectivity filter (FIGS. 1D and 2A); glycine at this position is found in virtually every K+ channel in the biological world (Heginbotham et al., 1994, Biophys. J. 66:1061; Roux, 2005, Annu. Rev. Biophys. Biomol. Struct. 34:153). The main chain carbonyl groups of G151 face the pore in the channel tetramer (FIG. 2A), and their distances from one another approximate the distances of oxygen atoms in the hydration shell surrounding K+ ions, stripping water from the ion (Doyle et al., 1998, Science 280:69; Tao et al., 2009, Science 326:1668). L168 is also conserved among KCNJ5 orthologs and inward rectifiers (FIG. 1D). L168 lies in the second transmembrane domain (inner helix) of KCNJ5; its side chain abuts the highly conserved tyrosine side chain of the GYG motif (FIG. 2B).

Figures 3A, 3B:
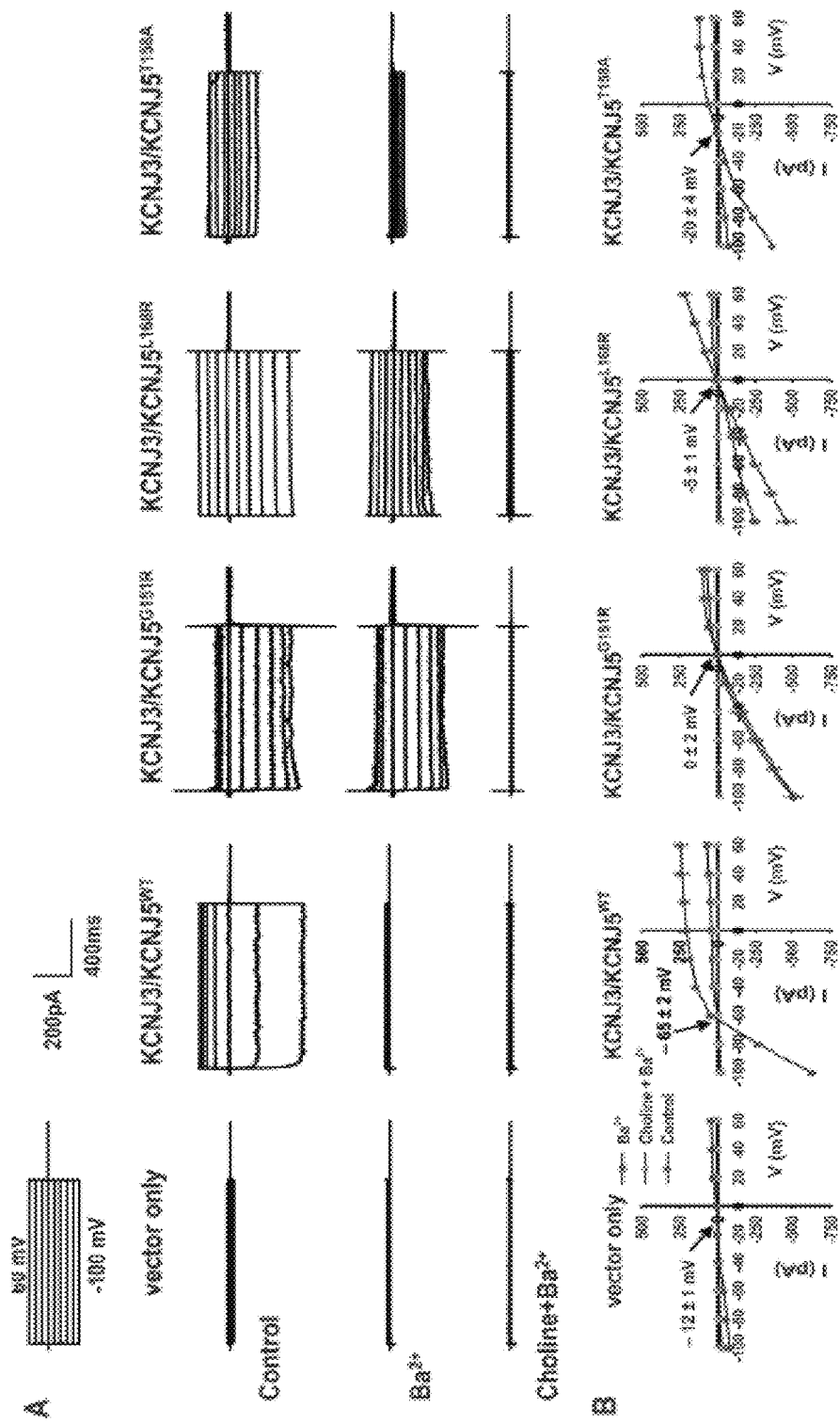
FIGS. 3A-3C, depicts the results of experiments demonstrating that KCNJ5 mutations result in loss of channel selectivity and membrane depolarization.
Figure 3C:
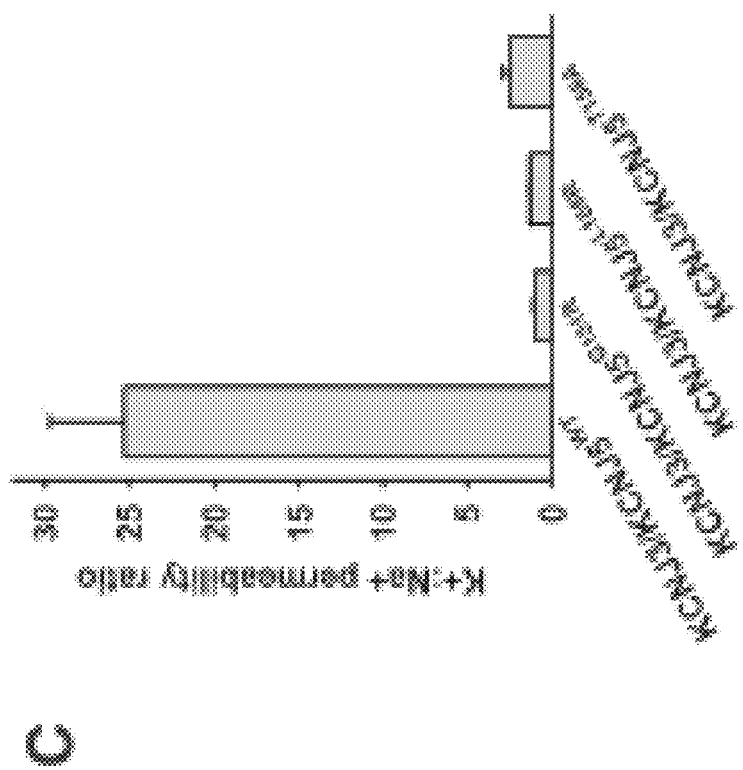
Figure 11:
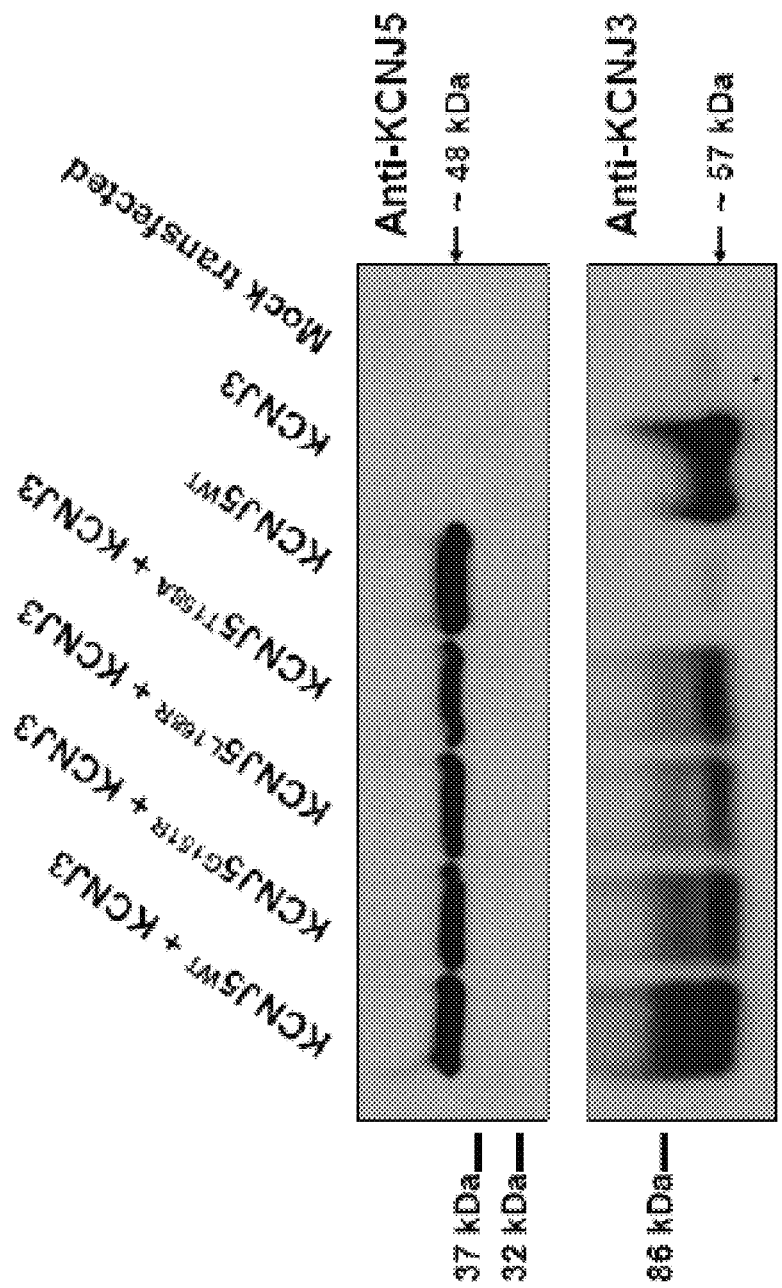
FIG. 11 depicts the results of experiments assessing KCNJ5 expression in transiently transfected 293T cells. Lysates of 293T cells transfected with WT or mutant KCNJ5 and/or KCNJ3, or mock-transfected cells, were denatured, fractionated by SDS-PAGE, transferred to membranes and incubated with antibodies to KCNJ5 (top) or anti-KCNJ3 (bottom). Monomeric KCNJ5 is detected as a single band at the calculated molecular weight of ~48 kDa, while monomeric KCNJ3 shows 2 species—one of ~57 kDa and a second, presumably glycosylated version that migrates with an apparent molecular weight of 86 kDa (Bettahi et al., 2002, J Biol Chem 277:48282-48288).

Previous studies have shown that mutations in and near K+ channel selectivity filters can alter channel selectivity to produce nonselective cation channels (Heginbotham et al., 1994, Biophys. J. 66:1061; Dibb et al., 2003, J. Biol. Chem. 278:49537). KCNJ5 exists both as homotetramers and heterotetramers with KCNJ3 (KCNJ3 is inactive as a homotetramer) (Corey and Clapham, 1998, J. Biol. Chem. 273: 27499); heterotetramers are more active than homotetramers, and activity can be increased by activation of GPCRs such as dopamine D2 (Krapivinsky et al., 1995, Nature 374:135; Gregerson et al., 2001, Endocrinology 142:2820). Both KCNJ5 and KCNJ3 are expressed in human adrenal cortex (FIG. 17). Wild-type or mutant KCNJ5 with KCNJ3 were expressed in 293T cells (FIGS. 3 and 11) and currents at voltages from −100 mV to +60 mV were measured using perforated whole-cell recording with physiologic solutions including 140 mM K+ inside and 5 mM K+, 140 mM Na+ outside the cell. KCNJ3/KCNJ5WT induced a robust inwardly rectifying Ba2+-sensitive current that hyperpolarized the membrane with a reversal potential of −65±2 mV (FIG. 3).

Figures 4A, 4B, 4C:
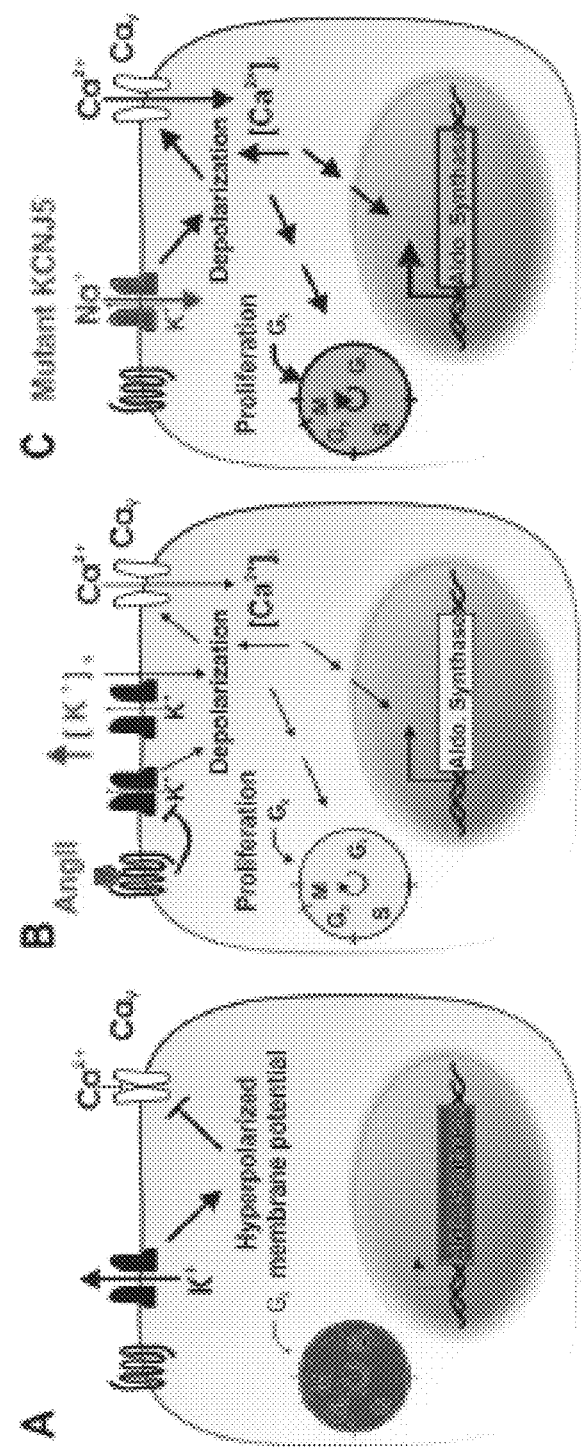
FIGS. 4A-4B, depicts schematics of the proposed mechanism underlying aldosterone-producing adenoma and Mendelian aldosteronism. As depicted in FIG. 4a, adrenal glomerulosa cells have a high resting K+ conductance, which produces a highly negative membrane potential (Spät, 2004, Mol. Cell. Endocrinol. 217:23). As depicted in FIG. 4B, membrane depolarization by either elevation of extracellular K+ or closure of K+ channels by angiotensin II activates voltage-gated Ca2+ channels, increasing intracellular Ca2+ levels (Spät and Hunyady, 2004, Physiol. Rev. 84:489). This provides signals for increased expression of enzymes required for aldosterone biosynthesis, such as aldosterone synthase, and for increased cell proliferation. As depicted in FIG. 4C, channels containing KCNJ5 with G151R, T158A, or L168R mutations conduct Na+, resulting in Na+ entry, chronic depolarization, constitutive aldosterone production, and cell proliferation.
Figures 12A, 12B:
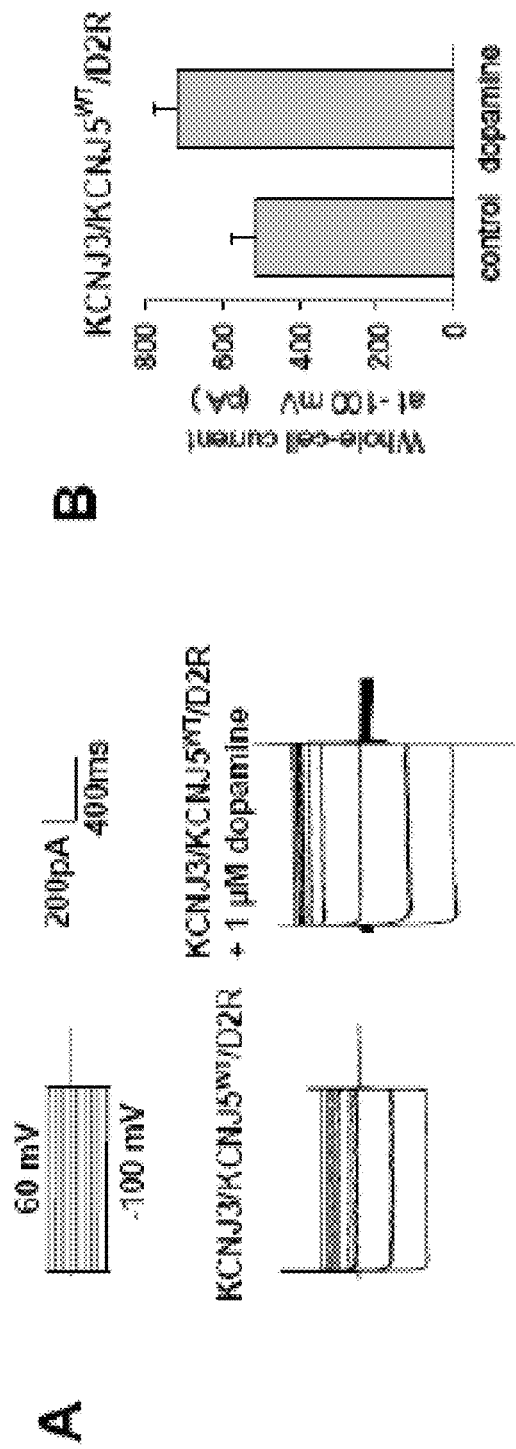
FIGS. 12A-12D, depicts the results of experiments assessing the effect of dopamine and choline substitution on current in 293T cells.
Figures 12C, 12D:
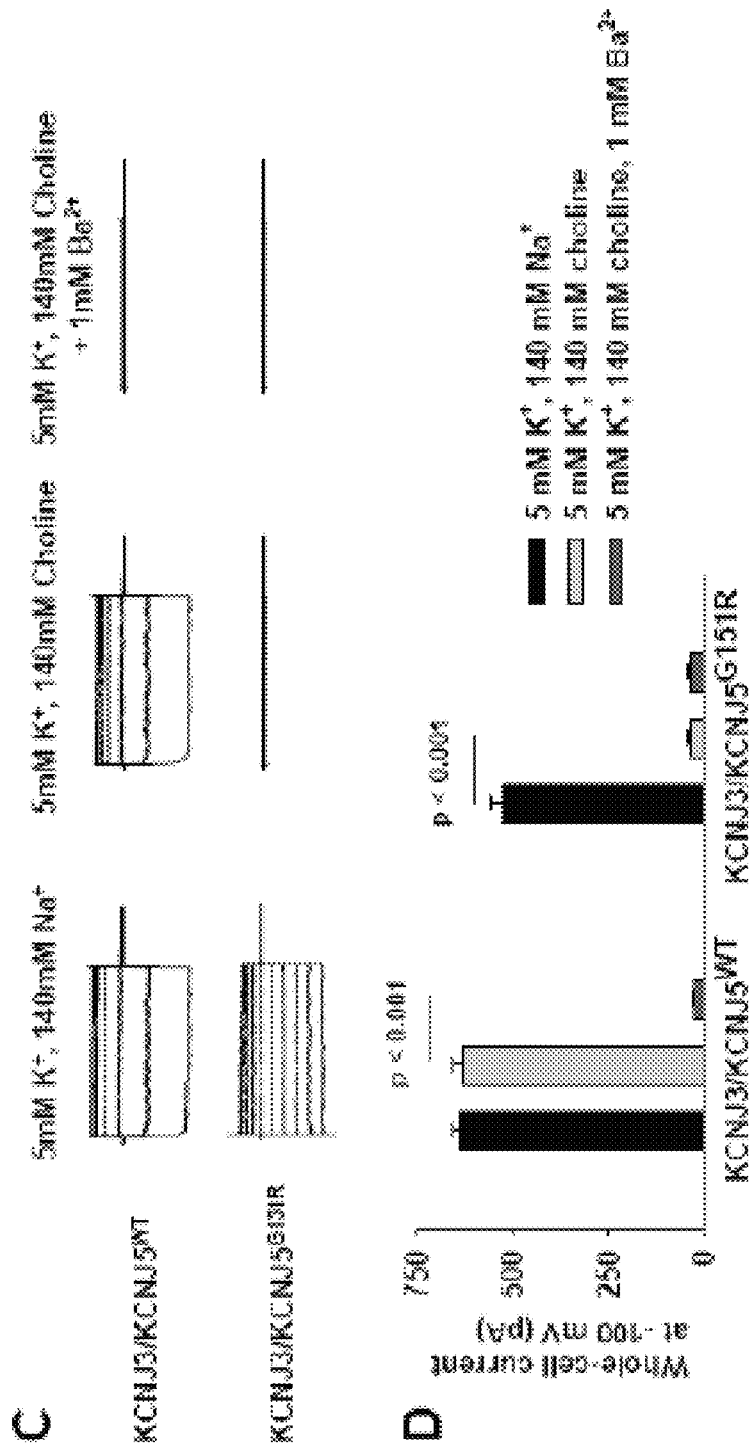
Figures 13A, 13B:
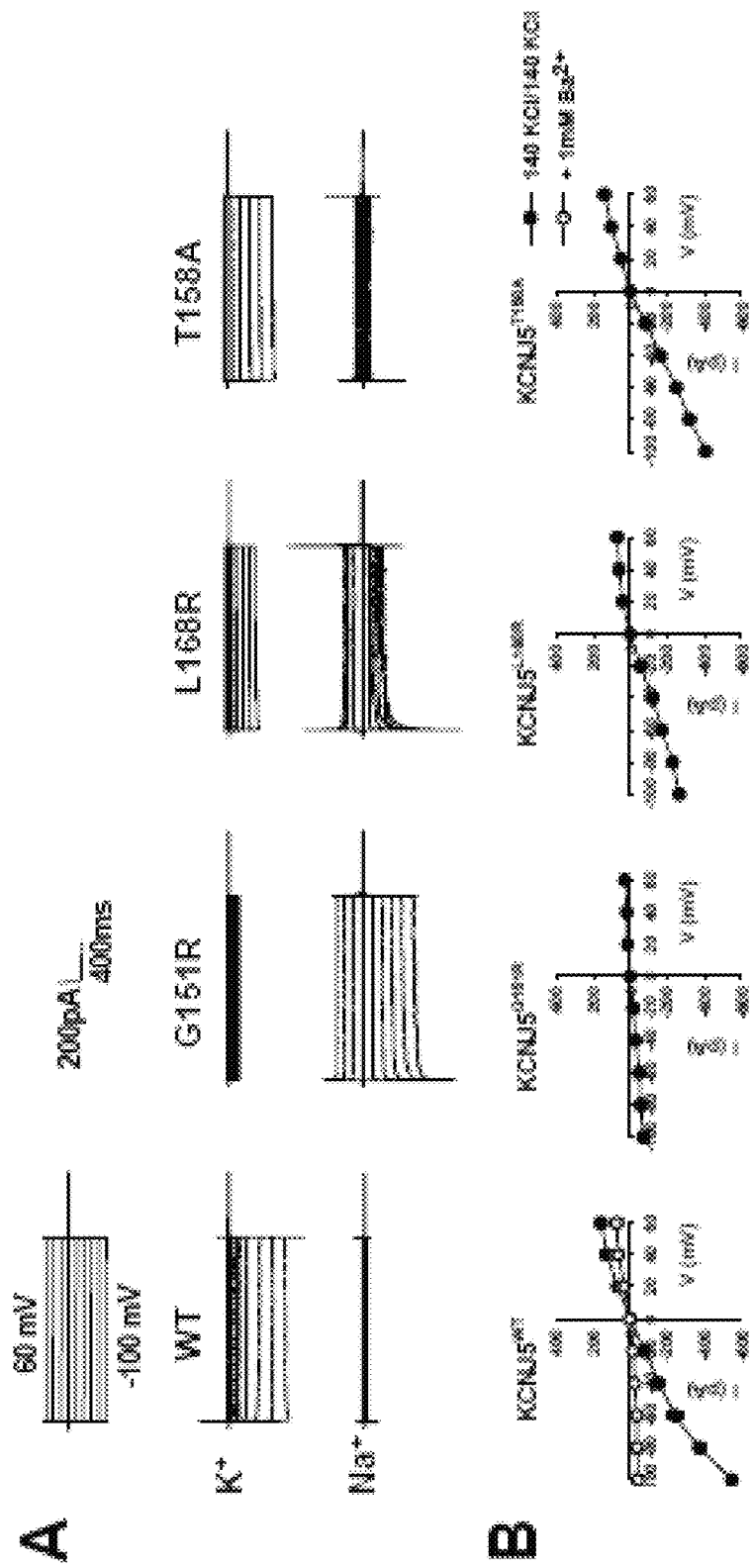
FIGS. 13A-13F, depicts the results of experiments demonstrating that mutations in KCNJ5 homotetramers increase $Na^+$ conductance. Because of low current amplitude of homotetrameric channels, currents were measured under symmetrical high Na+ or high K+ conditions, which increases current amplitude (Owen et al., 1999, Exp Physiol 84:471-488; Andreoli, et al., Eds., Molecular Biology of Membrane Transport Disorders (Plenum Press, New York, ed. 2, 1996), chap. 5) (FIGS. 13A-13D); reversal potentials and permeability ratios were determined using physiological solutions (FIGS. 13E, 13F).
Figures 13C, 13D, 13E, 13F:
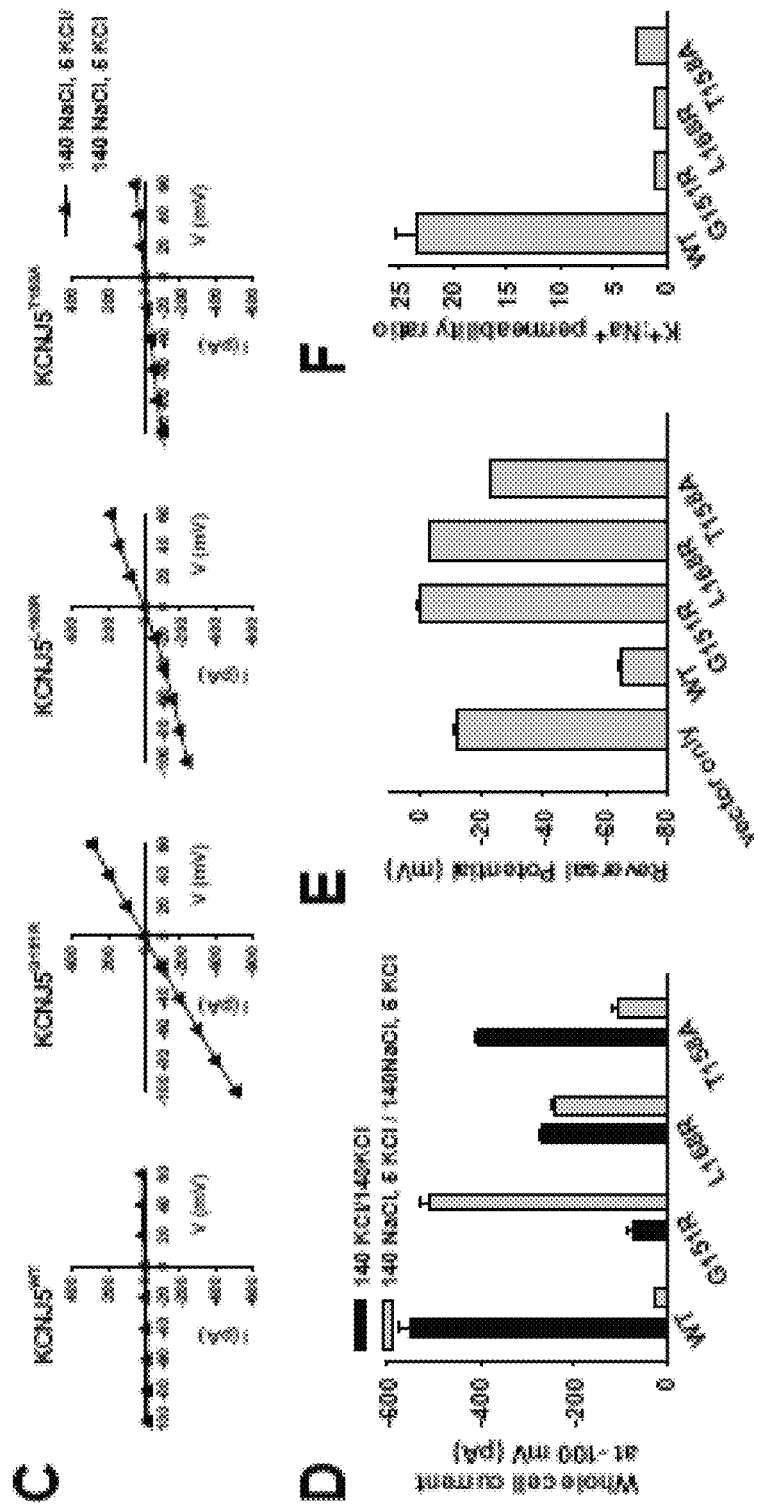
Figure 20A:
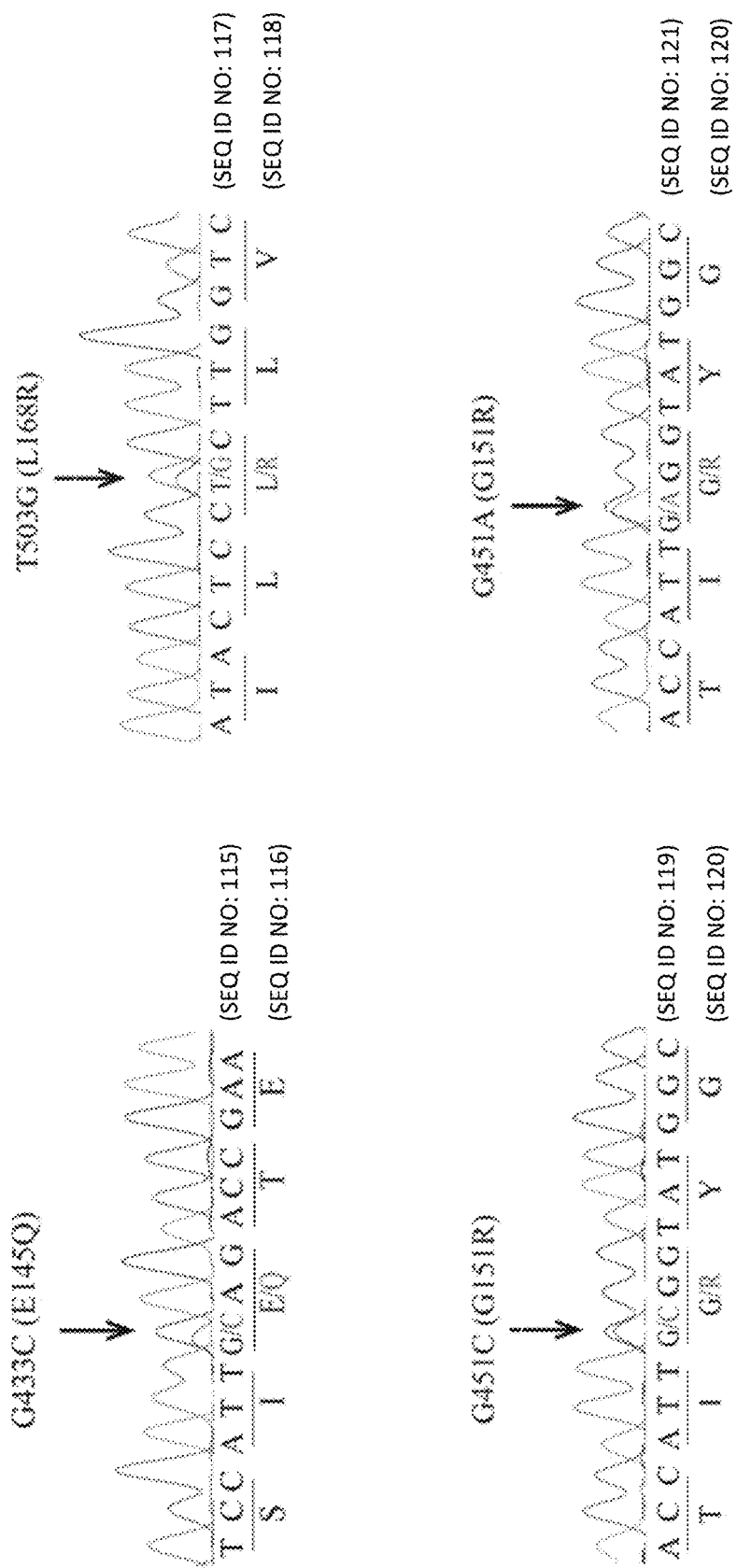
FIGS. 20A-20B, depicts Sanger traces from 4 tumor samples with somatic mutations E145Q, G151R and L168R in KCNJ5 (FIG. 20A) and mutation spectrum and gender distribution (FIG. 20B).
Figure 20B:
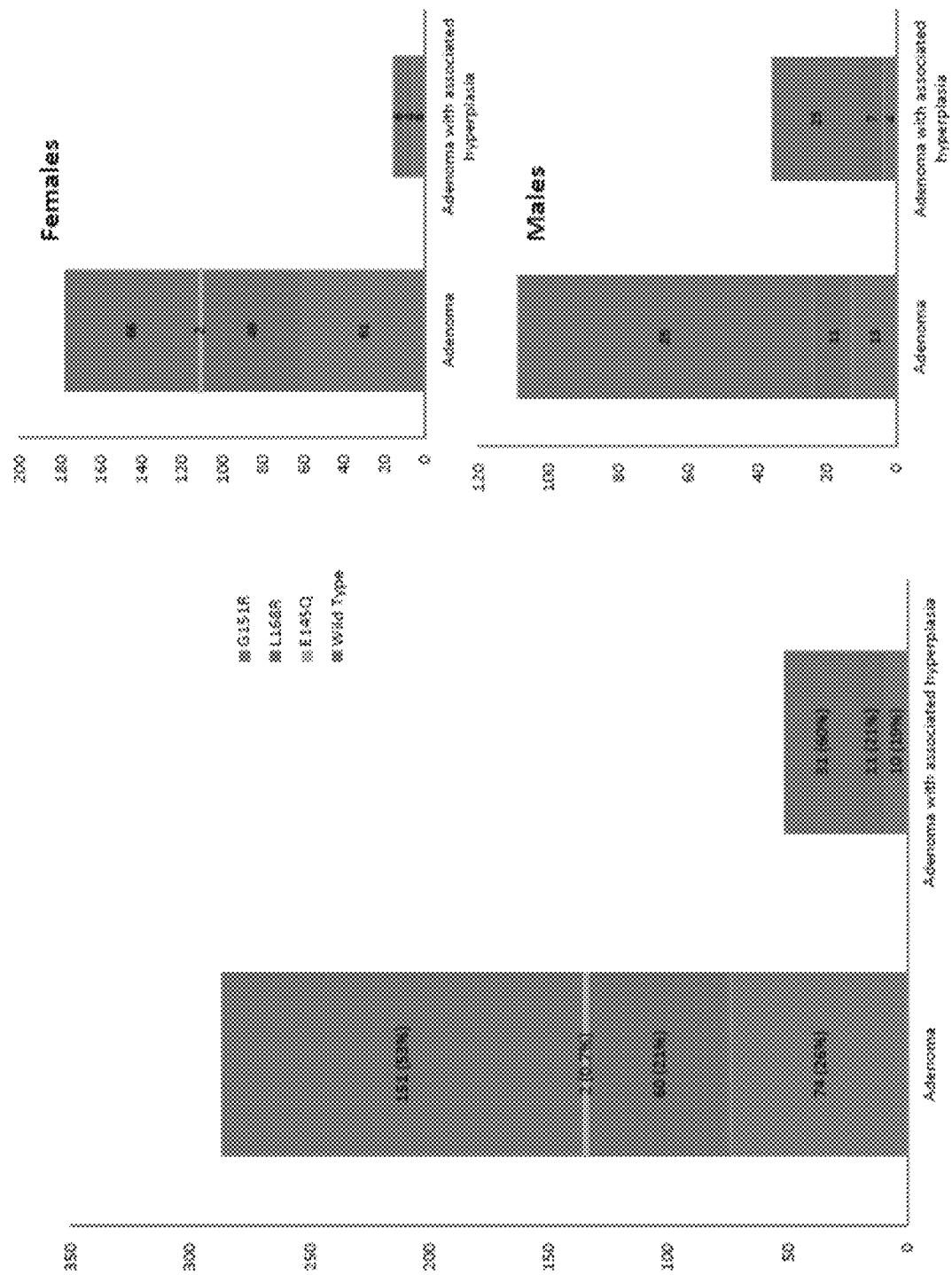

Coexpression with the dopamine D2 receptor and addition of dopamine increased current by ~50% (FIGS. 12A and 12B). These are all characteristic features of KCNJ3/KCNJ5 heterotetramers (Krapivinsky et al., 1995, Nature 374:135). The K+:Na+ permeability ratio, estimated from the Goldman equation, was 25.3±4.4:1. In contrast, KCNJ3/KCNJ5G151R channels produced currents that showed loss of inhibition by Ba2+ and membrane depolarization with a shift of the reversal potential to 0±2 mV. This depolarization is attributable to increased Na+ conductance: whereas substitution of choline for Na+ had no effect on the WT channel, elimination of Na+ markedly inhibited KCNJ3/KCNJ5G151R currents either with (FIG. 3) or without (FIGS. 12C and 12D) Ba2+. The calculated K+:Na+ permeability ratio is diminished to 1.0±0.1:1, consistent with loss of channel selectivity. This loss of ion selectivity is similar to effects seen with other selectivity filter mutations (Heginbotham et al., 1994, Biophys. J. 66:1061). KCNJ3/KCNJ5L168R channels behave similarly, producing a reversal potential of −5±1 mV and a K+:Na+ permeability ratio of 1.3±0.1:1 (FIG. 3). Similar results were obtained with KCNJ5 homotetramers (FIG. 13). In glomerulosa cells, membrane depolarization activates voltage-gated Ca2+ channels, increasing intracellular Ca2+, thereby increasing aldosterone production (FIG. 4). Similarly, chronic Ca2+ stimulation promotes increased proliferation in glomerulosa (McEwan et al., 1996, Am. J. Physiol. 271, E192; Pawlikowski et al., 2001, Endocr. Regul. 35:139; Tanabe et al., 1998, J. Endocrinol. Invest. 21:668) and other cell types (Kahl and Means, 2003, Endocr. Rev. 24:719; Roderick and Cook, 2008, Nat. Rev. Cancer 8:361), which can account for clonal expansion of cells harboring these somatic mutations and adenoma formation.

Figure 2C:
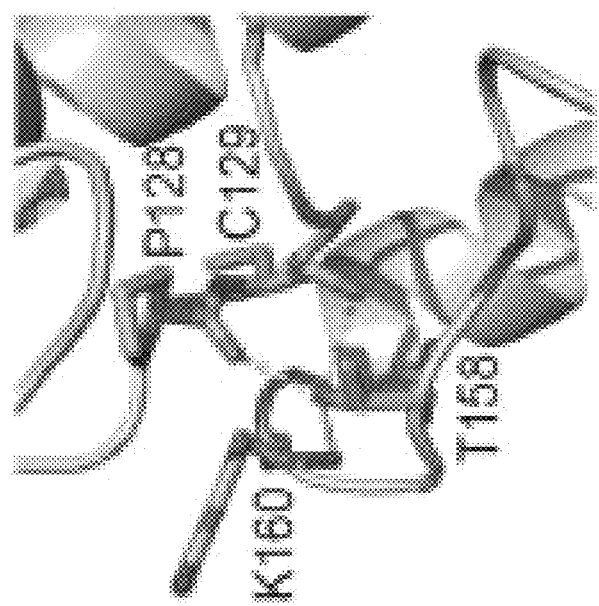
Figures 9G, 9H, 9I:
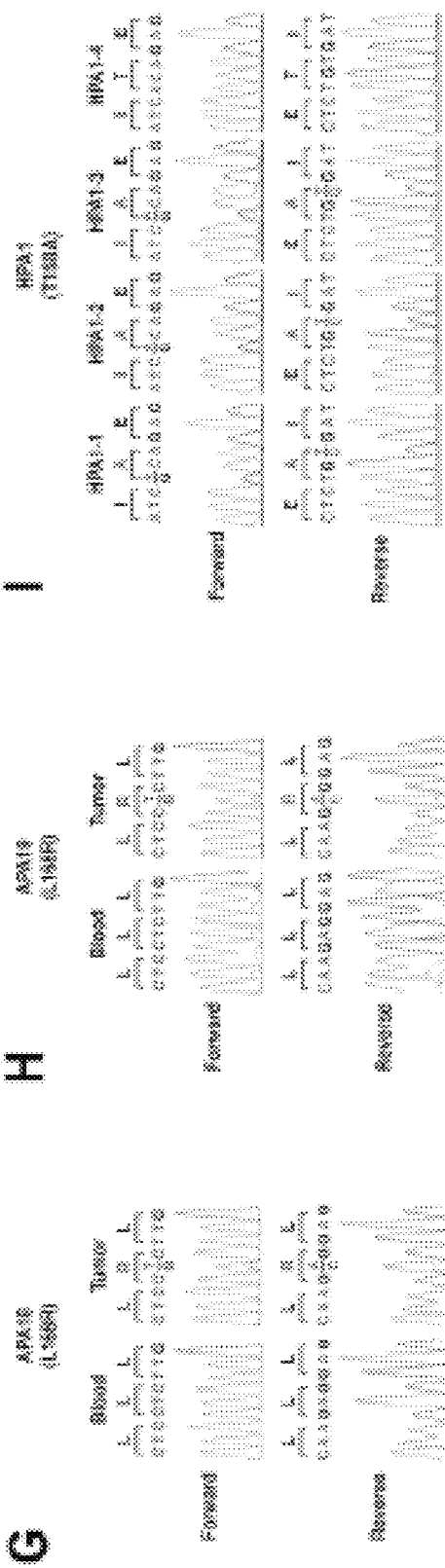
Figure 10:
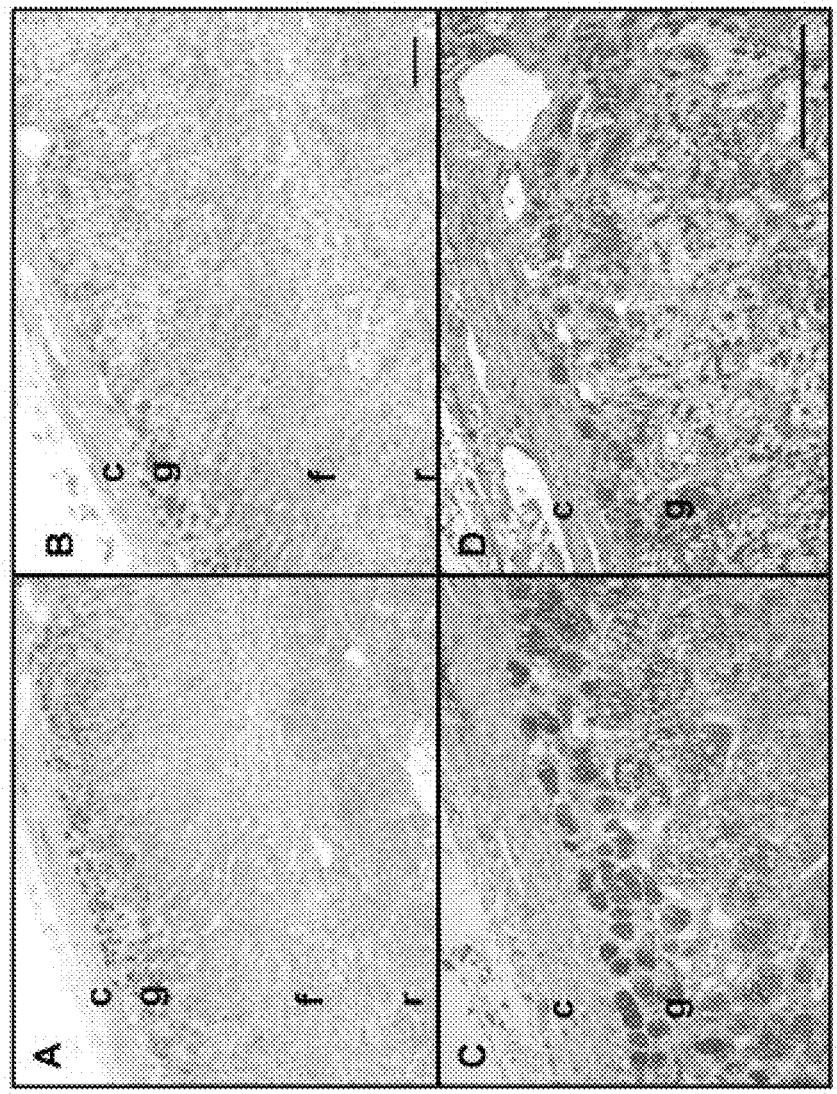
FIG. 10, comprising

These inferences from somatic mutations in tumors suggest that inherited mutations in KCNJ5 with similar effect could cause a Mendelian form of primary aldosteronism with bilateral adrenal hyperplasia, because in this case every adrenal cell would harbor the mutation. Recently described was just such a syndrome of unknown cause in a father and his two daughters who were all diagnosed between ages 4 and 7 with severe hypertension, aldosteronism, and massive adrenal hyperplasia (FIG. 10) (Geller et al., 2008, J. Clin. Endocrinol. Metab. 93:3117). All three individuals had a radical intervention, bilateral adrenalectomy in childhood. Pathology demonstrated massive hyperplasia of the adrenal cortex (paired adrenal weights up to 81 g; normal<12 g). The sequence of KCNJ5 identified a heterozygous T158A mutation that cosegregated with the disease (FIGS. 1C and 9I). This variant is absent in the dbSNP and 1000 Genomes databases and in 900 control alleles. This threonine is conserved among KCNJ5 orthologs and other inward rectifiers (FIG. 1D) and lies in the loop between the selectivity filter and the second transmembrane domain; its hydroxyl group hydrogen bonds with conserved residues in the loop between the first transmembrane domain and the pore helix, constraining the structure (FIG. 2C). The T158A mutation eliminates these hydrogen bonds. Similar to the other mutations, KCNJ3/KCNJ5T158A channels showed reduced selectivity (K+:Na+ permeability ratio of 2.5±0.4:1) and membrane depolarization, with a reversal potential of −20±4 mV (FIG. 3B). Similar results were seen in homotetramers (FIG. 13).

The findings described herein implicate inherited and acquired mutations in KCNJ5 in aldosteronism associated with cell autonomous proliferation. The very small number of somatic mutations observed, the young age of many APA subjects with KCNJ5 mutations (four of eight under age 35), and Mendelian transmission of the inherited syndrome are consistent with the KCNJ5 mutations being sufficient for both constitutive aldosterone secretion and cell proliferation. The increased Na+ conductance and membrane depolarization resulting from these mutations implicate activation of voltage-gated Ca2+ channels in the pathophysiologic mechanism (FIG. 4) (Spät and Hunyady, 2004, Physiol. Rev. 84:489; McEwan et al., 1996, Am. J. Physiol. 271, E192; Pawlikowski et al., 2001, Endocr. Regul. 35:139; Tanabe et al., 1998, J. Endocrinol. Invest. 21:668). The effects of these mutations in and near the selectivity filter to reduce channel selectivity are consistent with previous in vitro studies (Heginbotham et al., 1994, Biophys. J. 66:1061; Dibb et al., 2003, J. Biol. Chem. 278:49537). In addition, mutation of the homologous glycine to serine in KCNJ6 in the weaver mouse also produces a Na+-conducting channel, leading to selective loss of neurons in cerebellum and substantia nigra (Navarro et al., 1996, Science 272:1950). Glomerulosa cells have constitutively open "leak" K+ channels and a high Na+/K+ adenosine triphosphatase activity (Hajnoczky et al., 1992, Endocrinology 130:1637); such differences may contribute to different fates in these cell types.

Because mutations in and near K+ channel selectivity filters can alter ion selectivity (Dibb et al., 2003, J. Biol. Chem. 278:49537), the restricted spectrum of mutations found in APAs is noteworthy. Although not wishing to be bound by any particular theory, one possible explanation is that mutant channels cause sufficient Na+ permeability for tumor development, but not so great as to cause cell death (Roderick and Cook, 2008, Nat. Rev. Cancer 8:361; Navarro et al., 1996, Science 272:1950); these requirements may restrict the mutational spectrum. The lower relative Na+ permeability observed with the inherited T158A mutation is consistent with allelic variation in effect. It will be of interest to determine the prevalence and spectrum of KCNJ5 mutations in other cohorts of patients with APAs and with unexplained aldosteronism.

These findings also raise the question of the normal role of KCNJ5 in glomerulosa cells. In rodent and cow, members of the "leak" K+ channel family (KCNK2, KCNK3, and KCNK9) appear to set the resting potential (Enyeart et al., 2002, J. Biol. Chem. 277:49186; Czirják and Enyedi, 2002, Mol. Endocrinol. 16:621). Dopamine, an inhibitor of aldosterone release, increases activity of K+ channels containing KCNJ5 (Gregerson et al., 2001, Endocrinology 142:2820), which suggests that KCNJ5 may normally inhibit aldosterone production. KCNK2, KCNK3, and KCNK9 were sequenced in the tumor cohort and no mutations were found, which is consistent with the explanation that KCNJ5 has a privileged role in producing APA.

Lastly, the findings described herein demonstrate a role for ion channel mutations in neoplasia. The distinct mechanism of these KCNJ5 mutations may be related to the benign nature of these tumors. It will be of interest to determine whether other endocrine neoplasias have related mutations that account for concomitant cell proliferation and hormone release. Mutations in other K+ channel genes have been identified in various human cancers, but their importance is uncertain. These include mutations altering conserved residues in or near voltage-regulating segments in KCNB2, KCNC2, and KCNQ5 from glioblastoma, breast cancer, and colorectal cancers (Wood et al., 2007, Science 318:1108; Sjöblom et al., 2006, Science 314:268; Parsons et al., 2008, Science 321:1807). Investigation of the functional consequences of these mutations will be of interest.

Example 2: KCNJ5 Gene Mutation Prevalence and Spectrum in Adrenal Aldosterone Producing Lesions The findings described herein confirm and extend the finding of recurrent mutations in KCNJ5 as a prevalent cause of APA. Previously described mutations resulting in G151R and L168R were found in similar frequencies that together comprise 46% of APAs. In addition, as described herein, two instances of a previously unidentified mutation, E145Q. Like the other mutations, this mutation lies near the selectivity filter and therefore likely to increase Na+ conductance. Although not wishing to be bound by any particular theory, the increase in Na+ conductance may explain why a number of patients show an increase in PAC despite volume load and suppression of renin in saline infusion tests. In addition, one KCNJ5 mutation was found in an aldosterone-secreting adrenocortical carcinoma. These findings demonstrate that the G151R and L168R mutations account for nearly 99% of KCNJ5 mutations in APAs and suggest that few additional mutations in this gene are unlikely to account for significant fractions of APA.

KCNJ5 mutations were prevalent in tumors in which there was a solitary or dominant nodule; these tumors were of variable size (6-47 mm) at the time of surgery and patients with and without mutations generally had surgery at similar ages. This was true in both the presence and absence of surrounding hyperplasia. In contrast, no KCNJ5 mutations were found among 9 cases prospectively classified as unilateral hyperplasia with or without multiple nodules despite analyzing DNA from most of available nodules in each sample (p<0.005 for difference in frequency compared with all APAs). Similarly, no KCNJ5 mutations were found in other non-aldosterone secreting adrenal lesions, demonstrating their specificity for aldosteronism. These observations support a distinct pathophysiology of APA with hyperplasia and unilateral hyperplasia without a dominant nodule.

Most interestingly, there was a striking gender dimorphism in the prevalence of KCNJ5 mutations. APAs have consistently been found to be more prevalent in women than men with a ratio of about 2:1 (Sawka et al., 2001, Ann Intern Med. 135:258-261). It appears that this entire excess can be accounted for by the increased prevalence of KCNJ5 mutations among APAs in women compared to men since a 2.6-fold increase in the prevalence of KCNJ5 mutations in female compared to male APAs was observed. APAs without KCNJ5 mutations actually had a higher prevalence in males than females in the cohort. Whether this gender bias for KCNJ5 mutation is attributable to a difference in the rate at which these mutations occur in females vs. males, or to differences in the likelihood of tumors developing following mutation, will be of interest to determine.

The materials and methods used in this Experimental Example are now described.

Patients

Histopathological adrenocortical specimens were collected from 348 patients with clinically diagnosed primary aldosteronism, subjected to adrenalectomy at 10 different hospitals, Uppsala and Stockholm, Sweden; Hamburg, Lübeck, Düsseldorf, Essen, and Halle, Germany; Sydney, Australia; Lyon and Poitiers, France. The clinical diagnosis had been established by raised aldosterone/renin ratio together with positive confirmatory tests and lateralisation studies (CT, MRI and adrenal vein sampling) according to the routine protocols at the various centers. The samples were collected from patients with unilaterally dominant lesions based on preoperative lateralization studies, and confirmed by histopathology. The histopathologic diagnosis had been confirmed by expert endocrine pathologists at the different centers. The specimens were categorized into 1) adenoma (without marked associated hyperplasia) 2) adenoma with marked associated hyperplasia, 3) merely hyperplasia of micro- or macronodular type. In addition, three adrenocortical carcinomas with aldosterone excess were included in this study. Informed consent and approval from local ethical committees were obtained.

130 non aldosterone secreting adrenocortical tumors (FIG. 23) collected at surgery in Uppsala, were also subjected to study.

DNA and RNA Extraction, RT-PCR and Immunohistochemistry

DNA, RNA extraction and subsequent cDNA synthesis were done as previously described (Bjorklund et al., 2007, PLoS Med. 4:e328). Briefly DNA and RNA were prepared from cryosections using DNeasy Blood & Tissue Kit (Qiagen) or FFPE sections using AllPrep DNA/RNA FFPE Kit (Qiagen). Sections (6 µm) were stained with hematoxylin-eosin to verify presence of tumor cells prior to mutation analysis. From available specimens with clear distinguishable nodules or small adenomas (n=41), punched needle biopsies (n=78) were obtained from different areas of the specimens to investigate small adenomas, macronodules, as well as areas with micronodular, or diffuse hyperplasia for mutation analysis. Reverse transcription of RNA was performed with random hexamer primers using the First-Strand cDNA Synthesis kit (GE Healthcare) according to the manufacturer's instructions. PCR reactions were performed using primers and conditions described.

```
Fragment 1, intron 1-2:
                                       (SEQ ID NO: 14)
CTAGTGAATCAGAACAGCCCAC Fragment 1, exon 2:
                                       (SEQ ID NO: 15)
AAGGAATCCACTCTTGGTCG Fragment 2, exon 2:
                                       (SEQ ID NO: 16)
GCTTCATTTGGTGGCTCATT Fragment 2, exon 2:
                                       (SEQ ID NO: 17)
CCACCATGAAGGCATTGAC Fragment 3, exon 2:
                                       (SEQ ID NO: 18)
GTGTCCGCTTTCCTGTTCTC
```

```
-continued
Fragment 3, intron 2-3:
                                       (SEQ ID NO: 19)
CTAAGTCTGAAGTGTAGGTAG Fragment 4, intron 2-3:
                                       (SEQ ID NO: 20)
AATGGATGGATAGATGGATGG Fragment 4, exon 3:
                                       (SEQ ID NO: 21)
GTCTGTGTTCACTGAAGCCA Verification, exon 2:
                                       (SEQ ID NO: 22)
CGACCAAGAGTGGATTCCTT Verification, exon 2:
                                       (SEQ ID NO: 23)
AGGGTCTCCGCTCTCTTCTT cDNA, exon 2:
                                       (SEQ ID NO: 24)
GCTTCATTTGGTGGCTCATT cDNA, exon 3:
                                       (SEQ ID NO: 25)
GTCTGTGTTCACTGAAGCCAG
```

RT-PCR of KCNJ5 was performed using mRNA specific primers.

KCNJ5 protein expression was investigated in 64 specimens by immunohistochemistry as previously described (Choi et al., 2011, Science 331:768-772).

DNA Sequencing

All KCNJ5 coding exons with intron/exon junctions were directly sequenced (Beckman Coulter Genomics, Tackeley, UK) and traces were analyzed using CodonCode Aligner software (CodonCode Corporation, Dedham, Mass.). Orthologs. Protein sequences were aligned using the ClustalW algorithm. GenBank accession numbers were: NP_000881.3 (human), NP_034735.3 (mouse), XP_417864.2 (chicken), NP_001016901.1 (frog), XP_700619.4 (zebrafish), and XP_002122831.1 (tunicate).

Statistical Analysis

Data is presented as arithmetical mean and range. Mann Whitney U test, ANOVA (mixed model, two groups based on absence or presence of KCNJ5 mutations), or Chi square test was used for statistical analysis. A p value of <0.05 was considered significant.

The results of this Experimental Example are now described.

Figure 21:
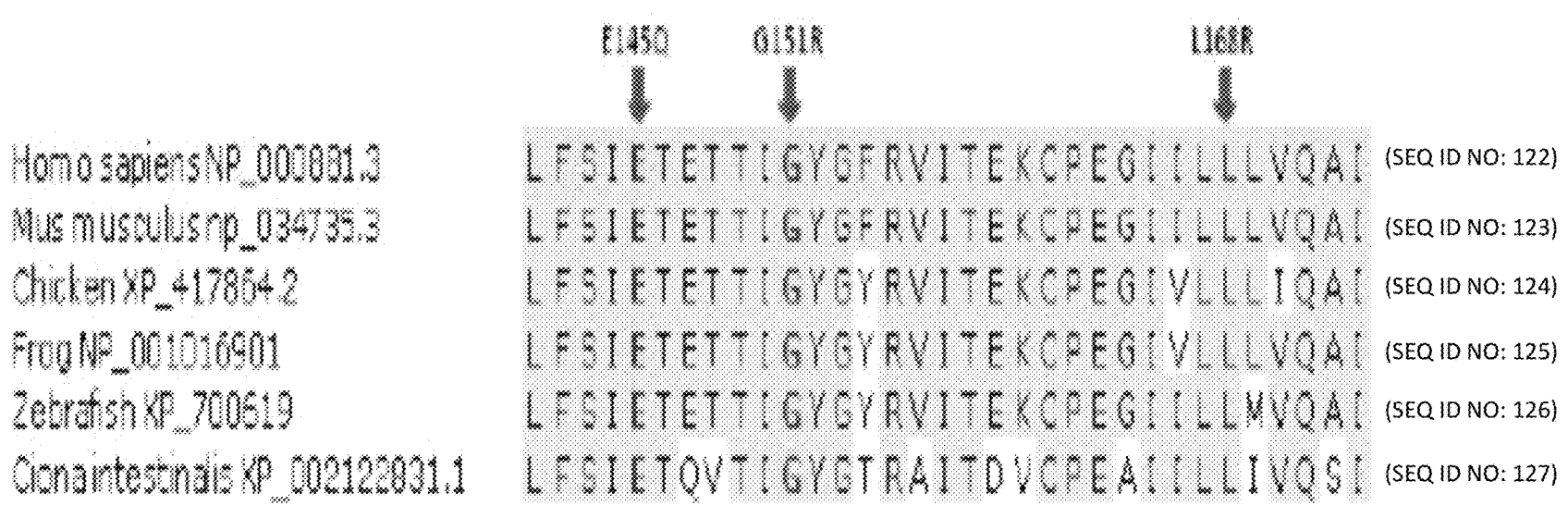

In total, KCNJ5 mutations were identified in 157 of 348 (45%) of aldosterone producing lesions (FIG. 19). Of these, 155 resulted in the previously reported G151R and L168R substitutions (found in 24% and 20% of all samples, respectively). In addition, two APAs had a single base substitution resulting in a novel E145Q mutation located near the selectivity filter at a highly conserved position (FIG. 21). The L168R mutation was observed in one of three adrenocortical carcinomas with excess aldosterone production. In all 137 cases in which matched DNA from blood or surrounding normal tissue was available, KCNJ5 mutations were specific to adenomas, consistent with these representing somatic mutations.

Stratifying by lesion type, 136 mutations were found in 287 APAs in which surrounding hyperplasia was not found (47%). Twenty-one mutations were identified in 52 adenomas in which surrounding hyperplasia was observed (40%); in 41 specimens punch biopsies of hyperplastic surrounding tissue did not show KNCJ5 mutations. No KCNJ5 mutations were found in 9 specimens with hyperplasia without APA, including sampling selected macronodules of variable size from the same lesion (FIG. 19). KCNJ5 mutation (L168R) was also found in one of three aldosterone-secreting adrenocortical carcinomas (33%). In contrast, no KCNJ5 mutations were detected in 130 non-aldosterone secreting adrenocortical specimens (FIG. 23).

Genotype-phenotype correlation demonstrated a dramatic difference in the prevalence of KCNJ5 mutations in women and men. While KCNJ5 mutations were found in 63% of APA's without surrounding hyperplasia in women (112/178), they were present in only 22% of APA's in males (24/109) (FIG. 19). This difference, a 2.9:1 risk ratio in females versus males, is statistically significant ($p=10-11$). A similar female bias for KCNJ5 mutations was seen among APAs with surrounding hyperplasia (ratio 2.0:1).

Females with and without KCNJ5 mutations had surgery at similar ages and their adenomas were of similar size at surgery (FIG. 19). Males with KCNJ5 mutations were an average of 9 years younger at the age of surgery than those without (45 vs. 54, respectively; $p<0.005$). Male APAs with KCNJ5 mutations were on average 1 cm larger than those without (27.1 mm vs. 17.1 mm; $p<0.005$); this was attributable to males with G151R mutations having the largest APAs.

Figures 22A, 22B:
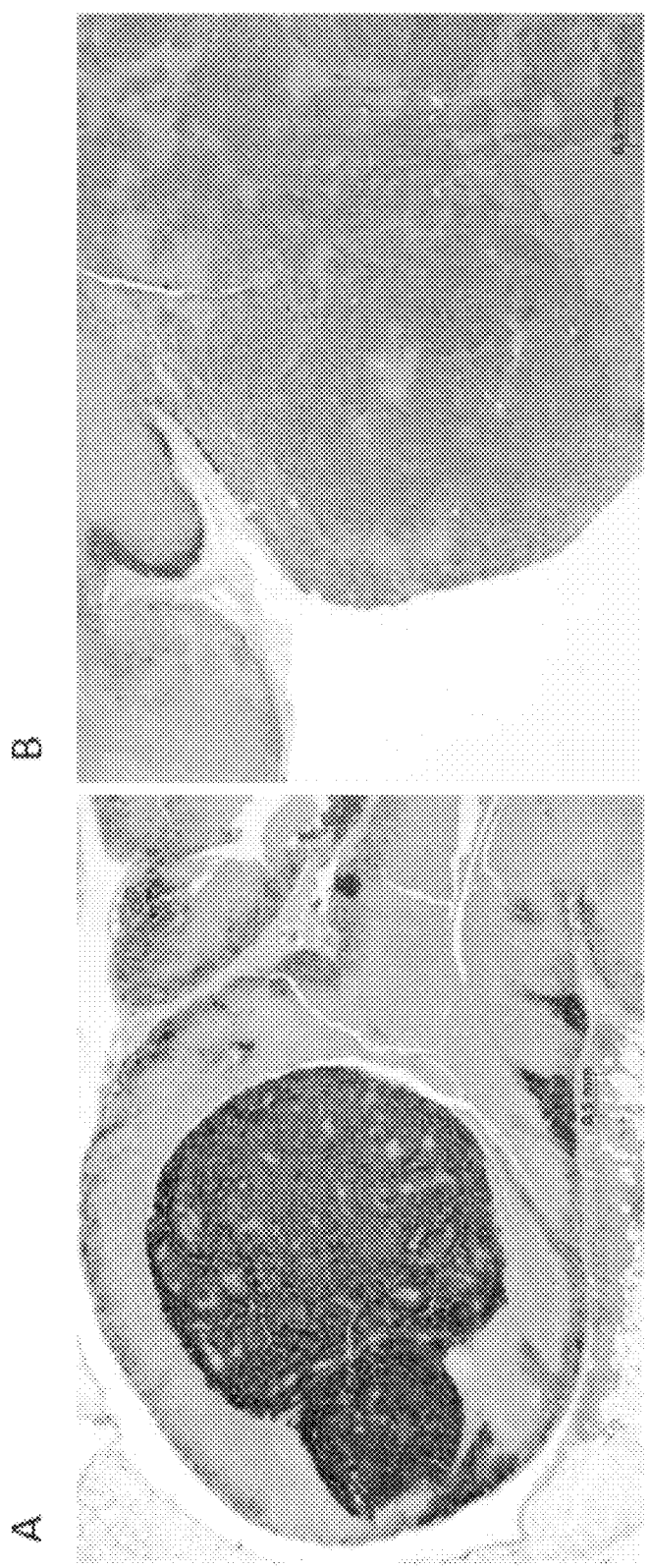
FIGS. 22A-22B depicts the results of experiments demonstrating intense KCNJ5 reactivity in a 4 mm macronodule (FIG. 22A) and moderate KCNJ5 reactivity in a 19 mm large adenoma (FIG. 22B).

All lesions examined expressed the mutated allele at the mRNA level as demonstrated by reverse transcriptase PCR using mRNA-specific primers. KCNJ5 staining using specific antibodies were variable in both adenomas and adenoma-like macronodules, showing intense, weak or heterogeneous staining. This was not correlated to KCNJ5 mutation status (FIG. 22).

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of diagnosing and treating an adrenal disease or disorder in a human subject in need thereof, the method comprising:
   a. detecting at least one mutation in the subject's KCNJ5 sequence in a biological sample of the subject, wherein said at least one mutation is G151R, L168R, T158A or E145Q;
   b. diagnosing the subject a having an adrenal disease or disorder; and
   c. administering to the subject a treatment for the adrenal disease or disorder.

2. The method of claim 1, wherein the subject's KCNJ5 sequence is a nucleic acid sequence, and wherein the nucleic acid sequence encodes a polypeptide.

3. The method of claim 1, wherein the subject's KCNJ5 sequence is an amino acid sequence.

4. The method of claim 1, wherein said step of detecting at least one mutation in the subject's KCNJ5 sequence employs PCR.

5. The method of claim 1, wherein the biological sample is at least one selected from the group consisting of: blood, plasma, serum, a body fluid, a tissue, a tumor, and a cell.

6. The method of claim 1, wherein the adrenal disease or disorder is at least one disease or disorder selected from the group consisting of aldosteronism, primary aldosteronism, secondary aldosteronism, hyperaldosteronism, primary hyperaldosteronism, secondary hyperaldosteronism, adrenal insufficiency, Addison's Disease, adrenoleukodystrophy, pheochromocytoma, Cushing's Syndrome, adrenal hyperplasia, congenital adrenal hyperplasia, cancer, adrenal cancer, hypertension, primary hypertension, secondary hypertension and virilization.

\* \* \* \* \*

SEQUENCE LISTING

```
<160> NUMBER OF SEQ ID NOS: 127

<210> SEQ ID NO 1
<211> LENGTH: 20
<212> TYPE: DNA
<213> ORGANISM: Homo sapiens

<400> SEQUENCE: 1
cgaccaagag tggattcctt                                                   20

<210> SEQ ID NO 2
<211> LENGTH: 20
<212> TYPE: DNA
<213> ORGANISM: Homo sapiens

<400> SEQUENCE: 2
agggtctccg ctctcttctt                                                   20

<210> SEQ ID NO 3
<211> LENGTH: 20
<212> TYPE: DNA
<213> ORGANISM: Homo sapiens

<400> SEQUENCE: 3
gcttcatttg gtggctcatt                                                   20

<210> SEQ ID NO 4
<211> LENGTH: 19
<212> TYPE: DNA
<213> ORGANISM: Homo sapiens

<400> SEQUENCE: 4
ccaccatgaa ggcattgac                                                    19

<210> SEQ ID NO 5
<211> LENGTH: 20
<212> TYPE: DNA
<213> ORGANISM: Homo sapiens

<400> SEQUENCE: 5
gtgtccgctt tcctgttctc                                                   20
```

<210> SEQ ID NO 6
<211> LENGTH: 20
<212> TYPE: DNA
<213> ORGANISM: Homo sapiens

<400> SEQUENCE: 6
gagatgactg cgttgttgga                                              20

<210> SEQ ID NO 7
<211> LENGTH: 30
<212> TYPE: DNA
<213> ORGANISM: Homo sapiens

<400> SEQUENCE: 7
ccgaaacaac cattaggtat ggcttccgag                                   30

<210> SEQ ID NO 8
<211> LENGTH: 30
<212> TYPE: DNA
<213> ORGANISM: Homo sapiens

<400> SEQUENCE: 8
ctcggaagcc atacctaatg gttgtttcgg                                   30

<210> SEQ ID NO 9
<211> LENGTH: 27
<212> TYPE: DNA
<213> ORGANISM: Homo sapiens

<400> SEQUENCE: 9
cttccgagtc atcgcagaga agtgtcc                                      27

<210> SEQ ID NO 10
<211> LENGTH: 27
<212> TYPE: DNA
<213> ORGANISM: Homo sapiens

<400> SEQUENCE: 10
ggacacttct ctgcgatgac tcggaag                                      27

<210> SEQ ID NO 11
<211> LENGTH: 26
<212> TYPE: DNA
<213> ORGANISM: Homo sapiens

<400> SEQUENCE: 11
ggattatact ccgcttggtc caggcc                                       26

<210> SEQ ID NO 12
<211> LENGTH: 26
<212> TYPE: DNA
<213> ORGANISM: Homo sapiens

<400> SEQUENCE: 12
ggcctggacc aagcggagta taatcc                                       26

<210> SEQ ID NO 13
<211> LENGTH: 419
<212> TYPE: PRT
<213> ORGANISM: Homo sapiens

<400> SEQUENCE: 13

Met Ala Gly Asp Ser Arg Asn Ala Met Asn Gln Asp Met Glu Ile Gly

-continued

```
1               5                   10                  15
Val Thr Pro Trp Asp Pro Lys Lys Ile Pro Lys Gln Ala Arg Asp Tyr
                20                  25                  30
Val Pro Ile Ala Thr Asp Arg Thr Arg Leu Leu Ala Glu Gly Lys Lys
                35                  40                  45
Pro Arg Gln Arg Tyr Met Glu Lys Ser Gly Lys Cys Asn Val His His
 50                  55                  60
Gly Asn Val Gln Glu Thr Tyr Arg Tyr Leu Ser Asp Leu Phe Thr Thr
 65                  70                  75                  80
Leu Val Asp Leu Lys Trp Arg Phe Asn Leu Val Phe Thr Met Val
                85                  90                  95
Tyr Thr Val Thr Trp Leu Phe Phe Gly Phe Ile Trp Leu Ile Ala
                100                 105                 110
Tyr Ile Arg Gly Asp Leu Asp His Val Gly Asp Gln Glu Trp Ile Pro
                115                 120                 125
Cys Val Glu Asn Leu Ser Gly Phe Val Ser Ala Phe Leu Phe Ser Ile
                130                 135                 140
Glu Thr Glu Thr Thr Ile Gly Tyr Gly Phe Arg Val Ile Thr Glu Lys
145                 150                 155                 160
Cys Pro Glu Gly Ile Ile Leu Leu Leu Val Gln Ala Ile Leu Gly Ser
                165                 170                 175
Ile Val Asn Ala Phe Met Val Gly Cys Met Phe Val Lys Ile Ser Gln
                180                 185                 190
Pro Lys Lys Arg Ala Glu Thr Leu Met Phe Ser Asn Asn Ala Val Ile
                195                 200                 205
Ser Met Arg Asp Glu Lys Leu Cys Leu Met Phe Arg Val Gly Asp Leu
 210                 215                 220
Arg Asn Ser His Ile Val Glu Ala Ser Ile Arg Ala Lys Leu Ile Lys
 225                 230                 235                 240
Ser Arg Gln Thr Lys Glu Gly Glu Phe Ile Pro Leu Asn Gln Thr Asp
                245                 250                 255
Ile Asn Val Gly Phe Asp Thr Gly Asp Asp Arg Leu Phe Leu Val Ser
                260                 265                 270
Pro Leu Ile Ile Ser His Glu Ile Asn Gln Lys Ser Pro Phe Trp Glu
                275                 280                 285
Met Ser Gln Ala Gln Leu His Gln Glu Glu Phe Glu Val Val Val Ile
                290                 295                 300
Leu Glu Gly Met Val Glu Ala Thr Gly Met Thr Cys Gln Ala Arg Ser
 305                 310                 315                 320
Ser Tyr Met Asp Thr Glu Val Leu Trp Gly His Arg Phe Thr Pro Val
                325                 330                 335
Leu Thr Leu Glu Lys Gly Phe Tyr Glu Val Asp Tyr Asn Thr Phe His
                340                 345                 350
Asp Thr Tyr Glu Thr Asn Thr Pro Ser Cys Cys Ala Lys Glu Leu Ala
                355                 360                 365
Glu Met Lys Arg Glu Gly Arg Leu Leu Gln Tyr Leu Pro Ser Pro Pro
 370                 375                 380
Leu Leu Gly Gly Cys Ala Glu Ala Gly Leu Asp Ala Glu Ala Glu Gln
 385                 390                 395                 400
Asn Glu Glu Asp Glu Pro Lys Gly Leu Gly Gly Ser Arg Glu Ala Arg
                405                 410                 415
Gly Ser Val
```

```
<210> SEQ ID NO 14
<211> LENGTH: 22
<212> TYPE: DNA
<213> ORGANISM: Homo sapiens

<400> SEQUENCE: 14
ctagtgaatc agaacagccc ac                                              22

<210> SEQ ID NO 15
<211> LENGTH: 20
<212> TYPE: DNA
<213> ORGANISM: Homo sapiens

<400> SEQUENCE: 15
aaggaatcca ctcttggtcg                                                 20

<210> SEQ ID NO 16
<211> LENGTH: 20
<212> TYPE: DNA
<213> ORGANISM: Homo sapiens

<400> SEQUENCE: 16
gcttcatttg gtggctcatt                                                 20

<210> SEQ ID NO 17
<211> LENGTH: 19
<212> TYPE: DNA
<213> ORGANISM: Homo sapiens

<400> SEQUENCE: 17
ccaccatgaa ggcattgac                                                  19

<210> SEQ ID NO 18
<211> LENGTH: 20
<212> TYPE: DNA
<213> ORGANISM: Homo sapiens

<400> SEQUENCE: 18
gtgtccgctt tcctgttctc                                                 20

<210> SEQ ID NO 19
<211> LENGTH: 21
<212> TYPE: DNA
<213> ORGANISM: Homo sapiens

<400> SEQUENCE: 19
ctaagtctga agtgtaggta g                                               21

<210> SEQ ID NO 20
<211> LENGTH: 21
<212> TYPE: DNA
<213> ORGANISM: Homo sapiens

<400> SEQUENCE: 20
aatggatgga tagatggatg g                                               21

<210> SEQ ID NO 21
<211> LENGTH: 20
<212> TYPE: DNA
<213> ORGANISM: Homo sapiens

<400> SEQUENCE: 21
gtctgtgttc actgaagcca                                                 20
```

```
<210> SEQ ID NO 22
<211> LENGTH: 20
<212> TYPE: DNA
<213> ORGANISM: Homo sapiens

<400> SEQUENCE: 22
cgaccaagag tggattcctt                                               20

<210> SEQ ID NO 23
<211> LENGTH: 20
<212> TYPE: DNA
<213> ORGANISM: Homo sapiens

<400> SEQUENCE: 23
agggtctccg ctctcttctt                                               20

<210> SEQ ID NO 24
<211> LENGTH: 20
<212> TYPE: DNA
<213> ORGANISM: Homo sapiens

<400> SEQUENCE: 24
gcttcatttg gtggctcatt                                               20

<210> SEQ ID NO 25
<211> LENGTH: 21
<212> TYPE: DNA
<213> ORGANISM: Homo sapiens

<400> SEQUENCE: 25
gtctgtgttc actgaagcca g                                             21

<210> SEQ ID NO 26
<211> LENGTH: 28
<212> TYPE: PRT
<213> ORGANISM: Homo sapiens

<400> SEQUENCE: 26

Thr Glu Thr Thr Ile Gly Tyr Gly Phe Arg Val Ile Thr Glu Lys Cys
 1               5                  10                  15

Pro Glu Gly Ile Ile Leu Leu Leu Val Gln Ala Ile
            20                  25

<210> SEQ ID NO 27
<211> LENGTH: 28
<212> TYPE: PRT
<213> ORGANISM: Mus musculus

<400> SEQUENCE: 27

Thr Glu Thr Thr Ile Gly Tyr Gly Phe Arg Val Ile Thr Glu Lys Cys
 1               5                  10                  15

Pro Glu Gly Ile Ile Leu Leu Leu Val Gln Ala Ile
            20                  25

<210> SEQ ID NO 28
<211> LENGTH: 28
<212> TYPE: PRT
<213> ORGANISM: Gallus gallus

<400> SEQUENCE: 28

Thr Glu Thr Thr Ile Gly Tyr Gly Tyr Arg Val Ile Thr Glu Lys Cys
 1               5                  10                  15
```

Pro Glu Gly Ile Val Leu Leu Ile Gln Ala Ile
            20                  25

<210> SEQ ID NO 29
<211> LENGTH: 28
<212> TYPE: PRT
<213> ORGANISM: Xenopus tropicalis

<400> SEQUENCE: 29

Thr Glu Thr Thr Ile Gly Tyr Gly Tyr Arg Val Ile Thr Glu Lys Cys
1               5                   10                  15

Pro Glu Gly Ile Val Leu Leu Val Gln Ala Ile
            20                  25

<210> SEQ ID NO 30
<211> LENGTH: 28
<212> TYPE: PRT
<213> ORGANISM: Danio rerio

<400> SEQUENCE: 30

Thr Glu Thr Thr Ile Gly Tyr Gly Tyr Arg Val Ile Thr Glu Lys Cys
1               5                   10                  15

Pro Glu Gly Ile Ile Leu Leu Met Val Gln Ala Ile
            20                  25

<210> SEQ ID NO 31
<211> LENGTH: 28
<212> TYPE: PRT
<213> ORGANISM: Ciona intestinalis

<400> SEQUENCE: 31

Thr Gln Val Thr Ile Gly Tyr Gly Thr Arg Ala Ile Thr Asp Val Cys
1               5                   10                  15

Pro Glu Ala Ile Ile Leu Leu Ile Val Gln Cys Ile
            20                  25

<210> SEQ ID NO 32
<211> LENGTH: 28
<212> TYPE: PRT
<213> ORGANISM: Homo sapiens

<400> SEQUENCE: 32

Thr Gln Val Thr Ile Gly Tyr Gly Phe Arg Cys Val Thr Glu Gln Cys
1               5                   10                  15

Ala Thr Ala Ile Phe Leu Leu Ile Phe Gln Ser Ile
            20                  25

<210> SEQ ID NO 33
<211> LENGTH: 28
<212> TYPE: PRT
<213> ORGANISM: Homo sapiens

<400> SEQUENCE: 33

Thr Gln Thr Thr Ile Gly Tyr Gly Phe Arg Cys Val Thr Asp Glu Cys
1               5                   10                  15

Pro Ile Ala Val Phe Met Val Val Phe Gln Ser Ile
            20                  25

<210> SEQ ID NO 34
<211> LENGTH: 28
<212> TYPE: PRT
<213> ORGANISM: Homo sapiens

<400> SEQUENCE: 34

Thr Gln Thr Thr Ile Gly Tyr Gly Leu Arg Cys Val Thr Glu Glu Cys
1               5                   10                  15

Pro Val Ala Val Phe Met Val Val Ala Gln Ser Ile
            20                  25

<210> SEQ ID NO 35
<211> LENGTH: 28
<212> TYPE: PRT
<213> ORGANISM: Homo sapiens

<400> SEQUENCE: 35

Thr Glu Ala Thr Ile Gly Tyr Gly Tyr Arg Tyr Ile Thr Asp Lys Cys
1               5                   10                  15

Pro Glu Gly Ile Ile Leu Phe Leu Phe Gln Ser Ile
            20                  25

<210> SEQ ID NO 36
<211> LENGTH: 28
<212> TYPE: PRT
<213> ORGANISM: Homo sapiens

<400> SEQUENCE: 36

Ser Gln Thr Thr Ile Gly Tyr Gly Phe Arg Tyr Ile Ser Glu Glu Cys
1               5                   10                  15

Pro Leu Ala Ile Val Leu Leu Ile Ala Gln Leu Val
            20                  25

<210> SEQ ID NO 37
<211> LENGTH: 28
<212> TYPE: PRT
<213> ORGANISM: Homo sapiens

<400> SEQUENCE: 37

Thr Gln Thr Thr Ile Gly Tyr Gly Tyr Arg Cys Val Thr Glu Glu Cys
1               5                   10                  15

Ser Val Ala Val Leu Met Val Ile Leu Gln Ser Ile
            20                  25

<210> SEQ ID NO 38
<211> LENGTH: 28
<212> TYPE: PRT
<213> ORGANISM: Homo sapiens

<400> SEQUENCE: 38

Val Gln Val Thr Ile Gly Phe Gly Gly Arg Met Met Thr Glu Glu Cys
1               5                   10                  15

Pro Leu Ala Ile Thr Val Leu Ile Leu Gln Asn Ile
            20                  25

<210> SEQ ID NO 39
<211> LENGTH: 28
<212> TYPE: PRT
<213> ORGANISM: Homo sapiens

<400> SEQUENCE: 39

Thr Gln Leu Thr Ile Gly Tyr Gly Thr Met Phe Pro Ser Gly Asp Cys
1               5                   10                  15

Pro Ser Ala Ile Ala Leu Leu Ala Ile Gln Met Leu
            20                  25

<210> SEQ ID NO 40
<211> LENGTH: 45
<212> TYPE: PRT
<213> ORGANISM: Homo sapiens

<400> SEQUENCE: 40

Ala Val Glu Asn Leu Ser Gly Phe Val Ser Ala Phe Leu Phe Ser Ile
1               5                   10                  15
Glu Thr Glu Thr Thr Ile Gly Tyr Gly Phe Arg Val Ile Thr Glu Lys
            20                  25                  30
Cys Pro Glu Gly Ile Ile Leu Leu Leu Val Gln Ala Ile
        35                  40                  45

<210> SEQ ID NO 41
<211> LENGTH: 45
<212> TYPE: PRT
<213> ORGANISM: Homo sapiens

<400> SEQUENCE: 41

Ala Val Glu Asn Leu Ser Gly Phe Val Ser Ala Phe Leu Phe Ser Ile
1               5                   10                  15
Glu Thr Glu Thr Thr Ile Arg Tyr Gly Phe Arg Val Ile Thr Glu Lys
            20                  25                  30
Cys Pro Glu Gly Ile Ile Leu Leu Leu Val Gln Ala Ile
        35                  40                  45

<210> SEQ ID NO 42
<211> LENGTH: 138
<212> TYPE: DNA
<213> ORGANISM: Homo sapiens

<400> SEQUENCE: 42
ttgtgttgaa aacctcagtg gcttcgtgtc cgctttcctg ttctccattg agaccgaaac      60
aaccattggg tatggcttcc gagtcatcac agagaagtgt ccagagggga ttatactcct    120
cttggtccag gccatcct                                                  138

<210> SEQ ID NO 43
<211> LENGTH: 71
<212> TYPE: DNA
<213> ORGANISM: Artificial Sequence
<220> FEATURE:
<223> OTHER INFORMATION: chemically synthesized

<400> SEQUENCE: 43
ttgtgttgaa aacctcagtg gcttcgtgtc cgctttcctg ttctccattg agaccgaaac      60
aaccattagg t                                                          71

<210> SEQ ID NO 44
<211> LENGTH: 71
<212> TYPE: DNA
<213> ORGANISM: Artificial Sequence
<220> FEATURE:
<223> OTHER INFORMATION: Chemically synthesized

<400> SEQUENCE: 44
tgttgaaaac ctcagtggct tcgtgtccgc tttcctgttc tccattgaga ccgaaacaac      60
cattgggtat g                                                          71

<210> SEQ ID NO 45
<211> LENGTH: 71

```
<212> TYPE: DNA
<213> ORGANISM: Artificial Sequence
<220> FEATURE:
<223> OTHER INFORMATION: Chemically synthesized

<400> SEQUENCE: 45
ttgaaaacct cagtggcttc gtgtccgctt tcctgttctc cattgagacc gaaacaacca    60
ttaggtatgg c                                                          71

<210> SEQ ID NO 46
<211> LENGTH: 71
<212> TYPE: DNA
<213> ORGANISM: Artificial Sequence
<220> FEATURE:
<223> OTHER INFORMATION: Chemically synthesized

<400> SEQUENCE: 46
gaaaacctca gtggcttcgt gtccgctttc ctgttctcca ttgagaccga acaaccatt     60 gggtatggct t                                                          71

<210> SEQ ID NO 47
<211> LENGTH: 71
<212> TYPE: DNA
<213> ORGANISM: Artificial Sequence
<220> FEATURE:
<223> OTHER INFORMATION: Chemically synthesized

<400> SEQUENCE: 47
aacctcagtg gcttcgtgtc cgctttcctg ttctccattg agaccgaaac aaccattagg    60
tatggcttcc g                                                          71

<210> SEQ ID NO 48
<211> LENGTH: 71
<212> TYPE: DNA
<213> ORGANISM: Artificial Sequence
<220> FEATURE:
<223> OTHER INFORMATION: Chemically synthesized

<400> SEQUENCE: 48
acctcagtgg cttcgtgtcc gctttcctgt tctccattga ccgaaaca accattgggt      60 atggcttccg a                                                          71

<210> SEQ ID NO 49
<211> LENGTH: 71
<212> TYPE: DNA
<213> ORGANISM: Artificial Sequence
<220> FEATURE:
<223> OTHER INFORMATION: Chemically synthesized

<400> SEQUENCE: 49
ctcagtggct tcgtgtccgc tttcctgttc tccattgaga ccgaaacaac cattaggtat    60
ggcttccgag t                                                          71

<210> SEQ ID NO 50
<211> LENGTH: 71
<212> TYPE: DNA
<213> ORGANISM: Artificial Sequence
<220> FEATURE:
<223> OTHER INFORMATION: Chemically synthesized

<400> SEQUENCE: 50
cagtggcttc gtgtccgctt tcctgttctc cattgagacc gaaacaacca ttgggtatgg    60
```
cttccgagtc a         71

<210> SEQ ID NO 51
<211> LENGTH: 71
<212> TYPE: DNA
<213> ORGANISM: Artificial Sequence
<220> FEATURE:
<223> OTHER INFORMATION: Chemically synthesized

<400> SEQUENCE: 51
gcttcgtgtc cgctttcctg ttctccattg agaccgaaac aaccattggg tatggcttcc         60
gagtcatcac a         71

<210> SEQ ID NO 52
<211> LENGTH: 71
<212> TYPE: DNA
<213> ORGANISM: Artificial Sequence
<220> FEATURE:
<223> OTHER INFORMATION: Chemically synthesized

<400> SEQUENCE: 52
tcgtgtccgc tttcctgttc tccattgaga ccgaaacaac cattgggtat ggcttccgag         60
tcatcacaga g         71

<210> SEQ ID NO 53
<211> LENGTH: 71
<212> TYPE: DNA
<213> ORGANISM: Artificial Sequence
<220> FEATURE:
<223> OTHER INFORMATION: Chemically synthesized

<400> SEQUENCE: 53
cgtgtccgct ttcctgttct ccattgagac cgaaacaacc attgggtatg gcttccgagt         60
catcacagag a         71

<210> SEQ ID NO 54
<211> LENGTH: 71
<212> TYPE: DNA
<213> ORGANISM: Artificial Sequence
<220> FEATURE:
<223> OTHER INFORMATION: Chemically synthesized

<400> SEQUENCE: 54
gtgtccgctt tcctgttctc cattgagacc gaaacaacca tgggtatgg cttccgagtc         60 atcacagaga a         71

<210> SEQ ID NO 55
<211> LENGTH: 71
<212> TYPE: DNA
<213> ORGANISM: Artificial Sequence
<220> FEATURE:
<223> OTHER INFORMATION: Chemically synthesized

<400> SEQUENCE: 55
tgtccgcttt cctgttctcc attgagaccg aaacaaccat gggtatggc ttccgagtca         60 tcacagagaa g         71

<210> SEQ ID NO 56
<211> LENGTH: 71
<212> TYPE: DNA
<213> ORGANISM: Artificial Sequence
<220> FEATURE:
<223> OTHER INFORMATION: Chemically synthesized

<400> SEQUENCE: 56
ccgctttcct gttctccatt gagaccgaaa caaccattgg gtatggcttc cgagtcatca    60
cagagaagtg t    71

<210> SEQ ID NO 57
<211> LENGTH: 71
<212> TYPE: DNA
<213> ORGANISM: Artificial Sequence
<220> FEATURE:
<223> OTHER INFORMATION: Chemically synthesized

<400> SEQUENCE: 57
ctttcctgtt ctccattgag accgaaacaa ccattgggta tggcttccga gtcatcacag    60
agaagtgtcc a    71

<210> SEQ ID NO 58
<211> LENGTH: 71
<212> TYPE: DNA
<213> ORGANISM: Artificial Sequence
<220> FEATURE:
<223> OTHER INFORMATION: Chemically synthesized

<400> SEQUENCE: 58
tttcctgttc tccattgaga ccgaaacaac cattgggtat ggcttccgag tcatcacaga    60
gaagtgtcca g    71

<210> SEQ ID NO 59
<211> LENGTH: 71
<212> TYPE: DNA
<213> ORGANISM: Artificial Sequence
<220> FEATURE:
<223> OTHER INFORMATION: Chemically synthesized

<400> SEQUENCE: 59
ttcctgttct ccattgagac cgaaacaacc attaggtatg gcttccgagt catcacagag    60
aagtgtccag a    71

<210> SEQ ID NO 60
<211> LENGTH: 71
<212> TYPE: DNA
<213> ORGANISM: Artificial Sequence
<220> FEATURE:
<223> OTHER INFORMATION: Chemically synthesized

<400> SEQUENCE: 60
cctgttctcc attgagaccg aaacaaccat gggtatggc ttccgagtca tcacagagaa    60
gtgtccagag g    71

<210> SEQ ID NO 61
<211> LENGTH: 71
<212> TYPE: DNA
<213> ORGANISM: Artificial Sequence
<220> FEATURE:
<223> OTHER INFORMATION: Chemically synthesized

<400> SEQUENCE: 61
ttctccattg agaccgaaac aaccattggg tatggcttcc gagtcatcac agagaagtgt    60
ccagaggggg g    71

<210> SEQ ID NO 62

```
<211> LENGTH: 71
<212> TYPE: DNA
<213> ORGANISM: Artificial Sequence
<220> FEATURE:
<223> OTHER INFORMATION: Chemically synthesized

<400> SEQUENCE: 62
ctccattgag accgaaacaa ccattgggta tggcttccga gtcatcacag agaagtgtcc    60 aggggggtt a                                                          71

<210> SEQ ID NO 63
<211> LENGTH: 71
<212> TYPE: DNA
<213> ORGANISM: Artificial Sequence
<220> FEATURE:
<223> OTHER INFORMATION: Chemically synthesized

<400> SEQUENCE: 63
cattgagacc gaaacaacca ttgggtatgg cttccgagtc atcacagaga agtgtccaga    60
ggggattata c                                                         71

<210> SEQ ID NO 64
<211> LENGTH: 71
<212> TYPE: DNA
<213> ORGANISM: Artificial Sequence
<220> FEATURE:
<223> OTHER INFORMATION: Chemically synthesized

<400> SEQUENCE: 64
ttgagaccga acaaccatt gggtatggct tccgagtcat cacagagaag tgtccagagg     60
ggggtatact c                                                         71

<210> SEQ ID NO 65
<211> LENGTH: 71
<212> TYPE: DNA
<213> ORGANISM: Artificial Sequence
<220> FEATURE:
<223> OTHER INFORMATION: Chemically synthesized

<400> SEQUENCE: 65
tgagaccgaa acaaccattg gtatggctt ccgagtcatc acagagaagt gtccagaggg     60
gattatactc c                                                         71

<210> SEQ ID NO 66
<211> LENGTH: 71
<212> TYPE: DNA
<213> ORGANISM: Artificial Sequence
<220> FEATURE:
<223> OTHER INFORMATION: Chemically synthesized

<400> SEQUENCE: 66
agaccgaaac aaccattggg tatgcttcc gagtcatcac agagaagtgt ccagagggga     60
ttatactcct c                                                         71

<210> SEQ ID NO 67
<211> LENGTH: 71
<212> TYPE: DNA
<213> ORGANISM: Artificial Sequence
<220> FEATURE:
<223> OTHER INFORMATION: Chemically synthesized

<400> SEQUENCE: 67
ccgaaacaac cattgggtat ggcttccgag tcatcacaga gaagtgtcca gaggggatta    60
```
tactcctctt g                                                          71

<210> SEQ ID NO 68
<211> LENGTH: 71
<212> TYPE: DNA
<213> ORGANISM: Artificial Sequence
<220> FEATURE:
<223> OTHER INFORMATION: Chemically synthesized

<400> SEQUENCE: 68
cgaaacaacc attgggtatg gcttccgagt catcacagag aagtgtccag agggattat      60 actcctcttg g                                                          71

<210> SEQ ID NO 69
<211> LENGTH: 71
<212> TYPE: DNA
<213> ORGANISM: Artificial Sequence
<220> FEATURE:
<223> OTHER INFORMATION: Chemically synthesized

<400> SEQUENCE: 69
gaaacaacca ttaggtatgg cttccgagtc atcacagaga agtgtccaga ggggattata     60
ctcctcttgg t                                                          71

<210> SEQ ID NO 70
<211> LENGTH: 71
<212> TYPE: DNA
<213> ORGANISM: Artificial Sequence
<220> FEATURE:
<223> OTHER INFORMATION: Chemically synthesized

<400> SEQUENCE: 70
gaaacaacca ttaggtatgg cttccgagtc atcacagaga agtgtccaga ggggattata     60
ctccccttgg t                                                          71

<210> SEQ ID NO 71
<211> LENGTH: 71
<212> TYPE: DNA
<213> ORGANISM: Artificial Sequence
<220> FEATURE:
<223> OTHER INFORMATION: Chemically synthesized

<400> SEQUENCE: 71
aaacaaccat taggtatggc ttccgagtca tcacagagaa gtgtccagag ggattatac     60 tcctcttggt c                                                          71

<210> SEQ ID NO 72
<211> LENGTH: 71
<212> TYPE: DNA
<213> ORGANISM: Artificial Sequence
<220> FEATURE:
<223> OTHER INFORMATION: Chemically synthesized

<400> SEQUENCE: 72
acaaccattg ggtatggctt ccgagtcatc acagagaagt gtccagaggg gattatactc     60
ctcttggtcc c                                                          71

<210> SEQ ID NO 73
<211> LENGTH: 71
<212> TYPE: DNA
<213> ORGANISM: Artificial Sequence
<220> FEATURE:

<223> OTHER INFORMATION: Chemically synthesized

<400> SEQUENCE: 73
caaccattgg gtatggcttc cgagtcatca cagagaagtg tccagagggg attatactcc    60
tcttggtcca g                                                        71

<210> SEQ ID NO 74
<211> LENGTH: 71
<212> TYPE: DNA
<213> ORGANISM: Artificial Sequence
<220> FEATURE:
<223> OTHER INFORMATION: Chemically synthesized

<400> SEQUENCE: 74
aaccattggg tatggcttcc gagtcatcac agagaagtgt ccagagggga ttatactcct    60
cttggtccag g                                                        71

<210> SEQ ID NO 75
<211> LENGTH: 71
<212> TYPE: DNA
<213> ORGANISM: Artificial Sequence
<220> FEATURE:
<223> OTHER INFORMATION: Chemically synthesized

<400> SEQUENCE: 75
accattaggt atggcttccg agtcatcaca gagaagtgtc cagaggggat tatactcctc    60
ttggtccagg c                                                        71

<210> SEQ ID NO 76
<211> LENGTH: 71
<212> TYPE: DNA
<213> ORGANISM: Artificial Sequence
<220> FEATURE:
<223> OTHER INFORMATION: Chemically synthesized

<400> SEQUENCE: 76
attgggtatg gcttccgagt catcacagag aagtgtccag agggattat actcctcttg     60 gtccaggcca t                                                        71

<210> SEQ ID NO 77
<211> LENGTH: 71
<212> TYPE: DNA
<213> ORGANISM: Artificial Sequence
<220> FEATURE:
<223> OTHER INFORMATION: Chemically synthesized

<400> SEQUENCE: 77
ttgggtatgg cttccgagtc atcacagaga agtgtccaga ggggattata ctcctcttgg    60
tccaggccat c                                                        71

<210> SEQ ID NO 78
<211> LENGTH: 71
<212> TYPE: DNA
<213> ORGANISM: Artificial Sequence
<220> FEATURE:
<223> OTHER INFORMATION: Chemically synthesized

<400> SEQUENCE: 78
taggtatggc ttccgagtca tcacagagaa gtgtccagag gggattatac tcctcttggt    60
ccaggccatc c                                                        71

```
<210> SEQ ID NO 79
<211> LENGTH: 71
<212> TYPE: DNA
<213> ORGANISM: Artificial Sequence
<220> FEATURE:
<223> OTHER INFORMATION: Chemically synthesized

<400> SEQUENCE: 79
aggtatggct tccgagtcat cacagagaag tgtccagagg ggattatact cctcttggtc    60
caggccatcc t                                                         71

<210> SEQ ID NO 80
<211> LENGTH: 48
<212> TYPE: PRT
<213> ORGANISM: Homo sapiens

<400> SEQUENCE: 80

Glu Thr Glu Thr Thr Ile Gly Tyr Gly Phe Arg Val Ile Thr Glu Lys
1               5                   10                  15

Cys Pro Glu Gly Ile Ile Leu Leu Leu Val Gln Ala Ile Leu Gly Ser
            20                  25                  30

Ile Val Asn Ala Phe Met Val Gly Cys Met Phe Val Lys Ile Ser Gln
        35                  40                  45

<210> SEQ ID NO 81
<211> LENGTH: 48
<212> TYPE: PRT
<213> ORGANISM: Homo sapiens

<400> SEQUENCE: 81

Glu Thr Glu Thr Thr Ile Gly Tyr Gly Phe Arg Val Ile Thr Glu Lys
1               5                   10                  15

Cys Pro Glu Gly Ile Ile Leu Arg Leu Val Gln Ala Ile Leu Gly Ser
            20                  25                  30

Ile Val Asn Ala Phe Met Val Gly Cys Met Phe Val Lys Ile Ser Gln
        35                  40                  45

<210> SEQ ID NO 82
<211> LENGTH: 146
<212> TYPE: DNA
<213> ORGANISM: Homo sapiens

<400> SEQUENCE: 82
ttgagaccga aacaaccatt gggtatggct tccgagtcat cacagagaag tgtccagagg    60
ggattatact cctcttggtc caggccatcc tgggctccat cgtcaatgcc ttcatggtgg   120
ggtgcatgtt tgtcaagatc agccag                                        146

<210> SEQ ID NO 83
<211> LENGTH: 74
<212> TYPE: DNA
<213> ORGANISM: Artificial Sequence
<220> FEATURE:
<223> OTHER INFORMATION: Chemically synthesized

<400> SEQUENCE: 83
ttgagaccga aacaaccatt gggtatggct tccgagtcat cacagagaag tgtccagagg    60
ggattatact cctc                                                      74

<210> SEQ ID NO 84
<211> LENGTH: 74
<212> TYPE: DNA
```

<213> ORGANISM: Artificial Sequence
<220> FEATURE:
<223> OTHER INFORMATION: Chemically synthesized

<400> SEQUENCE: 84
agaccgaaac aaccattggg tatggcttcc gagtcatcac agagaagtgt ccagagggga    60
ttatactcct cttg                                                     74

<210> SEQ ID NO 85
<211> LENGTH: 74
<212> TYPE: DNA
<213> ORGANISM: Artificial Sequence
<220> FEATURE:
<223> OTHER INFORMATION: Chemically synthesized

<400> SEQUENCE: 85
accgaaacaa ccattgggta tggcttccga gtcatcacag agaagtgtcc agagggatt     60 atactcctct tggt                                                     74

<210> SEQ ID NO 86
<211> LENGTH: 74
<212> TYPE: DNA
<213> ORGANISM: Artificial Sequence
<220> FEATURE:
<223> OTHER INFORMATION: Chemically synthesized

<400> SEQUENCE: 86
aacaaccatt gggtatggct tccgagtcat cacagagaag tgtccagagg ggattatact    60
cctcttggtc cagg                                                     74

<210> SEQ ID NO 87
<211> LENGTH: 74
<212> TYPE: DNA
<213> ORGANISM: Artificial Sequence
<220> FEATURE:
<223> OTHER INFORMATION: Chemically synthesized

<400> SEQUENCE: 87
acaaccattg ggtatggctt ccgagtcatc acagagaagt gtccagaggg gattatactc    60
ctcttggtcc aggc                                                     74

<210> SEQ ID NO 88
<211> LENGTH: 74
<212> TYPE: DNA
<213> ORGANISM: Artificial Sequence
<220> FEATURE:
<223> OTHER INFORMATION: Chemically synthesized

<400> SEQUENCE: 88
accattgggt atggcttccg agtcatcaca gagaagtgtc cagaggggat tatactcctc    60
ttggtccagg ccat                                                     74

<210> SEQ ID NO 89
<211> LENGTH: 74
<212> TYPE: DNA
<213> ORGANISM: Artificial Sequence
<220> FEATURE:
<223> OTHER INFORMATION: Chemically synthesized

<400> SEQUENCE: 89
gggtatggct tccgagtcat cacagagaag tgtccagagg ggattatact cctcttggtc    60
caggccatcc tggg                                                     74

<210> SEQ ID NO 90
<211> LENGTH: 74
<212> TYPE: DNA
<213> ORGANISM: Artificial Sequence
<220> FEATURE:
<223> OTHER INFORMATION: Chemically synthesized

<400> SEQUENCE: 90
ggtatggctt ccgagtcatc acagagaagt gtccagaggg gattatactc ctcttggtcc    60
aggccatcct gggc                                                      74

<210> SEQ ID NO 91
<211> LENGTH: 74
<212> TYPE: DNA
<213> ORGANISM: Artificial Sequence
<220> FEATURE:
<223> OTHER INFORMATION: Chemically synthesized

<400> SEQUENCE: 91
atggcttccg agtcatcaca gagaagtgtc cagagggat tatactccgc ttggtccagg     60
ccatcctggg ctcc                                                      74

<210> SEQ ID NO 92
<211> LENGTH: 74
<212> TYPE: DNA
<213> ORGANISM: Artificial Sequence
<220> FEATURE:
<223> OTHER INFORMATION: Chemically synthesized

<400> SEQUENCE: 92
tcttccgayt catcacagaa aagtgtccag aggggattat actccgcttg gtccaggcca    60
tcctgggctc catc                                                      74

<210> SEQ ID NO 93
<211> LENGTH: 74
<212> TYPE: DNA
<213> ORGANISM: Artificial Sequence
<220> FEATURE:
<223> OTHER INFORMATION: Chemically synthesized

<400> SEQUENCE: 93
cttccgagtc atcacagaga agtgtccaga ggggattata tcctcttgg tccaggccat     60 cctgggctcc atcg                                                      74

<210> SEQ ID NO 94
<211> LENGTH: 74
<212> TYPE: DNA
<213> ORGANISM: Artificial Sequence
<220> FEATURE:
<223> OTHER INFORMATION: Chemically synthesized

<400> SEQUENCE: 94
ttccgagtca tcacagagaa gtgtccagag gggattatac tccgcttggt ccaggccatc    60
ctgggctcca tcgt                                                      74

<210> SEQ ID NO 95
<211> LENGTH: 74
<212> TYPE: DNA
<213> ORGANISM: Artificial Sequence
<220> FEATURE:
<223> OTHER INFORMATION: Chemically synthesized

```
<400> SEQUENCE: 95
ccgagtcatc acagagaagt gtccagaggg gattatactc cgcttggtcc aggccatcct      60
gggctccatc gtca                                                       74

<210> SEQ ID NO 96
<211> LENGTH: 74
<212> TYPE: DNA
<213> ORGANISM: Artificial Sequence
<220> FEATURE:
<223> OTHER INFORMATION: Chemically synthesized

<400> SEQUENCE: 96
cgagtcatca cagagaagtg tccagagggg attatactcc tcttggtcca ggccatcctg      60
ggctccatcg tcaa                                                       74

<210> SEQ ID NO 97
<211> LENGTH: 74
<212> TYPE: DNA
<213> ORGANISM: Artificial Sequence
<220> FEATURE:
<223> OTHER INFORMATION: Chemically synthesized

<400> SEQUENCE: 97
agtcatcaca gagaagtgtc cagaggggat tatactcctc ttggtccagg ccatcctggg      60
ctccatcgtc aatg                                                       74

<210> SEQ ID NO 98
<211> LENGTH: 74
<212> TYPE: DNA
<213> ORGANISM: Artificial Sequence
<220> FEATURE:
<223> OTHER INFORMATION: Chemically synthesized

<400> SEQUENCE: 98
tcatcacaga gaagtgtcca gaggggatta tactcctctt ggtccaggcc atcctgggct      60
ccatcgtcaa tgcc                                                       74

<210> SEQ ID NO 99
<211> LENGTH: 74
<212> TYPE: DNA
<213> ORGANISM: Artificial Sequence
<220> FEATURE:
<223> OTHER INFORMATION: Chemically synthesized

<400> SEQUENCE: 99
atcacagaga agtgtccaga ggggattata ctccgcttgg tccaggccat cctgggctcc      60
atcgtcaatg cctt                                                       74

<210> SEQ ID NO 100
<211> LENGTH: 74
<212> TYPE: DNA
<213> ORGANISM: Artificial Sequence
<220> FEATURE:
<223> OTHER INFORMATION: Chemically synthesized

<400> SEQUENCE: 100
cagagaagtg tccagagggg attatactcc tcttggtcca ggccatcctg ggctccatcg      60
tcaatgcctt catg                                                       74

<210> SEQ ID NO 101
<211> LENGTH: 74
```

```
<212> TYPE: DNA
<213> ORGANISM: Artificial Sequence
<220> FEATURE:
<223> OTHER INFORMATION: Chemically synthesized

<400> SEQUENCE: 101
gatgtgtcca gagggggatta tactcctctt ggtccaggcc atcctgggct ccatcgtcaa    60
tgccttcatg gtgg                                                      74

<210> SEQ ID NO 102
<211> LENGTH: 74
<212> TYPE: DNA
<213> ORGANISM: Artificial Sequence
<220> FEATURE:
<223> OTHER INFORMATION: Chemically synthesized

<400> SEQUENCE: 102
gtccagaggg gattatactc cgcttggtcc aggccatcct gggctccatc gtcaatgcct    60
tcatggtggg gtgc                                                     74

<210> SEQ ID NO 103
<211> LENGTH: 74
<212> TYPE: DNA
<213> ORGANISM: Artificial Sequence
<220> FEATURE:
<223> OTHER INFORMATION: Chemically synthesized

<400> SEQUENCE: 103
tccagagggg attatactcc tcttggtcca ggccatcctg gctccatcg tcaatgcctt     60 catggtgggg tgca                                                     74

<210> SEQ ID NO 104
<211> LENGTH: 74
<212> TYPE: DNA
<213> ORGANISM: Artificial Sequence
<220> FEATURE:
<223> OTHER INFORMATION: Chemically synthesized

<400> SEQUENCE: 104
cagaggggat tatactcctc ttggtccagg ccatcctggg ctccatcgtc aatgccttca    60
tggtggggtg catg                                                     74

<210> SEQ ID NO 105
<211> LENGTH: 74
<212> TYPE: DNA
<213> ORGANISM: Artificial Sequence
<220> FEATURE:
<223> OTHER INFORMATION: Chemically synthesized

<400> SEQUENCE: 105 agagggggatt atactcctct tggtccaggc catcctgggc tccatcgtca atgccttcat    60
ggtggggtgc atgt                                                      74

<210> SEQ ID NO 106
<211> LENGTH: 74
<212> TYPE: DNA
<213> ORGANISM: Artificial Sequence
<220> FEATURE:
<223> OTHER INFORMATION: Chemically synthesized

<400> SEQUENCE: 106
gaggggatta tactccgctt ggtccaggcc atcctgggct ccatcgtcaa tgccttcatg    60
```
gtggggtgca tgtt 74

<210> SEQ ID NO 107
<211> LENGTH: 74
<212> TYPE: DNA
<213> ORGANISM: Artificial Sequence
<220> FEATURE:
<223> OTHER INFORMATION: Chemically synthesized

<400> SEQUENCE: 107 agggattat actccgcttg gtccaggcca tcctgggctc catcgtcaat gccttcatgg    60
tggggtgcat gttt    74

<210> SEQ ID NO 108
<211> LENGTH: 74
<212> TYPE: DNA
<213> ORGANISM: Artificial Sequence
<220> FEATURE:
<223> OTHER INFORMATION: Chemically synthesized

<400> SEQUENCE: 108
gggattatac tcctcttggt ccaggccatc ctgggctcca tcgtcaatgc cttcatggtg    60
gggtgcatgt ttgt    74

<210> SEQ ID NO 109
<211> LENGTH: 74
<212> TYPE: DNA
<213> ORGANISM: Artificial Sequence
<220> FEATURE:
<223> OTHER INFORMATION: Chemically synthesized

<400> SEQUENCE: 109
gattatactc ctcttggtcc aggccatcct gggctccatc gtcaatgcct tcatggtggg    60
gtgcatgttt gtca    74

<210> SEQ ID NO 110
<211> LENGTH: 74
<212> TYPE: DNA
<213> ORGANISM: Artificial Sequence
<220> FEATURE:
<223> OTHER INFORMATION: Chemically synthesized

<400> SEQUENCE: 110
attatactcc tcttggtcca ggccatcctg ggctccatcg tcaatgcctt catggtgggg    60
tgcatgtttg tcaa    74

<210> SEQ ID NO 111
<211> LENGTH: 74
<212> TYPE: DNA
<213> ORGANISM: Artificial Sequence
<220> FEATURE:
<223> OTHER INFORMATION: Chemically synthesized

<400> SEQUENCE: 111
ttatactcct cttggtccag gccatcctgg gctccatcgt caatgccttc atggtgggt    60 gcatgtttgt caag    74

<210> SEQ ID NO 112
<211> LENGTH: 74
<212> TYPE: DNA
<213> ORGANISM: Artificial Sequence
<220> FEATURE:
<223> OTHER INFORMATION: Chemically synthesized

<400> SEQUENCE: 112
tactcctctt ggtccaggcc atcctgggct ccatcgtcaa tgccttcatg gtggggtgca    60
tgtttgtcaa gatc    74

<210> SEQ ID NO 113
<211> LENGTH: 74
<212> TYPE: DNA
<213> ORGANISM: Artificial Sequence
<220> FEATURE:
<223> OTHER INFORMATION: Chemically synthesized

<400> SEQUENCE: 113
actccgcttg gtccaggcca tcctgggctc catcgtcaat gccttcatgg tggggtgcat    60
gtttgtcaag atca    74

<210> SEQ ID NO 114
<211> LENGTH: 74
<212> TYPE: DNA
<213> ORGANISM: Artificial Sequence
<220> FEATURE:
<223> OTHER INFORMATION: Chemically synthesized

<400> SEQUENCE: 114
gcttggtcca ggccatcctg ggctccatcg tcaatgcctt catggtgggg tgcatgtttg    60
tcaagatcag ccag    74

<210> SEQ ID NO 115
<211> LENGTH: 15
<212> TYPE: DNA
<213> ORGANISM: Artificial Sequence
<220> FEATURE:
<223> OTHER INFORMATION: Chemically synthesized

<400> SEQUENCE: 115
tccattcaga ccgaa    15

<210> SEQ ID NO 116
<211> LENGTH: 5
<212> TYPE: PRT
<213> ORGANISM: Artificial Sequence
<220> FEATURE:
<223> OTHER INFORMATION: Chemically synthesized

<400> SEQUENCE: 116

Ser Ile Gln Thr Glu
1               5

<210> SEQ ID NO 117
<211> LENGTH: 15
<212> TYPE: DNA
<213> ORGANISM: Artificial Sequence
<220> FEATURE:
<223> OTHER INFORMATION: Chemically synthesized

<400> SEQUENCE: 117
atactccgct tggtc    15

<210> SEQ ID NO 118
<211> LENGTH: 5
<212> TYPE: PRT
<213> ORGANISM: Artificial Sequence
<220> FEATURE:
<223> OTHER INFORMATION: Chemically synthesized

<400> SEQUENCE: 118

Ile Leu Arg Leu Val
1               5

<210> SEQ ID NO 119
<211> LENGTH: 15
<212> TYPE: DNA
<213> ORGANISM: Artificial Sequence
<220> FEATURE:
<223> OTHER INFORMATION: Chemically synthesized

<400> SEQUENCE: 119
accattcggt atggc                                                    15

<210> SEQ ID NO 120
<211> LENGTH: 5
<212> TYPE: PRT
<213> ORGANISM: Artificial Sequence
<220> FEATURE:
<223> OTHER INFORMATION: Chemically synthesized

<400> SEQUENCE: 120

Thr Ile Arg Tyr Gly
1               5

<210> SEQ ID NO 121
<211> LENGTH: 15
<212> TYPE: DNA
<213> ORGANISM: Artificial Sequence
<220> FEATURE:
<223> OTHER INFORMATION: Chemically synthesized

<400> SEQUENCE: 121
accattaggt atggc                                                    15

<210> SEQ ID NO 122
<211> LENGTH: 33
<212> TYPE: PRT
<213> ORGANISM: Mus musculus

<400> SEQUENCE: 122

Leu Phe Ser Ile Glu Thr Glu Thr Thr Ile Gly Tyr Gly Phe Arg Val
1               5                   10                  15

Ile Thr Glu Lys Cys Pro Glu Gly Ile Ile Leu Leu Leu Val Gln Ala
            20                  25                  30

Ile

<210> SEQ ID NO 123
<211> LENGTH: 33
<212> TYPE: PRT
<213> ORGANISM: Gallus gallus

<400> SEQUENCE: 123

Leu Phe Ser Ile Glu Thr Glu Thr Thr Ile Gly Tyr Gly Tyr Arg Val
1               5                   10                  15

```
Ile Thr Glu Lys Cys Pro Glu Gly Ile Val Leu Leu Leu Ile Gln Ala
            20                  25                  30

Ile

<210> SEQ ID NO 124
<211> LENGTH: 33
<212> TYPE: PRT
<213> ORGANISM: Xenopus tropicalis

<400> SEQUENCE: 124

Leu Phe Ser Ile Glu Thr Glu Thr Thr Ile Gly Tyr Gly Tyr Arg Val
1               5                   10                  15

Ile Thr Glu Lys Cys Pro Glu Gly Ile Val Leu Leu Leu Val Gln Ala
            20                  25                  30

Ile

<210> SEQ ID NO 125
<211> LENGTH: 33
<212> TYPE: PRT
<213> ORGANISM: Danio rerio

<400> SEQUENCE: 125

Leu Phe Ser Ile Glu Thr Glu Thr Thr Ile Gly Tyr Gly Tyr Arg Val
1               5                   10                  15

Ile Thr Glu Lys Cys Pro Glu Gly Ile Ile Leu Leu Met Val Gln Ala
            20                  25                  30

Ile

<210> SEQ ID NO 126
<211> LENGTH: 33
<212> TYPE: PRT
<213> ORGANISM: Ciona intestinalis

<400> SEQUENCE: 126

Leu Phe Ser Ile Glu Thr Gln Val Thr Ile Gly Tyr Gly Thr Arg Ala
1               5                   10                  15

Ile Thr Asp Val Cys Pro Glu Ala Ile Ile Leu Leu Ile Val Gln Ser
            20                  25                  30

Ile

<210> SEQ ID NO 127
<211> LENGTH: 33
<212> TYPE: PRT
<213> ORGANISM: Homo sapiens

<400> SEQUENCE: 127

Leu Phe Ser Ile Glu Thr Glu Thr Thr Ile Gly Tyr Gly Phe Arg Val
1               5                   10                  15

Ile Thr Glu Lys Cys Pro Glu Gly Ile Ile Leu Leu Leu Val Gln Ala
            20                  25                  30

Ile
```